US011098318B2

(12) United States Patent
Abbitt et al.

(10) Patent No.: US 11,098,318 B2
(45) Date of Patent: Aug. 24, 2021

(54) TERMINATOR SEQUENCE FOR GENE EXPRESSION IN PLANTS

(71) Applicant: PIONEER HI-BRED INTERNATIONAL, INC., Johnston, IA (US)

(72) Inventors: Shane E Abbitt, Ankeny, IA (US); Rudolf Jung, Rupprechtstegen (DE)

(73) Assignee: PIONEER HI-BRED INTERNATIONAL, INC.

( * ) Notice: Subject to any disclaimer, the term of this patent is extended or adjusted under 35 U.S.C. 154(b) by 0 days.

(21) Appl. No.: 16/704,625

(22) Filed: Dec. 5, 2019

(65) Prior Publication Data

US 2020/0095594 A1 Mar. 26, 2020

Related U.S. Application Data

(63) Continuation of application No. 14/236,499, filed as application No. PCT/US2012/047901 on Jul. 23, 2012, now Pat. No. 10,538,775.

(60) Provisional application No. 61/514,055, filed on Aug. 2, 2011.

(51) Int. Cl.
*C12N 15/00* (2006.01)
*C12N 15/82* (2006.01)

(52) U.S. Cl.
CPC ......... *C12N 15/8216* (2013.01); *C12N 15/00* (2013.01)

(58) Field of Classification Search
None
See application file for complete search history.

(56) References Cited

U.S. PATENT DOCUMENTS

2004/0172684 A1 9/2004 Kovalic
2005/0250938 A1* 11/2005 Kriz .................. C12N 15/8216 536/24.1
2009/0089897 A1 4/2009 Abbitt et al.
2009/0320160 A1 12/2009 Li

OTHER PUBLICATIONS

Search Report for International Application No. PCT/US2012/047901 dated Oct. 12, 2012.
Written Opinion of the International Searching Authority for Application No. PCT/US2012/047901 dated Oct. 12, 2012.
International Preliminary Report on Patentability for Application No. PCT/US2012/047901 dated Feb. 4, 2014.
De Freitas FA et al., "Structural characterization and promoter activity analysis of the gamma-kafirin gene from sorghum," Molecular and General Genetics. (1994) 245(2):177-186.
Abbitt et al., Published Applications Database, Publication No. US20150074845A 1, SEQ ID No. 18, Mar. 12, 2015.

* cited by examiner

*Primary Examiner* — Phuong T Bui

(57) ABSTRACT

The present invention discloses polynucleotide sequences that can be used to regulate gene expression in plants. Terminator sequences from *Sorghum bicolor* that are functional in plants are disclosed.

17 Claims, 8 Drawing Sheets

Specification includes a Sequence Listing.

FIG. 6B

```
    C G T G T G T C C A A G A A A T G T A T C A G T G A T A C G T A T A T T C A C A A T T T T T T T A T Majority
                      210                 220                 230                 240                 250
201 C G T G T G T C C A A G A A A T G T A T C A G T G A T A C G T A T A T T C A C A A T T T T T T T A T SEQ ID 1.seq
200 C G T G T G T C C A A G A A A T G T A T C A G T G A T A C G T A T A T T C A C A A T T T T T T T A T SEQ ID 18.seq

    G A C T T A T A C T C A C A A T T T G T T T T T T T A C T A C T T A T A C T C X X A C A A T T T G T Majority
                      260                 270                 280                 290                 300
251 G A C T T A T A C T C A C A A T T T G T T T T T T T A C T A C T T A T A C T C - - A C A A T T T G T SEQ ID 1.seq
250 G A C T T A T A C T C A C A A T T T G T T T T T T T A C T A C T T A T A C T C G A A C A A T T T G T SEQ ID 18.seq

    T G T G G G T A C C A T A A C A A T T T C G A T C G A A T A T A T A T C A G A A A G T T G A C G A A Majority
                      310                 320                 330                 340                 350
299 T G T G G G T A C C A T A A C A A T T T C G A T C G A A T A T A T A T C A G A A A G T T G A C G A A SEQ ID 1.seq
300 T G T G G G T A C C A T A A C A A T T T C G A T C G A A T A T A T A T C A G A A A G T T G A C G A A SEQ ID 18.seq
```

FIG. 6C

```
    A G T A A G C T C A C T C A A A A A G T T A A A T G G G C T G C G G A A G C T G C G T C A G G C C C  Majority
                    360                 370                 380                 390                 400
349 A G T A A G C T C A C T C A A A A A G T T A A A T G G G C T G C G G A A G C T G C G T C A G G C C C  SEQ ID 1.seq
350 A G T A A G C T C A C T C A A A A A G T T A A A T G G G C T G C G G A A G C T G C G T C A G G C C C  SEQ ID 18.seq

    A A G T T T T G G C T A T T C T A T C C G G T A T C C A C G A T T T T G A T G G C T G A G G G A C A  Majority
                    410                 420                 430                 440                 450
399 A A G T T T T G G C T A T T C T A T C C G G T A T C C A C G A T T T T G A T G G C T G A G G G A C A  SEQ ID 1.seq
400 A A G T T T T G G C T A T T C T A T C C G G T A T C C A C G A T T T T G A T G G C T G A G G G A C A  SEQ ID 18.seq

    T A T G T T C G X X T                                                                              Majority
                    460
449 T A T G T T C G C T T                                                                              SEQ ID 1.seq
450 T A T G T T C G G C T                                                                              SEQ ID 18.seq
```

TERMINATOR SEQUENCE FOR GENE EXPRESSION IN PLANTS

CROSS REFERENCE TO RELATED APPLICATIONS

This application is a continuation of U.S. patent application Ser. No. 14/236,499, now U.S. Pat. No. 10,538,775, granted Jan. 20, 2020, which is a 371 filing of International Application No. PCT/US12/47901, filed Jul. 23, 2012, which claims the benefit of U.S. Provisional Application No. 61/514,055, filed Aug. 2, 2011, the entire content of each is herein incorporated by reference.

FIELD OF INVENTION

The present invention relates to the field of plant molecular biology and plant genetic engineering. More specifically, it relates to novel plant terminator sequences and their use to regulate gene expression in plants.

BACKGROUND

Recent advances in plant genetic engineering have opened new doors to engineer plants to have improved characteristics or traits. These transgenic plants characteristically have recombinant DNA constructs in their genome that have protein coding region operably linked to multiple regulatory regions that allow accurate expression of the transgene. A few examples of regulatory elements that help regulate gene expression in transgenic plants are promoters, introns, terminators, enhancers and silencers.

Plant genetic engineering has advanced to introducing multiple traits into commercially important plants, also known as gene stacking. This is accomplished by multigene transformation, where multiple genes are transferred to create a transgenic plant that might express a complex phenotype, or multiple phenotypes. But it is important to modulate or control the expression of each transgene optimally. The regulatory elements need to be diverse, to avoid introducing into the same transgenic plant repetitive sequences, which has been correlated with undesirable negative effects on transgene expression and stability (Peremarti et al (2010) *Plant Mol Biol* 73:363-378; Mette et al (1999) EMBO J 18:241-248; Mette et al (2000) *EMBO J* 19:5194-5201; Mourrain et al (2007) *Planta* 225:365-379, U.S. Pat. Nos. 7,632,982, 7,491,813, 7,674,950, PCT Application No. PCT/US2009/046968). Therefore it is important to discover and characterize novel regulatory elements that can be used to express heterologous nucleic acids in important crop species. Diverse regulatory regions can be used to control the expression of each transgene optimally.

Regulatory sequences located downstream of coding regions contain signals required for transcription termination and 3' mRNA processing, and are called terminator sequences. The terminator sequences play a key role in mRNA processing, localization, stability and translation (Proudfoot, N. (2004) *Curr. Op. Cell Biol* 16:272-278; Gilmartin, 2005). The 3' regulatory sequences contained in terminator sequences can affect the level of expression of a gene. Optimal expression of a chimeric gene in plant cells has been found to be dependent on the presence of appropriate 3' sequences (Ingelbrecht, I. L. W. et al (1989) *Plant Cell* 1:671-680). Read through transcription through leaky terminator of a gene can cause unwanted transcription of one transgene from promoter of another one. Also, bidirectional, convergent transcription of transgenes in transgenic plants can occur due to leaky transcription termination of separate convergent genes or from genomic promoters. Convergent, overlapping transcription can decrease transgene expression, or generate antisense RNA (Bieri, S. et al (2002) *Molecular Breeding* 10:107-117). This underlines the importance of discovering novel and efficient transcriptional terminators.

SUMMARY

The present invention relates to regulatory sequences for modulating gene expression in plants. Specifically, the present invention relates to terminator sequences. Recombinant DNA constructs comprising terminator sequences are provided.

An embodiment of this invention is an isolated polynucleotide sequence comprising: (a) the sequence set forth in SEQ ID NO:1 or SEQ ID NO:18; (b) a sequence with at least 95% sequence identity to SEQ ID NO:1 or SEQ ID NO:18; or (c) a sequence comprising a functional fragment of (a) or (b), wherein the isolated polynucleotide sequence functions as a terminator in a plant cell. Another embodiment of this invention is a recombinant construct comprising an isolated polynucleotide sequence comprising: (a) the sequence set forth in SEQ ID NO:1 or SEQ ID NO:18; (b) a sequence with at least 95% sequence identity to SEQ ID NO:1 or SEQ ID NO:18; or (c) a sequence comprising a functional fragment of (a) or (b), wherein the isolated polynucleotide sequence functions as a terminator in a plant cell. This recombinant construct may further comprise a promoter and a heterologous polynucleotide, wherein the promoter and the heterologous polynucleotide are operably linked to the isolated polynucleotide sequence.

Another embodiment of this invention is a method of expressing a heterologous polynucleotide in a plant, comprising the steps of (a) introducing into a regenerable plant cell the recombinant DNA construct described above; (b) regenerating a transgenic plant from the regenerable plant cell of (a); and (c) obtaining a progeny plant from the transgenic plant of step (b), wherein the transgenic plant and the progeny plant comprises the recombinant DNA construct and exhibits expression of the heterologous polynucleotide.

In another embodiment, this invention concerns a vector, virus, cell, microorganism, plant, or seed comprising a recombinant DNA construct comprising the terminator sequences described in the present invention.

The invention encompasses regenerated, mature and fertile transgenic plants comprising the recombinant DNA constructs described above, transgenic seeds produced therefrom, T1 and subsequent generations. The transgenic plant cells, tissues, plants, and seeds may comprise at least one recombinant DNA construct of interest.

In another embodiment, the plant or seed comprising the terminator sequences described in the present invention is a monocotyledenous plant or seed. In another embodiment, the plant or seed comprising the terminator sequences described in the present invention is a maize plant or seed.

In another embodiment, any of the methods of expressing a heterologous polynucleotide, wherein the plant cell is a monocotyledonous plant cell, e.g., a maize plant cell.

BRIEF DESCRIPTION OF DRAWINGS AND SEQUENCE LISTING

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. § 1.822.

FIG. 4A shows GUS reporter gene expression assayed at protein level, and FIG. 4B shows GUS reporter gene expression assayed with qRT-PCR.

FIG. 6A-6C show the alignment between the cloned SB-GKAF terminator (SEQ ID NO:1) and the nucleotides 1863 to 2322 of NCBI GI NO: 671655 (SEQ ID NO:18). The consensus sequence is show at the top, and the residues that match the consensus exactly are boxed.

Figure 1:
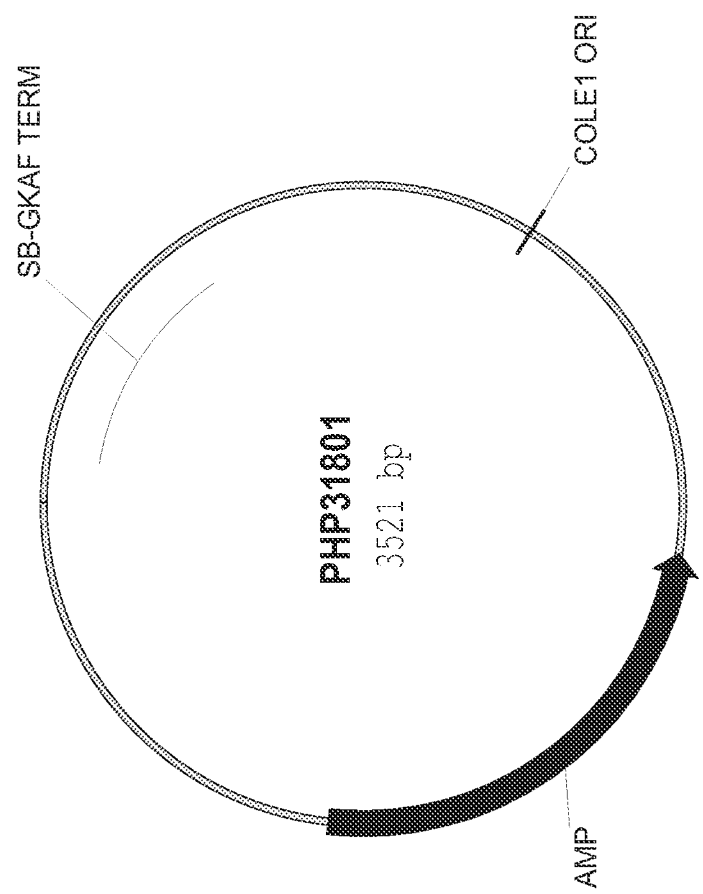
FIG. 1 shows the map of PHP31801, the vector used for cloning SB-GKAF terminator after amplification.

SEQ ID NO:1 is the sequence of the 459 bp SB-GKAF terminator.

SEQ ID NO:2 and 3 are the sequences of the forward and reverse primers used to amplify SB-GKAF terminator.

SEQ ID NO:4 is the nucleotide sequence of PHP31801, the vector used for cloning SB-GKAF terminator after PCR amplification.

SEQ ID NO:5 is the nucleotide sequence of PHP34074, the vector used for testing SB-GKAF terminator.

SEQ ID NO:6 is the nucleotide sequence of PHP34005, the test vector used as a control with PINII terminator.

SEQ ID NOS:7-9 are the sequences of the forward primer, reverse primer and probe used for assessing GUS expression by qRT-PCR in transgenic maize plants, as described in Table 2.

SEQ ID NOS:10-17 are the sequences of the primers used for quantitating read through transcription through SB-GKAF and PINII terminators, by qRT-PCR in transgenic maize plants, as described in Table 3.

SEQ ID NO:18 corresponds to nucleotides 1863 to 2322 of NCBI GI NO: 671655.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

The terms "monocot" and "monocotyledonous plant" are used interchangeably herein. A monocot of the current invention includes the Gramineae.

The terms "dicot" and "dicotyledonous plant" are used interchangeably herein. A dicot of the current invention includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, plant propagules, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Propagule" includes all products of meiosis and mitosis able to propagate a new plant, including but not limited to, seeds, spores and parts of a plant that serve as a means of vegetative reproduction, such as corms, tubers, offsets, or runners. Propagule also includes grafts where one portion of a plant is grafted to another portion of a different plant (even one of a different species) to create a living organism. Propagule also includes all plants and seeds produced by cloning or by bringing together meiotic products, or allowing meiotic products to come together to form an embryo or fertilized egg (naturally or with human intervention).

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

The commercial development of genetically improved germplasm has also advanced to the stage of introducing multiple traits into crop plants, often referred to as a gene stacking approach. In this approach, multiple genes conferring different characteristics of interest can be introduced into a plant. Gene stacking can be accomplished by many means including but not limited to co-transformation, retransformation, and crossing lines with different transgenes.

"Transgenic plant" also includes reference to plants which comprise more than one heterologous polynucleotide within their genome. Each heterologous polynucleotide may confer a different trait to the transgenic plant.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

"Coding region" refers to the portion of a messenger RNA (or the corresponding portion of another nucleic acid molecule such as a DNA molecule) which encodes a protein or polypeptide. "Non-coding region" refers to all portions of a messenger RNA or other nucleic acid molecule that are not a coding region, including but not limited to, for example, the promoter region, 5' untranslated region ("UTR"), 3' UTR, intron and terminator. The terms "coding region" and "coding sequence" are used interchangeably herein. The terms "non-coding region" and "non-coding sequence" are used interchangeably herein.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques.

"Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature. The terms "recombinant DNA construct" and "recombinant construct" are used interchangeably herein.

The terms "entry clone" and "entry vector" are used interchangeably herein.

"Regulatory sequences" or "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

Promoters that cause a gene to be expressed in most cell types at most times are commonly referred to as "constitutive promoters".

Inducible promoters selectively express an operably linked DNA sequence in response to the presence of an endogenous or exogenous stimulus, for example by chemical compounds (chemical inducers) or in response to environmental, hormonal, chemical, and/or developmental signals. Examples of inducible or regulated promoters include, but are not limited to, promoters regulated by light, heat, stress, flooding or drought, pathogens, phytohormones, wounding, or chemicals such as ethanol, jasmonate, salicylic acid, or safeners.

"Enhancer sequences" refer to the sequences that can increase gene expression. These sequences can be located upstream, within introns or downstream of the transcribed region. The transcribed region is comprised of the exons and the intervening introns, from the promoter to the transcription termination region. The enhancement of gene expression can be through various mechanisms which include, but are not limited to, increasing transcriptional efficiency, stabilization of mature mRNA and translational enhancement.

An "intron" is an intervening sequence in a gene that is transcribed into RNA and then excised in the process of generating the mature mRNA. The term is also used for the excised RNA sequences. An "exon" is a portion of the sequence of a gene that is transcribed and is found in the mature messenger RNA derived from the gene, and is not necessarily a part of the sequence that encodes the final gene product.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Overexpression" refers to the production of a gene product in transgenic organisms that exceeds levels of production in a null segregating (or non-transgenic) organism from the same experiment.

"Phenotype" means the detectable characteristics of a cell or organism.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

A "favorable allele" is the allele at a particular locus that confers, or contributes to, a desirable phenotype, e.g., increased cell wall digestibility, or alternatively, is an allele that allows the identification of plants with decreased cell wall digestibility that can be removed from a breeding program or planting ("counterselection"). A favorable allele of a marker is a marker allele that segregates with the favorable phenotype, or alternatively, segregates with the unfavorable plant phenotype, therefore providing the benefit of identifying plants.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, include lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

"Transcription terminator", "termination sequences", or "terminator" refer to DNA sequences located downstream of a coding sequence, including polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al., *Plant Cell* 1:671-680 (1989). A polynucleotide sequence with "terminator activity" refers to a polynucleotide sequence that, when operably linked to the 3' end of a second polynucleotide sequence that is to be expressed, is capable of terminating transcription from the second polynucleotide sequence. Transcription termination is the process by which RNA synthesis by RNA polymerase is stopped and both the RNA and the enzyme are released from the DNA template.

Improper termination of an RNA transcript can affect the stability of the RNA, and hence can affect protein expression. Variability of transgene expression is sometimes attributed to variability of termination efficiency (Bieri et al (2002) *Molecular Breeding* 10: 107-117).

The terms "SB-GKAF terminator", "GKAF terminator" and "gamma-kafirin terminator" are used interchangeably herein, and each refers to the sequence encoding the 3' untranslated region (3' UTR) of the *Sorghum Bicolor* gamma-kafirin gene and about 300 bp of sequence downstream from the 3' UTR. The sequence of the SB-GKAF terminator is given in SEQ ID NO:1. The *Sorghum bicolor* gamma-kafirin gene encodes a gamma-prolamin protein, and the sequence for this gene is given in NCBI GI NO: 671655. Prolamins are the major storage proteins of many cereals. The sorghum gamma-Kafirin, which is the γ-prolamin of sorghum, constitutes about 2-5% of total prolamin in sorghum endosperm, and is composed of a single polypeptide of 27 kDa (de Freitas F A et al (1994) *Mol Gen Genetics* 245(2):177-86).

The present invention encompasses functional fragments and variants of the terminator sequences disclosed herein.

A “functional fragment” of the terminator is defined as any subset of contiguous nucleotides of the terminator sequence disclosed herein, that can perform the same, or substantially similar function as the full length terminator sequence disclosed herein. A “functional fragment” with substantially similar function to the full length terminator disclosed herein refers to a functional fragment that retains the ability to terminate transcription largely at the same level as the full-length terminator sequence. A recombinant construct comprising a heterologous polynucleotide operably linked to a “functional fragment” of the terminator sequence disclosed herein exhibits levels of heterologous polynucleotide expression substantially similar to a corresponding recombinant construct comprising a heterologous polynucleotide operably linked to the full length terminator sequence. A “variant”, as used herein, is the sequence of the terminator or the sequence of a functional fragment of a terminator containing changes in which one or more nucleotides of the original sequence is deleted, added, and/or substituted, while substantially maintaining terminator function. One or more base pairs can be inserted, deleted, or substituted internally to a terminator, without affecting its activity. Fragments and variants can be obtained via methods such as site-directed mutagenesis and synthetic construction.

These terminator functional fragments may comprise at least 50, 75, 100, 125, 150, 175, 200, 225, 250, 275, 300, 325, 350, 375, 400, 425 or 450 contiguous nucleotides of the particular terminator nucleotide sequence disclosed herein. Such fragments may be obtained by use of restriction enzymes to cleave the naturally occurring terminator nucleotide sequences disclosed herein; by synthesizing a nucleotide sequence from the naturally occurring terminator DNA sequence; or may be obtained through the use of PCR technology. See particularly, Mullis et al., *Methods Enzymol.* 155:335-350 (1987), and Higuchi, R. In PCR Technology: Principles and Applications for DNA Amplifications; Erlich, H. A., Ed.; Stockton Press Inc.: New York, 1989. Again, variants of these terminator fragments, such as those resulting from site-directed mutagenesis, are encompassed by the compositions of the present invention.

The terms “substantially similar” and “corresponding substantially” as used herein refer to nucleic acid fragments, particularly terminator sequences, wherein changes in one or more nucleotide bases do not substantially alter the ability of the terminator to terminate transcription. These terms also refer to modifications, including deletions and variants, of the nucleic acid sequences of the instant invention by way of deletion or insertion of one or more nucleotides that do not substantially alter the functional properties of the resulting terminator relative to the initial, unmodified terminator. It is therefore understood, as those skilled in the art will appreciate, that the invention encompasses more than the specific exemplary sequences.

As will be evident to one of skill in the art, any heterologous polynucleotide of interest can be operably linked to the terminator sequences described in the current invention. Examples of polynucleotides of interest that can be operably linked to the terminator sequences described in this invention include, but are not limited to, polynucleotides comprising regulatory elements such as introns, enhancers, promoters, translation leader sequences, protein coding regions such as disease and insect resistance genes, genes conferring nutritional value, genes conferring yield and heterosis increase, genes that confer male and/or female sterility, antifungal, antibacterial or antiviral genes, and the like. Likewise, the terminator sequences described in the current invention can be used to terminate transcription of any nucleic acid that controls gene expression. Examples of nucleic acids that could be used to control gene expression include, but are not limited to, antisense oligonucleotides, suppression DNA constructs, or nucleic acids encoding transcription factors.

A recombinant DNA construct (including a suppression DNA construct) of the present invention may comprise at least one regulatory sequence. In an embodiment of the present invention, the regulatory sequences disclosed herein can be operably linked to any other regulatory sequence.

A number of promoters can be used in recombinant DNA constructs of the present invention. The promoters can be selected based on the desired outcome, and may include constitutive, tissue-specific, inducible, or other promoters for expression in the host organism.

The terms “real-time PCR”, “quantitative PCR”, “quantitative real-time PCR”, and “QPCR” are used interchangeably herein, and represent a variation of the standard polymerase chain reaction (PCR) technique used to quantify DNA or RNA in a sample. Using sequence-specific primers and a probe, the relative number or copies of a particular DNA or RNA sequence are determined. The term relative is used since this technique compares relative copy numbers between different genes with respect to a specific reference gene. The quantification arises by measuring the amount of amplified product at each cycle during the PCR process. Quantification of amplified product is obtained using fluorescent hydrolysis probes that measure increasing fluorescence for each subsequent PCR cycle. The Ct (cycle threshold) is defined as the number of cycles required for the fluorescent signal to cross the threshold (i.e., exceeds background level). DNA/RNA from genes with higher copy numbers will appear after fewer PCR cycles; so the lower a Ct value, the more copies are present in the specific sample. To quantify RNA, QPCR or real-time PCR is preceded by the step of reverse transcribing mRNA into cDNA. This is referred to herein as “real-time RT-PCR” or “quantitative RT-PCR” or “qRT-PCR”.

The Taqman method of PCR product quantification uses a fluorescent reporter probe. This is more accurate since the probe is designed to be sequence-specific and will only bind to the specific PCR product. The probe specificity allows for quantification even in the presence of non-specific DNA amplification. This allows for multiplexing, which quantitates several genes in the same tube, by using probes with different emission spectra. Breakdown of the probe by the 5' to 3' exonuclease activity of Taq polymerase removes the quencher and allows the PCR product to be detected.

When plotted on a linear scale, the fluorescent emission increase with PCR cycle number has a sigmoidal shape with an exponential phase and a plateau phase. The plateau phase is determined by the amount of primer in the master mix rather than the nucleotide template. Usually the vertical scale is plotted in a logarithmic fashion, allowing the intersection of the plot with the threshold to be linear and more easily visualized. Theoretically, the amount of DNA doubles every cycle during the exponential phase, but this is affected by the efficiency of the primers used. A positive control using a reference gene, e.g., a “housekeeping” gene that is relatively abundant in all cell types, is also performed to allow for comparisons between samples. The amount of DNA/RNA is determined by comparing the results to a standard curve produced by serial dilutions of a known concentration of DNA/RNA.

The present invention includes a polynucleotide comprising: (i) a nucleic acid sequence of at least 90%, 91%, 92%, 93%, 94%, 95%, 96%, 97%, 98%, 99%, or 100% sequence identity, based on the Clustal V (or Clustal W) method of alignment, when compared to SEQ ID NO:1 or SEQ ID NO:18; or (ii) a nucleic acid sequence of at least 90%, 91%, 92%, 93%, 94%, 95%, 96%, 97%, 98%, 99% or 100% sequence identity, based on the Clustal V (or Clustal W) method of alignment, when compared to a functional fragment of SEQ ID NO:1 or SEQ ID NO:18; or (iii) a full complement of the nucleic acid sequence of (i) or (ii), wherein the polynucleotide acts as a terminator in a plant cell.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp (1989) CABIOS. 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Alternatively, the Clustal W method of alignment may be used. The Clustal W method of alignment (described by Higgins and Sharp, CABIOS. 5:151-153 (1989); Higgins, D. G. et al., *Comput. Appl. Biosci.* 8:189-191 (1992)) can be found in the MegAlign™ v6.1 program of the LASERGENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB. After alignment of the sequences using the Clustal W program, it is possible to obtain "percent identity" and "divergence" values by viewing the "sequence distances" table in the same program.

Embodiments of the Invention Include:

The present invention relates to terminator sequences. Recombinant DNA constructs comprising terminator sequences are provided.

An embodiment of this invention is an isolated polynucleotide sequence comprising (a) the sequence set forth in SEQ ID NO:1 or SEQ ID NO:18; (b) a sequence with at least 95% sequence identity to SEQ ID NO:1 or SEQ ID NO:18; or (c) a sequence comprising a functional fragment of (a) or (b), wherein the isolated polynucleotide sequence functions as a terminator in a plant cell. In another aspect, this invention concerns a recombinant DNA construct comprising a promoter, at least one heterologous nucleic acid fragment, and any terminator, or combination of terminator elements, of the present invention, wherein the promoter, at least one heterologous nucleic acid fragment, and terminator(s) are operably linked.

In another embodiment, a functional fragment may comprise at least 450, 425, 400, 375, 350, 325, 300, 275, 250, 225, 200, 175 or 150 contiguous nucleotides of SEQ ID NO:1 or SEQ ID NO:18.

Recombinant DNA constructs can be constructed by operably linking the nucleic acid fragment of the invention, the terminator sequences set forth in SEQ ID NO:1, or 18 or a functional fragment of the nucleotide sequence set forth in SEQ ID NO:1, or 18, to a heterologous nucleic acid fragment.

Another embodiment is a method for transforming a cell (or microorganism) comprising transforming a cell (or microorganism) with any of the isolated polynucleotides or recombinant DNA constructs of the present invention. The cell (or microorganism) transformed by this method is also included. In particular embodiments, the cell is eukaryotic cell, e.g., a yeast, insect or plant cell, or prokaryotic, e.g., a bacterial cell. The microorganism may be *Agrobacterium*, e.g. *Agrobacterium tumefaciens* or *Agrobacterium rhizogenes*.

Another embodiment of this invention is a method of expressing a heterologous polynucleotide in a plant, comprising the steps of introducing into a regenerable plant cell the recombinant DNA construct described above and regenerating a transgenic plant from the transformed regenerable plant cell, wherein the transgenic plant comprises the recombinant DNA construct and exhibits expression of the heterologous polynucleotide.

Another embodiment of this invention is a method of expressing a heterologous polynucleotide in a plant, comprising the steps of introducing into a regenerable plant cell the recombinant DNA construct described above; regenerating a transgenic plant from the regenerable plant cell described above; and obtaining a progeny plant from the transgenic plant, wherein the transgenic plant and the progeny plant comprises the recombinant DNA construct and exhibits expression of the heterologous polynucleotide.

In another embodiment, any of the methods of expressing a heterologous polynucleotide, wherein the plant cell is a monocotyledonous or dicotyledonous plant cell, for example, a maize or soybean plant cell. The plant cell may also be from sunflower, sorghum, canola, wheat, alfalfa, cotton, rice, barley, millet, sugar cane or switchgrass.

In another embodiment, this invention concerns a vector, virus, cell, microorganism, plant, or seed comprising a recombinant DNA construct comprising the terminator sequences described in the present invention.

The invention encompasses regenerated, mature and fertile transgenic plants comprising the recombinant DNA constructs described above, transgenic seeds produced therefrom, T1 and subsequent generations. The transgenic plant cells, tissues, plants, and seeds may comprise at least one recombinant DNA construct of interest.

In one embodiment, the plant (or seed derived from the plant) comprising the terminator sequences described in the present invention is a monocotyledonous or dicotyledonous plant, for example, a maize or soybean plant. The plant may also be sunflower, sorghum, canola, wheat, alfalfa, cotton, rice, barley, millet, sugar cane or switchgrass. The plant may be an inbred plant or a hybrid plant.

EXAMPLES

The present invention is further illustrated in the following Examples, in which parts and percentages are by weight and degrees are Celsius, unless otherwise stated. It should be understood that these examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Furthermore, various modifications of the invention in addition to those shown and described herein will be apparent to those skilled in the art from the foregoing description. Such modifications are also intended to fall within the scope of the appended claims.

Example 1

Amplification and Cloning of a *Sorghum bicolor* Gamma-Kafirin Terminator Sequence Primers (SEQ ID NOS:2 and 3) were designed for amplifying the terminator of gamma-Kafirin gene from *Sorghum bicolor* (SB-GKAF) based on the *Sorghum bicolor* genomic sequence database. The primer sequences are given below, the underlined region is not homologous with genomic template:

```
TMS2039 (forward primer; SEQ ID NO: 2):
CAGATCTGATATCGATGGGCCCACTAACTATCTATACTGTAATAATGTTG

TATAG

TMS2040 (reverse primer; SEQ ID NO: 3):
CGGACCGGGTGACCAAGCTTAAGCGAACATATGTCCCTC
```

Figure 2:
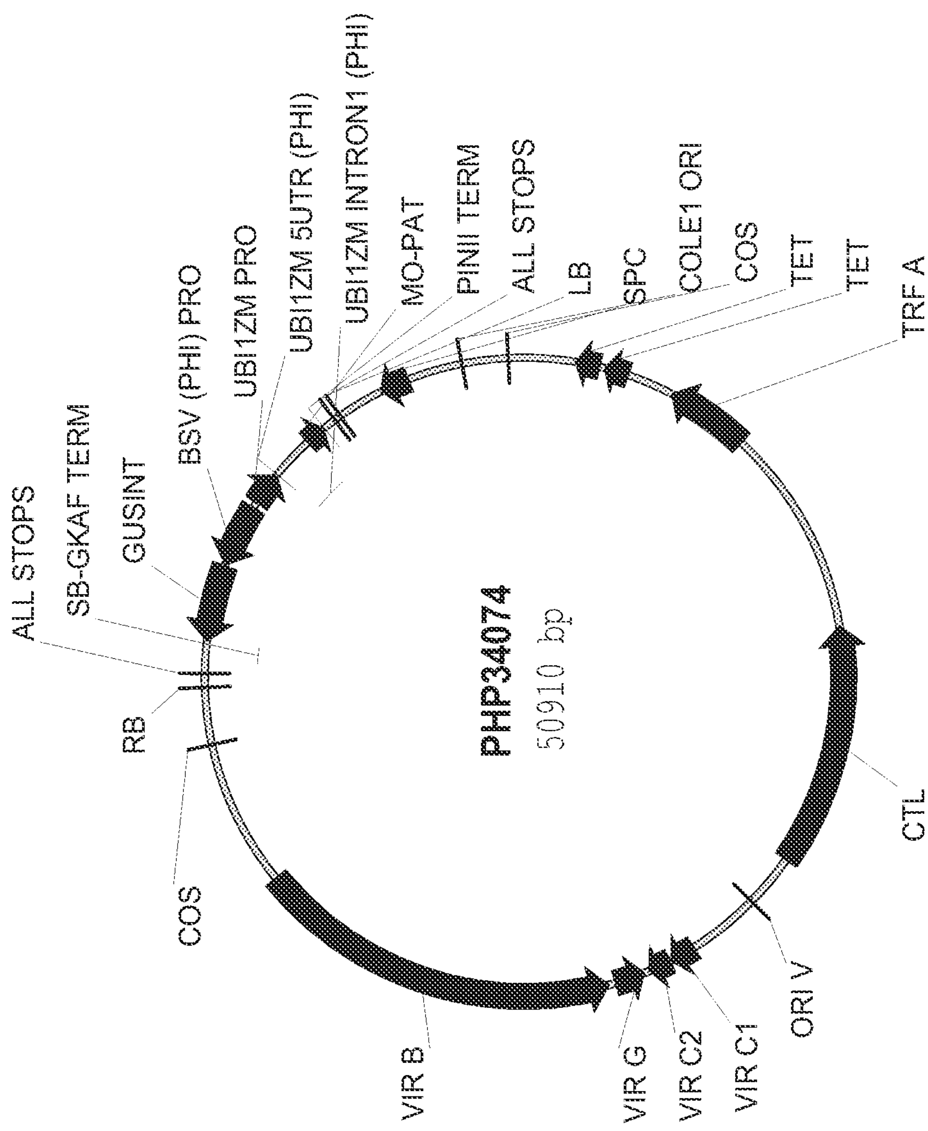
FIG. 2 shows the map of PHP34074, the vector used for testing the SB-GKAF terminator.

A 504 bp product comprising the 465 bp SB-GKAF terminator sequence (SEQ ID NO:1) was amplified by PCR using these primers. The product was cloned into pGEM-Teasy (Promega) (PHP31801; FIG. 1; SEQ ID NO:4) and the sequence was confirmed. The cloned SB-GKAF terminator included 165 bp of the predicted 3' UTR of SB-GKAF along with about 300 bp of downstream sequence. The amplified sequence of SB-GKAF terminator (SEQ ID NO:1) was then cloned into an *Agrobacterium* transformation vector (PHP34074; FIG. 2; SEQ ID NO:5), which had the following expression cassettes in divergent orientation:

SB-GKAF TERMINATOR: GUSINT: BSV PRO and

UBI-PRO:UBI INTRON:MOPAT:PINII TERM.

BSV PRO is Banana Streak Virus promoter, which is a strong constitutive promoter. A construct with a potato PINII terminator (Keil et al. (1986) *Nucleic Acids Res.* 14:5641-5650) in place of the SB-GKAF terminator was used as a control (PHP34005; SEQ ID NO:6).

Example 2

Transient Transformation to Test Efficacy of a SB-GKAF Terminator

Figure 3:
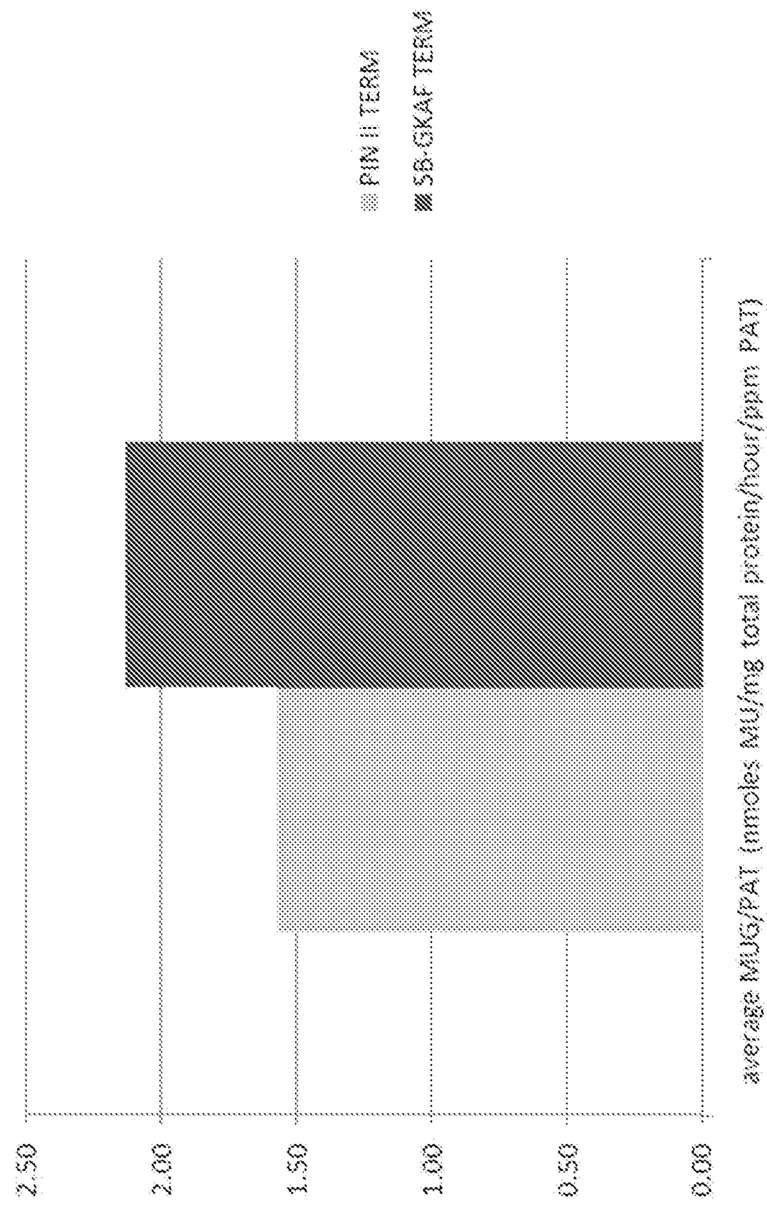
FIG. 3 shows the results of testing SB-GKAF terminator compared to PINII terminator in transient assays. It shows quantitative analysis of GUS reporter gene expression in BMS cells transformed with PHP34074 (SB-GKAF terminator) and PHP34005 (PINII terminator).

The isolated SB-GKAF terminator sequence (SEQ ID NO:1) was tested for its ability to act efficiently as a terminator in a recombinant construct. Its efficacy as a terminator was tested by its ability to stop transcription and by its ability to increase expression of a protein. Since improper termination can lead to improper processing of the 3' end of mRNA, and hence affect RNA stability, terminators have been found to affect protein expression levels. It has been shown that different terminators can cause up to 100-fold variation in the efficiency of transgene expression (Bieri et al, (2002) *Molecular Breeding* 10: 107-117; An et al (1989) *Plant Cell* 1: 115-122; Ingelbrecht et al (1989), *Plant Cell,* 1:671-680; Ali and Taylor (2001) *Plant Mol. Bio.,* 46:251-261). Hence we tested the SB-GKAF sequence (SEQ ID NO:1) for its ability to increase expression of a protein compared to the well-known PINII terminator. The *Agrobacterium* transformation vectors PHP34074 (SEQ ID NO:5) and PHP34005 (SEQ ID NO:6) described in Example 1 were used for transient transformation of BMS (Black Mexican Sweet) cells. The cells were harvested 5 days after transformation and sent for a quantification of the GUS activity (MUG assay). The SB-GKAF construct (PHP34074; SEQ ID NO:5) had ~35% more expression than that of the PINII construct (PHP34005, SEQ ID NO:6) when the GUS expression was normalized to the MOPAT expression (FIG. 3; Table 1). This information was indicative of the ability of the isolated SB-GKAF sequence (SEQ ID NO:1) to act efficiently as a terminator, by allowing protein expression equal to or above that of the PINII terminator.

TABLE 1

| Construct | Sequence Tested | Average MUG/PAT* | Standard Deviation |
|---|---|---|---|
| BSV PRO:GUSINT:PINII TERM | PIN II TERM | 1.57 | 0.17 |
| BSV PRO:GUSINT:SB-GKAF TERM | SB-GKAF TERM | 2.13 | 0.41 |

*Measured as: nmoles MU/mg total protein/hour/ppm PAT

Example 3

Stable Transformation Assays to Test SB-GKAF Terminator Activity

The *Agrobacterium* transformation vectors PHP34074 (SEQ ID NO:5) and PHP34005 (SEQ ID NO:6) described in Example 1, that were used for transient transformation assays as described in Example 2, were also used in Gaspe-Flint derived maize lines for stable transformation to generate transgenic maize plants.

Quantitative Reverse Transcriptase-PCR (qRT-PCR) and GUS assays were done from stably transformed plant tissues to test the ability of isolated SB-GKAF terminator sequence (SEQ ID NO:1) to stop transcription (that is prevent transcription read-through transcription) and to compare GUS expression as compared to that with PIN II terminator.

GUS Expression Analysis:

The expression of the GUS gene in the transgenic plants was assessed at the protein as well as transcript levels. To assess the expression at the protein level, MUG assay was performed on seedling leaf material. To assess the expression at the transcript level, qRT-PCR was done using primers shown in Table 2.

TABLE 2

| Primer/Probe | Type | Sequence | Fluor | qPCR Assay |
|---|---|---|---|---|
| GUS-1482F | Forward | SEQ ID NO: 7 | — | Taqman |
| GUS-1553R | Reverse | SEQ ID NO: 8 | — | Taqman |
| GUS-1509P | Probe | SEQ ID NO: 9 | FAM | Taqman |

Figure 4B:
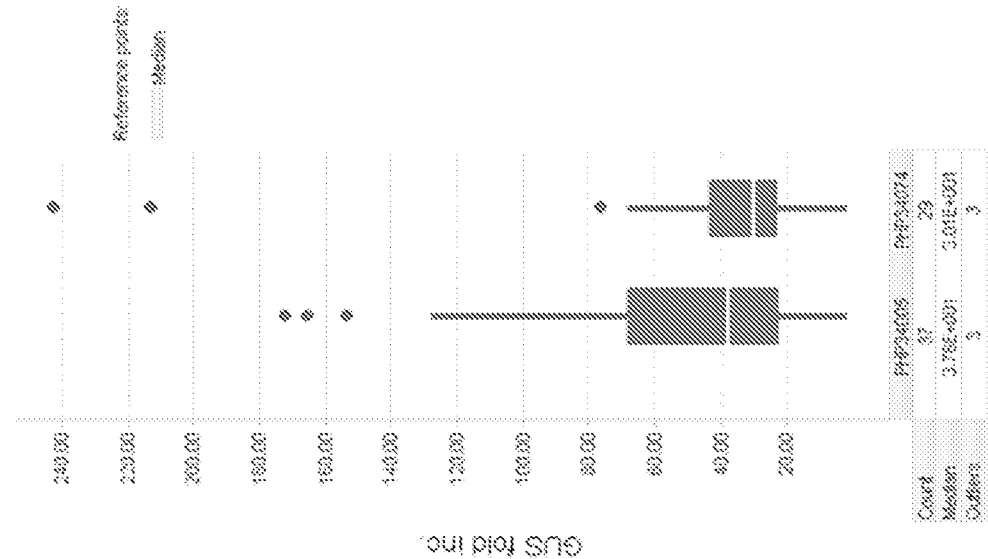
FIG. 4A and FIG. 4B show quantitative analysis of GUS reporter gene expression in Gaspe Flint derived maize lines stably transformed with SB-GKAF (PHP34074) and PINII (PHP34005) terminator constructs.
Figure 4A:
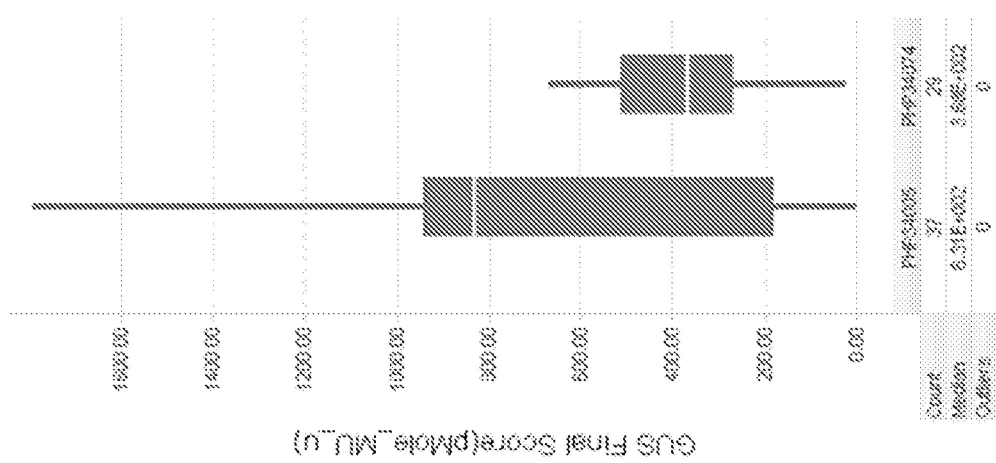

Plants were grown in the greenhouse and leaves were sampled at the R1 stage of development for expression analysis. Multiple plants were tested for each construct. Each plant was analyzed for expression of the GUS gene. GUS gene with the SB-GKAF terminator had GUS expression in the same range as that of PINII terminator at both the protein (FIG. 4A) and transcript (FIG. 4B) level.

Quantitative Reverse Transcriptase PCR (qRT-PCR) to Determine Read-Through Transcription Through the SB-GKAF Terminator:

The qRT-PCR assays were performed with leaf tissue from the stable transformants generated using PHP34074 and PHP34005. Each plant was tested for the presence of read-through transcript that had passed through the PINII terminator and the SB-GKAF terminator (SEQ ID NO:1). To assess presence of products that would indicate that transcription was continuing past the terminator, amplification was targeted downstream of the terminator being tested. Two primer sets were designed downstream of the tested terminators.

Primer set Term1 ~100 nt from the terminator

Primer set Term2.1 ~500 nt from the terminator

Multiple plants were tested for each construct. The primers are shown in Table 3.

TABLE 3

| Primer/ Probe | Name | Type | Sequence | Fluor | qPCR Assay |
|---|---|---|---|---|---|
| Term2.1[1] | Term2.1F | fwd | SEQ ID NO: 10 | — | SYBR |
| Term2.1[1] | Term2.1R | rev | SEQ ID NO: 11 | — | SYBR |
| Term1[1] | Term 1F | fwd | SEQ ID NO: 12 | — | Taqman |
| Term1[1] | Term 1R | rev | SEQ ID NO: 13 | — | Taqman |

TABLE 3-continued

| Primer/ Probe | Name | Type | Sequence | Fluor | qPCR Assay |
|---|---|---|---|---|---|
| Term1[1] | Term_1P | probe | SEQ ID NO: 14 | FAM | Taqman |
| Actin[2] | Actin_MGB_F | fwd | SEQ ID NO: 15 | — | Taqman |
| Actin[2] | Actin_MGB_R | rev | SEQ ID NO: 16 | — | Taqman |
| Actin[2] | Actin_VIC_P | probe | SEQ ID NO: 17 | VIC | Taqman |

[1]Post-Terminator Primer Set

[2]Reference Gene

The test plants were classified into 3 categories depending on the qRT-PCR results:

1. Plants showing complete termination: where all GUS transcripts are completely terminated before they reached the specific primer set location;
2. Plants showing a high degree of termination: where a large portion of the GUS transcripts are terminated before they reached the specific primer set location, also defined as:
   Primer set Term1—ΔCT>13
   Primer set Term2.1—ΔCT>9; and
3. Plants showing poor termination.

Figure 5:
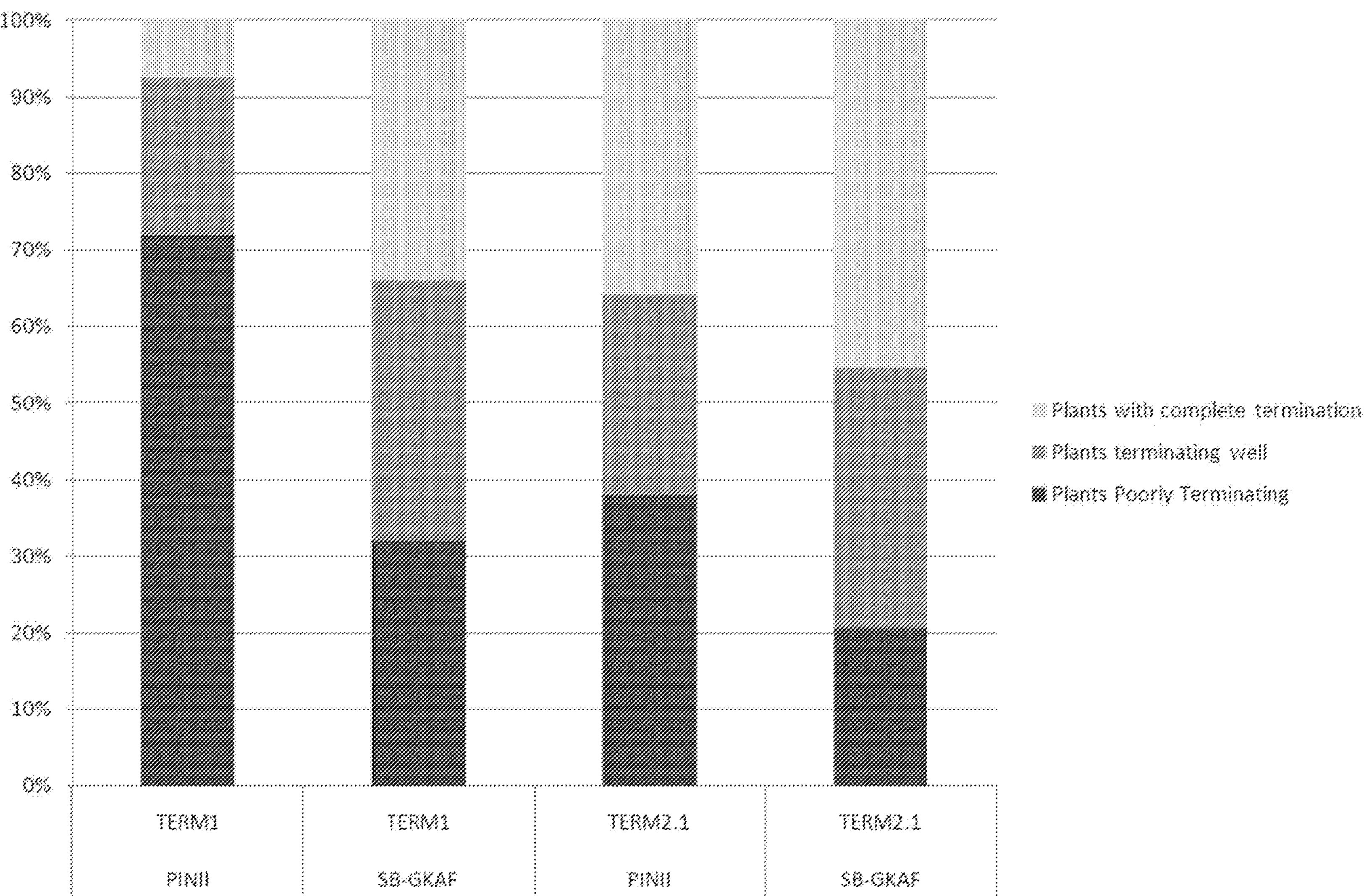
FIG. 5 shows the results of qRT-PCR assays with stably transformed Gaspe Flint derived maize lines, using two sets of primers downstream of the SB-GKAF terminator and the PINII terminator.

As can be see from FIG. 5, the SB-GKAF terminator proved to have fewer "poorly terminating" plants than the PINII terminator (FIG. 5). Thus the qRT-PCR score for presence of transcripts that had proceeded through the terminator was lower for the SB-GKAF terminator than that for the PINII terminator.

We claim:

1. A recombinant construct comprising a polynucleotide sequence operably linked to a heterologous polynucleotide sequence, wherein the polynucleotide sequence comprises:

(a) a nucleotide sequence comprising the sequence set forth in SEQ ID NO:18;

or (b) a nucleotide sequence comprising a fragment of at least 200 contiguous nucleotides of (a);

wherein the polynucleotide sequence functions as a transcriptional terminator in a plant cell.

2. The recombinant construct of claim 1 wherein the heterologous polynucleotide sequence is operably linked to a promoter.

3. A plant comprising the recombinant construct of claim 1.

4. The plant of claim 3 wherein the plant is a monocot.

5. The plant of claim 4 wherein the plant is a maize plant.

6. A seed comprising the recombinant construct of claim 1.

7. The seed of claim 6 wherein the seed is from a monocot plant.

8. The seed of claim 7 wherein the seed is from a maize plant.

9. A method of expressing a heterologous polynucleotide in a plant, comprising the steps of:

(a) introducing into a regenerable plant cell the recombinant construct of claim 2;

(b) regenerating a transgenic plant from the regenerable plant cell of step (a), wherein the transgenic plant comprises the recombinant construct of claim 2; and (c) obtaining a progeny plant from the transgenic plant of step (b), wherein the progeny plant comprises the recombinant construct of claim 2 and exhibits expression of the heterologous polynucleotide.

10. The method of claim 9, wherein the plant is a monocot plant.

11. The method of claim 10, wherein the plant is a maize plant.

12. A plant comprising the recombinant construct of claim 2.

13. The plant of claim 12 wherein the plant is a monocot.

14. The plant of claim 13 wherein the plant is a maize plant.

15. A seed comprising the recombinant construct of claim 2.

16. The seed of claim 15 wherein the seed is from a monocot plant.

17. The seed of claim 16 wherein the seed is from a maize plant.

* * * * *

SEQUENCE LISTING

```
<160> NUMBER OF SEQ ID NOS: 19

<210> SEQ ID NO 1
<211> LENGTH: 459
<212> TYPE: DNA
<213> ORGANISM: Sorghum bicolor

<400> SEQUENCE: 1

aactatctat actgtaataa tgttgtatag ccgccggata gctagctagt ttagtcattc      60

agcggcgatg ggtaataata aagtgtcatc catccatcac catgggtggc aacgtgagca     120

atgacctgat tgaacaaatt gaaatgaaaa gaagaaatat gttatatgtc aacgagattt     180

cctcataatg ccactgacaa cgtgtgtcca agaaatgtat cagtgatacg tatattcaca     240

atttttttat gacttatact cacaatttgt ttttttacta cttatactca caatttgttg     300

tgggtaccat aacaatttcg atcgaatata tatcagaaag ttgacgaaag taagctcact     360

caaaaagtta aatgggctgc ggaagctgcg tcaggcccaa gttttggcta ttctatccgg     420

tatccacgat tttgatggct gagggacata tgttcgctt                            459


<210> SEQ ID NO 2
<211> LENGTH: 55
<212> TYPE: DNA
<213> ORGANISM: Artificial Sequence
<220> FEATURE:
<223> OTHER INFORMATION: forward primer

<400> SEQUENCE: 2

cagatctgat atcgatgggc ccactaacta tctatactgt aataatgttg tatag           55


<210> SEQ ID NO 3
<211> LENGTH: 39
<212> TYPE: DNA
<213> ORGANISM: Artificial Sequence
```

```
<220> FEATURE:
<223> OTHER INFORMATION: Reverse primer

<400> SEQUENCE: 3

cggaccgggt gaccaagctt aagcgaacat atgtccctc                              39


<210> SEQ ID NO 4
<211> LENGTH: 3521
<212> TYPE: DNA
<213> ORGANISM: Artificial Sequence
<220> FEATURE:
<223> OTHER INFORMATION: Vector

<400> SEQUENCE: 4

gggcgaattg ggcccgacgt cgcatgctcc cggccgccat ggcggccgcg ggaattcgat      60

tcggaccggg tgaccaagct taagcgaaca tatgtccctc agccatcaaa atcgtggata     120

ccggatagaa tagccaaaac ttgggcctga cgcagcttcc gcagcccatt taactttttg     180

agtgagctta ctttcgtcaa ctttctgata tatattcgat cgaaattgtt atggtaccca     240

caacaaattg tgagtataag tagtaaaaaa acaaattgtg agtataagtc ataaaaaaat     300

tgtgaatata cgtatcactg atacatttct tggacacacg tcgtcagtgg cattatgagg     360

aaatctcgtt gacatataac atatttcttc ttttcatttc aatttgttca atcaggtcat     420

tgctcacgtt gccacccatg gtgatggatg gatgacactt tattattacc catcgccgct     480

gaatgactaa actagctagc tatccggcgg ctatacaaca ttattacagt atagatagtt     540

agtgggccca tcgatatcag atctgaatca ctagtgaatt cgcggccgcc tgcaggtcga     600

ccatatggga gagctcccaa cgcgttggat gcatagcttg agtattctat agtgtcacct     660

aaatagcttg gcgtaatcat ggtcatagct gtttcctgtg tgaaattgtt atccgctcac     720

aattccacac aacatacgag ccggaagcat aaagtgtaaa gcctggggtg cctaatgagt     780

gagctaactc acattaattg cgttgcgctc actgcccgct ttccagtcgg gaaacctgtc     840

gtgccagctg cattaatgaa tcggccaacg cgcggggaga ggcggtttgc gtattgggcg     900

ctcttccgct tcctcgctca ctgactcgct gcgctcggtc gttcggctgc ggcgagcggt     960

atcagctcac tcaaaggcgg taatacggtt atccacagaa tcaggggata acgcaggaaa    1020

gaacatgtga gcaaaaggcc agcaaaaggc caggaaccgt aaaaaggccg cgttgctggc    1080

gtttttccat aggctccgcc cccctgacga gcatcacaaa aatcgacgct caagtcagag    1140

gtggcgaaac ccgacaggac tataaagata ccaggcgttt ccccctggaa gctccctcgt    1200

gcgctctcct gttccgaccc tgccgcttac cggatacctg tccgcctttc tcccttcggg    1260

aagcgtggcg ctttctcata gctcacgctg taggtatctc agttcggtgt aggtcgttcg    1320

ctccaagctg ggctgtgtgc acgaaccccc cgttcagccc gaccgctgcg ccttatccgg    1380

taactatcgt cttgagtcca acccggtaag acacgactta tcgccactgg cagcagccac    1440

tggtaacagg attagcagag cgaggtatgt aggcggtgct acagagttct tgaagtggtg    1500

gcctaactac ggctacacta gaagaacagt atttggtatc tgcgctctgc tgaagccagt    1560

taccttcgga aaaagagttg gtagctcttg atccggcaaa caaaccaccg ctggtagcgg    1620

tggttttttt gtttgcaagc agcagattac gcgcagaaaa aaaggatctc aagaagatcc    1680

tttgatcttt tctacggggt ctgacgctca gtggaacgaa aactcacgtt aagggatttt    1740

ggtcatgaga ttatcaaaaa ggatcttcac ctagatcctt ttaaattaaa aatgaagttt    1800

taaatcaatc taaagtatat atgagtaaac ttggtctgac agttaccaat gcttaatcag    1860
```

```
tgaggcacct atctcagcga tctgtctatt tcgttcatcc atagttgcct gactccccgt   1920

cgtgtagata actacgatac gggagggctt accatctggc cccagtgctg caatgatacc   1980

gcgagaccca cgctcaccgg ctccagattt atcagcaata aaccagccag ccggaagggc   2040

cgagcgcaga agtggtcctg caactttatc cgcctccatc cagtctatta attgttgccg   2100

ggaagctaga gtaagtagtt cgccagttaa tagtttgcgc aacgttgttg ccattgctac   2160

aggcatcgtg gtgtcacgct cgtcgtttgg tatggcttca ttcagctccg gttcccaacg   2220

atcaaggcga gttacatgat cccccatgtt gtgcaaaaaa gcggttagct ccttcggtcc   2280

tccgatcgtt gtcagaagta agttggccgc agtgttatca ctcatggtta tggcagcact   2340

gcataattct cttactgtca tgccatccgt aagatgcttt tctgtgactg gtgagtactc   2400

aaccaagtca ttctgagaat agtgtatgcg gcgaccgagt tgctcttgcc cggcgtcaat   2460

acgggataat accgcgccac atagcagaac tttaaaagtg ctcatcattg gaaaacgttc   2520

ttcggggcga aaactctcaa ggatcttacc gctgttgaga tccagttcga tgtaacccac   2580

tcgtgcaccc aactgatctt cagcatcttt tactttcacc agcgtttctg ggtgagcaaa   2640

aacaggaagg caaaatgccg caaaaaaggg aataagggcg acacggaaat gttgaatact   2700

catactcttc ctttttcaat attattgaag catttatcag ggttattgtc tcatgagcgg   2760

atacatattt gaatgtattt agaaaaataa acaaataggg gttccgcgca catttccccg   2820

aaaagtgcca cctgatgcgg tgtgaaatac cgcacagatg cgtaaggaga aaataccgca   2880

tcaggaaatt gtaagcgtta atattttgtt aaaattcgcg ttaaattttt gttaaatcag   2940

ctcatttttt aaccaatagg ccgaaatcgg caaaatccct tataaatcaa aagaatagac   3000

cgagataggg ttgagtgttg ttccagtttg gaacaagagt ccactattaa agaacgtgga   3060

ctccaacgtc aaagggcgaa aaaccgtcta tcagggcgat ggcccactac gtgaaccatc   3120

accctaatca agtttttttgg ggtcgaggtg ccgtaaagca ctaaatcgga accctaaagg   3180

gagcccccga tttagagctt gacggggaaa gccggcgaac gtggcgagaa aggaagggaa   3240

gaaagcgaaa ggagcgggcg ctagggcgct ggcaagtgta gcggtcacgc tgcgcgtaac   3300

caccacaccc gccgcgctta atgcgccgct acagggcgcg tccattcgcc attcaggctg   3360

cgcaactgtt gggaagggcg atcggtgcgg gcctcttcgc tattacgcca gctggcgaaa   3420

gggggatgtg ctgcaaggcg attaagttgg gtaacgccag ggttttccca gtcacgacgt   3480

tgtaaaacga cggccagtga attgtaatac gactcactat a                      3521


<210> SEQ ID NO 5
<211> LENGTH: 50910
<212> TYPE: DNA
<213> ORGANISM: Artificial Sequence
<220> FEATURE:
<223> OTHER INFORMATION: SB-GKAF terminator construct

<400> SEQUENCE: 5

acgtgaccct agtcacttag gttaccagag ctggtcacct ttgtccacca agatggaact     60

gcggccgctc attaattaag tcaggcgcgc ctctagttga agacacgttc atgtcttcat    120

cgtaagaaga cactcagtag tcttcggcca gaatggccat ctggattcag caggcctaga    180

aggccattta aatcctgagg atctggtctt cctaaggacc cgggatatcg ctatcaactt    240

tgtatagaaa agttgggccg aattcgagct cggtacggcc agaatggccc ggaccgggtt    300

accgaattcg agctcggtac cactagtaag cttaagcgaa catatgtccc tcagccatca    360

aaatcgtgga taccggatag aatagccaaa acttgggcct gacgcagctt ccgcagccca    420
```

```
tttaactttt tgagtgagct tactttcgtc aactttctga tatatattcg atcgaaattg    480
ttatggtacc cacaacaaat tgtgagtata agtagtaaaa aaacaaattg tgagtataag    540
tcataaaaaa attgtgaata tacgtatcac tgatacattt cttggacaca cgtcgtcagt    600
ggcattatga ggaaatctcg ttgacatata acatatttct tcttttcatt tcaatttgtt    660
caatcaggtc attgctcacg ttgccaccca tggtgatgga tggatgacac tttattatta    720
cccatcgccg ctgaatgact aaactagcta gctatccggc ggctatacaa cattattaca    780
gtatagatag ttagtgggcc catcgatatc agatcttcat tgtttgcctc cctgctgcgg    840
tttttcaccg aagttcatgc cagtccagcg tttttgcagc agaaaagccg ccgacttcgg    900
tttgcggtcg cgagtgaaga tccctttctt gttaccgcca acgcgcaata tgccttgcga    960
ggtcgcaaaa tcggcgaaat tccatacctg ttcaccgacg acggcgctga cgcgatcaaa   1020
gacgcggtga tacatatcca gccatgcaca ctgatactct tcactccaca tgtcggtgta   1080
cattgagtgc agcccggcta acgtatccac gccgtattcg gtgatgataa tcggctgatg   1140
cagtttctcc tgccaggcca gaagttcttt ttccagtacc ttctctgccg tttccaaatc   1200
gccgctttgg acataccatc cgtaataacg gttcaggcac agcacatcaa agagatcgct   1260
aatggtatcg gtgtgagcgt cgcagaacat tacattgacg caggtgatcg gacgcgtcgg   1320
gtcgagttta cgcgttgctt ccgccagtgg cgcgaaatat tcccgtgcac cttgcggacg   1380
ggtatccggt tcgttggcaa tactccacat caccacgctt gggtggtttt tgtcacgcgc   1440
tatcagctct ttaatcgcct gtaagtgcgc ttgctgagtt tccccgttga ctgcctcttc   1500
gctgtacagt tctttcggct tgttgcccgc ttcgaaacca atccctaaag agaggttaaa   1560
gccgacagca gcagtttcat caatcaccac gatgccatgt tcatctgccc agtcgagcat   1620
ctcttcagcg taagggtaat gcgaggtacg gtaggagttg gccccaatcc agtccattaa   1680
tgcgtggtcg tgcaccatca gcacgttatc gaatcctttg ccacgcaagt ccgcatcttc   1740
atgacgacca aagccagtaa agtagaacgg tttgtggtta atcaggaact gttggccctt   1800
cactgccact gaccggatgc cgacgcgaag cgggtagata tcacactctg tctggctttt   1860
ggctgtgacg cacagttcat agagataacc ttcacccggt tgccagaggt gcggattcac   1920
cacttgcaaa gtcccgctag tgccttgtcc agttgcaacc acctgttgat ccgcatcacg   1980
cagttcaacg ctgacatcac cattggccac cacctgccag tcaacagacg cgtggttaca   2040
gtcttgcgcg acatgcgtca ccacggtgat atcgtccacc caggtgttcg gcgtggtgta   2100
gagcattacg ctgcgatgga ttccggcata gttaaagaaa tcatggaagt aagactgctt   2160
tttcttgccg ttttcgtcgg taatcaccat tcccggcggg atagtctgcc agttcagttc   2220
gttgttcaca caaacggtga tacctgcaca tcaacaaatt ttggtcatat attagaaaag   2280
ttataaatta aaatatacac acttataaac tacagaaaag caattgctat atactacatt   2340
cttttatttt gaaaaaaata tttgaaatat tatattacta ctaattaatg ataattatta   2400
tatatatatc aaaggtagaa gcagaaactt acgtacactt ttcccggcaa taacatacgg   2460
cgtgacatcg gcttcaaatg gcgtatagcc gccctgatgc tccatcactt cctgattatt   2520
gacccacact ttgccgtaat gagtgaccgc atcgaaacgc agcacgatac gctggcctgc   2580
ccaacctttc ggtataaaga cttcgcgctg ataccagacg ttgcccgcat aattacgaat   2640
atctgcatcg gcgaactgat cgttaaaact gcctggcaca gcaattgccc ggctttcttg   2700
taacgcgctt tcccaccaac gctgatcaat tccacagttt tcgcgatcca gactgaatgc   2760
ccacaggccg tcgagttttt tgatttcacg ggttggggtt tctacaggac ggaccatggt   2820
```

```
gtcgtgtgga tccaaattgt atgcaaggtg aatgactttc ttttcgtaaa ctagatagga   2880
gtactcctcc aggatgctta acccgtattg acgtacagag gtctatgatc cttttgttta   2940
taaaggagct tgtagttcag tcagtcttat acttcacgat gcccatgttt ctatatagga   3000
tattatcttg gctttgtaag tacttcacgc aggttatgtt ctgtttctag gatattatcc   3060
tcatacatgc gaagaaccaa tttttccccc attctcttcg ggtacttttt cttgggtagg   3120
catgctctct tggaccaact agcataaaac ataatcattt ttccctacag ccttgaccag   3180
ctataatcga aatcatgctc atttttctaa gaaagactga atacagctcc aatttaaaca   3240
atttaaatca taaacttgta actcaattag agaaaagcag agcccttcgg ctcctatcta   3300
aaggaattac cccatgaaag ccataaaaac gaaccttgct ctgataccag acgggtctac   3360
gctcgcggaa ctaggatctt gcgctctact cgcacaaagt gaactcgcac aaagtgtgtt   3420
tcaagcacag aagtttttat ttctcaaatc aggagtaaac tcgcgttgtg gtgcgtgttt   3480
gcaacctgaa tacaaggctc cttatataga gagttgtgga gctttctggc atcgttaggt   3540
ggcatccacc aataatgcag ataagcatca tcacatgtct ctggcctaac aactttgcgt   3600
aagaatcctg caaagttact aaaggtcatc gtgcgtgact agacaacgca caccgacaaa   3660
cttaaaataa agagacatta tactttgtct cctctttaca taaagtgagt ggtatccagc   3720
tcactccgca tcttatcagt cttcacaccg gttggtatca acacgtggta ggggtccgcc   3780
acttccgctt cagtcatcat tactgatatc cagcagatct agagcatctt caataagata   3840
ttcttgttct gcacgcagat ttcttgctc cctcagtaat tcctcccaca gtgagtcttc   3900
tgatatttct tcaagtttct tctcccatct gatcttttcc tgcacaaacg agtcaatttg   3960
gtctttccag acccaagtaa aacaagtgtt agtttcacag gagtaaaact ccctgtcagg   4020
atttctggat gttctggaga tcttcagttt tgctggttta ttgcatccac atttgaaaac   4080
cggctcttca cttagtgtta gcacattgat ttgatgcaac ctgtagcctt tgctcaacca   4140
gtcttcatat ctttttacaa catcattaac tctctgtttt gcatcggtgt ttcccttgtg   4200
aaatacctcc tccactgcat tgatcaacac accttcagat tgatgctttt ccggatggag   4260
aataatcttt accagtcttg acagagtgtc tgctaaaacg ttgtcctttc cgtcaatgtg   4320
ttcaaactta atctcaagac ctgtcccggt aatgtaatct gtgaaggcaa gccatctgac   4380
tcttgatggt ttatgatcac tgcttttctt gtaaaagctc actattgctt gactgtcagt   4440
tctgattatg agctctttgt aagcttggtc acccggtccg ggcctagaag gccagcttcg   4500
gccgccccgg gcaactttat tatacaaagt tgatagatat cggaccgatt aaactttaat   4560
tcggtccgaa gcttgcatgc ctgcagtgca gcgtgacccg gtcgtgcccc tctctagaga   4620
taatgagcat tgcatgtcta agttataaaa aattaccaca tatttttttt gtcacacttg   4680
tttgaagtgc agtttatcta tctttataca tatatttaaa ctttactcta cgaataatat   4740
aatctatagt actacaataa tatcagtgtt ttagagaatc atataaatga acagttagac   4800
atggtctaaa ggacaattga gtattttgac aacaggactc tacagtttta tctttttagt   4860
gtgcatgtgt tctccttttt ttttgcaaat agcttcacct atataatact tcatccattt   4920
tattagtaca tccatttagg gtttagggtt aatggttttt atagactaat ttttttagta   4980
catctatttt attctatttt agcctctaaa ttaagaaaac taaaactcta ttttagtttt   5040
tttatttaat aatttagata taaaatagaa taaaataaag tgactaaaaa ttaaacaaat   5100
accctttaag aaattaaaaa aactaaggaa acattttttct tgtttcgagt agataatgcc   5160
agcctgttaa acgccgtcga cgagtctaac ggacaccaac cagcgaacca gcagcgtcgc   5220
```

-continued

```
gtcgggccaa gcgaagcaga cggcacggca tctctgtcgc tgcctctgga cccctctcga   5280
gagttccgct ccaccgttgg acttgctccg ctgtcggcat ccagaaattg cgtggcggag   5340
cggcagacgt gagccggcac ggcaggcggc ctcctcctcc tctcacggca ccggcagcta   5400
cgggggattc ctttcccacc gctccttcgc tttcccttcc tcgcccgccg taataaatag   5460
acaccccctc cacaccctct ttccccaacc tcgtgttgtt cggagcgcac acacacacaa   5520
ccagatctcc cccaaatcca cccgtcggca cctccgcttc aaggtacgcc gctcgtcctc   5580
cccccccccc ctctctacct tctctagatc ggcgttccgg tccatgcatg gttagggccc   5640
ggtagttcta cttctgttca tgtttgtgtt agatccgtgt ttgtgttaga tccgtgctgc   5700
tagcgttcgt acacggatgc gacctgtacg tcagacacgt tctgattgct aacttgccag   5760
tgtttctctt tggggaatcc tgggatggct ctagccgttc cgcagacggg atcgatttca   5820
tgattttttt tgtttcgttg catagggttt ggtttgccct tttcctttat ttcaatatat   5880
gccgtgcact tgtttgtcgg gtcatctttt catgcttttt tttgtcttgg ttgtgatgat   5940
gtggtctggt tgggcggtcg ttctagatcg gagtagaatt ctgtttcaaa ctacctggtg   6000
gatttattaa ttttggatct gtatgtgtgt gccatacata ttcatagtta cgaattgaag   6060
atgatggatg gaaatatcga tctaggatag gtatacatgt tgatgcgggt tttactgatg   6120
catatacaga gatgcttttt gttcgcttgg ttgtgatgat gtggtgtggt tgggcggtcg   6180
ttcattcgtt ctagatcgga gtagaatact gtttcaaact acctggtgta tttattaatt   6240
ttggaactgt atgtgtgtgt catacatctt catagttacg agtttaagat ggatggaaat   6300
atcgatctag gataggtata catgttgatg tgggttttac tgatgcatat acatgatggc   6360
atatgcagca tctattcata tgctctaacc ttgagtacct atctattata ataaacaagt   6420
atgttttata attattttga tcttgatata cttggatgat ggcatatgca gcagctatat   6480
gtggattttt ttagccctgc cttcatacgc tatttatttg cttggtactg tttcttttgt   6540
cgatgctcac cctgttgttt ggtgttactt ctgcaggtcg actttaactt agcctaggat   6600
ccacacgaca ccatgtcccc cgagcgccgc cccgtcgaga tccgcccggc caccgccgcc   6660
gacatggccg ccgtgtgcga catcgtgaac cactacatcg agacctccac cgtgaacttc   6720
cgcaccgagc cgcagacccc gcaggagtgg atcgacgacc tggagcgcct ccaggaccgc   6780
tacccgtggc tcgtggccga ggtggagggc gtggtggccg gcatcgccta cgccggcccg   6840
tggaaggccc gcaacgccta cgactggacc gtggagtcca ccgtgtacgt gtcccaccgc   6900
caccagcgcc tcggcctcgg ctccaccctc tacacccacc tcctcaagag catggaggcc   6960
cagggcttca agtccgtggt ggccgtgatc ggcctcccga acgacccgtc cgtgcgcctc   7020
cacgaggccc tcggctacac cgcccgcggc accctccgcg ccgccggcta caagcacggc   7080
ggctggcacg acgtcggctt ctggcagcgc gacttcgagc tgccggcccc gccgcgcccg   7140
gtgcgcccgg tgacgcagat ctgagtcgaa acctagactt gtccatcttc tggattggcc   7200
aacttaatta atgtatgaaa taaaaggatg cacacatagt gacatgctaa tcactataat   7260
gtgggcatca aagttgtgtg ttatgtgtaa ttactagtta tctgaataaa agagaaagag   7320
atcatccata tttcttatcc taaatgaatg tcacgtgtct ttataattct ttgatgaacc   7380
agatgcattt cattaaccaa atccatatac atataaatat taatcatata taattaatat   7440
caattgggtt agcaaaacaa atctagtcta ggtgtgtttt gcgaatgcgg ccgataagtg   7500
actagggtca cgtgacccta gtcacttagg taccgagctc gaattcattc cgattaatcg   7560
tggcctcttg ctcttcagga tgaagagcta tgtttaaacg tgcaagcgct actagacaat   7620
```

```
tcagtacatt aaaaacgtcc gcaatgtgtt attaagttgt ctaagcgtca atttgtttac   7680
accacaatat atcctgccac cagccagcca acagctcccc gaccggcagc tcggcacaaa   7740
atcaccactc gatacaggca gcccatcagt ccgggacggc gtcagcggga gagccgttgt   7800
aaggcggcag actttgctca tgttaccgat gctattcgga agaacggcaa ctaagctgcc   7860
gggtttgaaa cacggatgat ctcgcggagg gtagcatgtt gattgtaacg atgacagagc   7920
gttgctgcct gtgatcaaat atcatctccc tcgcagagat ccgaattatc agccttctta   7980
ttcatttctc gcttaaccgt gacaggctgt cgatcttgag aactatgccg acataatagg   8040
aaatcgctgg ataaagccgc tgaggaagct gagtggcgct atttctttag aagtgaacgt   8100
tgacgatcgt cgaccgtacc ccgatgaatt aattcggacg tacgttctga acacagctgg   8160
atacttactt gggcgattgt catacatgac atcaacaatg tacccgtttg tgtaaccgtc   8220
tcttggaggt tcgtatgaca ctagtggttc ccctcagctt gcgactagat gttgaggcct   8280
aacattttat tagagagcag gctagttgct tagatacatg atcttcaggc cgttatctgt   8340
cagggcaagc gaaaattggc catttatgac gaccaatgcc ccgcagaagc tcccatcttt   8400
gccgccatag acgccgcgcc cccttttgg ggtgtagaac atccttttgc cagatgtgga   8460
aaagaagttc gttgtcccat tgttggcaat gacgtagtag ccggcgaaag tgcgagaccc   8520
atttgcgcta tatataagcc tacgatttcc gttgcgacta ttgtcgtaat tggatgaact   8580
attatcgtag ttgctctcag agttgtcgta atttgatgga ctattgtcgt aattgcttat   8640
ggagttgtcg tagttgcttg gagaaatgtc gtagttggat ggggagtagt catagggaag   8700
acgagcttca tccactaaaa caattggcag gtcagcaagt gcctgccccg atgccatcgc   8760
aagtacgagg cttagaacca ccttcaacag atcgcgcata gtcttcccca gctctctaac   8820
gcttgagtta agccgcgccg cgaagcggcg tcggcttgaa cgaattgtta gacattattt   8880
gccgactacc ttggtgatct cgcctttcac gtagtgaaca aattcttcca actgatctgc   8940
gcgcgaggcc aagcgatctt cttgtccaag ataagcctgc ctagcttcaa gtatgacggg   9000
ctgatactgg gccggcaggc gctccattgc ccagtcggca gcgacatcct tcggcgcgat   9060
tttgccggtt actgcgctgt accaaatgcg ggacaacgta agcactacat ttcgctcatc   9120
gccagcccag tcgggcggcg agttccatag cgttaaggtt tcatttagcg cctcaaatag   9180
atcctgttca ggaaccggat caaagagttc ctccgccgct ggacctacca aggcaacgct   9240
atgttctctt gcttttgtca gcaagatagc cagatcaatg tcgatcgtgg ctggctcgaa   9300
gatacctgca agaatgtcat tgcgctgcca ttctccaaat tgcagttcgc gcttagctgg   9360
ataacgccac ggaatgatgt cgtcgtgcac aacaatggtg acttctacag cgcggagaat   9420
ctcgctctct ccaggggaag ccgaagtttc caaaaggtcg ttgatcaaag ctcgccgcgt   9480
tgtttcatca agccttacag tcaccgtaac cagcaaatca atatcactgt gtggcttcag   9540
gccgccatcc actgcggagc cgtacaaatg tacggccagc aacgtcggtt cgagatggcg   9600
ctcgatgacg ccaactacct ctgatagttg agtcgatact tcggcgatca ccgcttccct   9660
catgatgttt aactcctgaa ttaagccgcg ccgcgaagcg gtgtcggctt gaatgaattg   9720
ttaggcgtca tcctgtgctc ccgagaacca gtaccagtac atcgctgttt cgttcgagac   9780
ttgaggtcta gttttatacg tgaacaggtc aatgccgccg agagtaaagc cacattttgc   9840
gtacaaattg caggcaggta cattgttcgt ttgtgtctct aatcgtatgc caaggagctg   9900
tctgcttagt gcccactttt tcgcaaattc gatgagactg tgcgcgactc ctttgcctcg   9960
```

-continued

```
gtgcgtgtgc gacacaacaa tgtgttcgat agaggctaga tcgttccatg ttgagttgag  10020
ttcaatcttc ccgacaagct cttggtcgat gaatgcgcca tagcaagcag agtcttcatc  10080
agagtcatca tccgagatgt aatccttccg gtaggggctc acacttctgg tagatagttc  10140
aaagccttgg tcggataggt gcacatcgaa cacttcacga acaatgaaat ggttctcagc  10200
atccaatgtt tccgccacct gctcagggat caccgaaatc ttcatatgac gcctaacgcc  10260
tggcacagcg gatcgcaaac ctggcgcggc ttttggcaca aaaggcgtga caggtttgcg  10320
aatccgttgc tgccacttgt taaccctttt gccagatttg gtaactataa tttatgttag  10380
aggcgaagtc ttgggtaaaa actggcctaa aattgctggg gatttcagga aagtaaacat  10440
caccttccgg ctcgatgtct attgtagata tatgtagtgt atctacttga tcgggggatc  10500
tgctgcctcg cgcgtttcgg tgatgacggt gaaaacctct gacacatgca gctcccggag  10560
acggtcacag cttgtctgta agcggatgcc gggagcagac aagcccgtca gggcgcgtca  10620
gcgggtgttg gcgggtgtcg gggcgcagcc atgacccagt cacgtagcga tagcggagtg  10680
tatactggct taactatgcg gcatcagagc agattgtact gagagtgcac catatgcggt  10740
gtgaaatacc gcacagatgc gtaaggagaa aataccgcat caggcgctct tccgcttcct  10800
cgctcactga ctcgctgcgc tcggtcgttc ggctgcggcg agcggtatca gctcactcaa  10860
aggcggtaat acggttatcc acagaatcag gggataacgc aggaaagaac atgtgagcaa  10920
aaggccagca aaaggccagg aaccgtaaaa aggccgcgtt gctggcgttt ttccataggc  10980
tccgcccccc tgacgagcat cacaaaaatc gacgctcaag tcagaggtgg cgaaacccga  11040
caggactata aagataccag gcgtttcccc ctggaagctc cctcgtgcgc tctcctgttc  11100
cgaccctgcc gcttaccgga tacctgtccg cctttctccc ttcgggaagc gtggcgcttt  11160
ctcatagctc acgctgtagg tatctcagtt cggtgtaggt cgttcgctcc aagctgggct  11220
gtgtgcacga accccccgtt cagcccgacc gctgcgcctt atccggtaac tatcgtcttg  11280
agtccaaccc ggtaagacac gacttatcgc cactggcagc agccactggt aacaggatta  11340
gcagagcgag gtatgtaggc ggtgctacag agttcttgaa gtggtggcct aactacggct  11400
acactagaag gacagtattt ggtatctgcg ctctgctgaa gccagttacc ttcggaaaaa  11460
gagttggtag ctcttgatcc ggcaaacaaa ccaccgctgg tagcggtggt ttttttgttt  11520
gcaagcagca gattacgcgc agaaaaaaag gatctcaaga agatcctttg atcttttcta  11580
cggggtctga cgctcagtgg aacgaaaact cacgttaagg gattttggtc atgagattat  11640
caaaaaggat cttcacctag atccttttaa attaaaaatg aagttttaaa tcaatctaaa  11700
gtatatatga gtaaacttgg tctgacagtt accaatgctt aatcagtgag gcacctatct  11760
cagcgatctg tctatttcgt tcatccatag ttgcctgact ccccgtcgtg tagataacta  11820
cgatacggga gggcttacca tctggcccca gtgctgcaat gataccgcga gacccacgct  11880
caccggctcc agatttatca gcaataaacc agccagccgg aagggccgag cgcagaagtg  11940
gtcctgcaac tttatccgcc tccatccagt ctattaattg ttgccgggaa gctagagtaa  12000
gtagttcgcc agttaatagt ttgcgcaacg ttgttgccat tgctgcaggg gggggggggg  12060
gggggttcca ttgttcattc cacggacaaa aacagagaaa ggaaacgaca gaggccaaaa  12120
agctcgcttt cagcacctgt cgtttccttt cttttcagag ggtattttaa ataaaaacat  12180
taagttatga cgaagaagaa cggaaacgcc ttaaaccgga aaattttcat aaatagcgaa  12240
aacccgcgag gtcgccgccc cgtaacctgt cggatcaccg gaaaggaccc gtaaagtgat  12300
aatgattatc atctacatat cacaacgtgc gtggaggcca tcaaaccacg tcaaataatc  12360
```

```
aattatgacg caggtatcgt attaattgat ctgcatcaac ttaacgtaaa aacaacttca  12420
gacaatacaa atcagcgaca ctgaatacgg ggcaacctca tgtccccccc cccccccccc  12480
ctgcaggcat cgtggtgtca cgctcgtcgt ttggtatggc ttcattcagc tccggttccc  12540
aacgatcaag gcgagttaca tgatccccca tgttgtgcaa aaaagcggtt agctccttcg  12600
gtcctccgat cgttgtcaga agtaagttgg ccgcagtgtt atcactcatg gttatggcag  12660
cactgcataa ttctcttact gtcatgccat ccgtaagatg cttttctgtg actggtgagt  12720
actcaaccaa gtcattctga gaatagtgta tgcggcgacc gagttgctct tgcccggcgt  12780
caacacggga taataccgcg ccacatagca gaactttaaa agtgctcatc attggaaaac  12840
gttcttcggg gcgaaaactc tcaaggatct taccgctgtt gagatccagt tcgatgtaac  12900
ccactcgtgc acccaactga tcttcagcat cttttacttt caccagcgtt tctgggtgag  12960
caaaaacagg aaggcaaaat gccgcaaaaa agggaataag ggcgacacgg aaatgttgaa  13020
tactcatact cttccttttt caatattatt gaagcattta tcagggttat tgtctcatga  13080
gcggatacat atttgaatgt atttagaaaa ataaacaaat aggggttccg cgcacatttc  13140
cccgaaaagt gccacctgac gtctaagaaa ccattattat catgacatta acctataaaa  13200
ataggcgtat cacgaggccc tttcgtcttc aagaattcgg agcttttgcc attctcaccg  13260
gattcagtcg tcactcatgg tgatttctca cttgataacc ttatttttga cgaggggaaa  13320
ttaataggtt gtattgatgt tggacgagtc ggaatcgcag accgatacca ggatcttgcc  13380
atcctatgga actgcctcgg tgagttttct ccttcattac agaaacggct tttcaaaaa   13440
tatggtattg ataatcctga tatgaataaa ttgcagtttc atttgatgct cgatgagttt  13500
ttctaatcag aattggttaa ttggttgtaa cactggcaga gcattacgct gacttgacgg  13560
gacggcggct ttgttgaata aatcgaactt ttgctgagtt gaaggatcag atcacgcatc  13620
ttcccgacaa cgcagaccgt tccgtggcaa agcaaaagtt caaaatcacc aactggtcca  13680
cctacaacaa agctctcatc aaccgtggct ccctcacttt ctggctggat gatggggcga  13740
ttcaggcctg gtatgagtca gcaacacctt cttcacgagg cagacctcag cgccagaagg  13800
ccgccagaga ggccgagcgc ggccgtgagg cttggacgct agggcagggc atgaaaaagc  13860
ccgtagcggg ctgctacggg cgtctgacgc ggtggaaagg gggaggggat gttgtctaca  13920
tggctctgct gtagtgagtg ggttgcgctc cggcagcggt cctgatcaat cgtcaccctt  13980
tctcggtcct tcaacgttcc tgacaacgag cctccttttc gccaatccat cgacaatcac  14040
cgcgagtccc tgctcgaacg ctgcgtccgg accggcttcg tcgaaggcgt ctatcgcggc  14100
ccgcaacagc ggcgagagcg gagcctgttc aacggtgccg ccgcgctcgc cggcatcgct  14160
gtcgccggcc tgctcctcaa gcacggcccc aacagtgaag tagctgattg tcatcagcgc  14220
attgacggcg tccccggccg aaaaacccgc ctcgcagagg aagcgaagct gcgcgtcggc  14280
cgtttccatc tgcggtgcgc ccggtcgcgt gccggcatgg atgcgcgcgc catcgcggta  14340
ggcgagcagc gcctgcctga agctgcgggc attcccgatc agaaatgagc gccagtcgtc  14400
gtcggctctc ggcaccgaat gcgtatgatt ctccgccagc atggcttcgg ccagtgcgtc  14460
gagcagcgcc cgcttgttcc tgaagtgcca gtaaagcgcc ggctgctgaa cccccaaccg  14520
ttccgccagt ttgcgtgtcg tcagaccgtc tacgccgacc tcgttcaaca ggtccagggc  14580
ggcacggatc actgtattcg gctgcaactt tgtcatgctt gacactttat cactgataaa  14640
cataatatgt ccaccaactt atcagtgata aagaatccgc gcgttcaatc ggaccagcgg  14700
```

```
aggctggtcc ggaggccaga cgtgaaaccc aacataccc tgatcgtaat tctgagcact  14760
gtcgcgctcg acgctgtcgg catcggcctg attatgccgg tgctgccggg cctcctgcgc  14820
gatctggttc actcgaacga cgtcaccgcc cactatggca ttctgctggc gctgtatgcg  14880
ttggtgcaat ttgcctgcgc acctgtgctg ggcgcgctgt cggatcgttt cgggcggcgg  14940
ccaatcttgc tcgtctcgct ggccggcgcc actgtcgact acgccatcat ggcgacagcg  15000
cctttccttt gggttctcta tatcgggcgg atcgtggccg gcatcaccgg ggcgactggg  15060
gcggtagccg gcgcttatat tgccgatatc actgatggcg atgagcgcgc gcggcacttc  15120
ggcttcatga gcgcctgttt cgggttcggg atggtcgcgg gacctgtgct cggtgggctg  15180
atgggcggtt tctcccccca cgctccgttc ttcgccgcgg cagccttgaa cggcctcaat  15240
ttcctgacgg gctgtttcct tttgccggag tcgcacaaag gcgaacgccg gccgttacgc  15300
cgggaggctc tcaacccgct cgcttcgttc cggtgggccc ggggcatgac cgtcgtcgcc  15360
gccctgatgg cggtcttctt catcatgcaa cttgtcggac aggtgccggc cgcgctttgg  15420
gtcattttcg gcgaggatcg ctttcactgg gacgcgacca cgatcggcat ttcgcttgcc  15480
gcatttggca ttctgcattc actcgcccag gcaatgatca ccggccctgt agccgcccgg  15540
ctcggcgaaa ggcgggcact catgctcgga atgattgccg acggcacagg ctacatcctg  15600
cttgccttcg cgacacgggg atggatggcg ttcccgatca tggtcctgct tgcttcgggt  15660
ggcatcggaa tgccggcgct gcaagcaatg ttgtccaggc aggtggatga ggaacgtcag  15720
gggcagctgc aaggctcact ggcggcgctc accagcctga cctcgatcgt cggacccctc  15780
ctcttcacgg cgatctatgc ggcttctata acaacgtgga acgggtgggc atggattgca  15840
ggcgctgccc tctacttgct ctgcctgccg gcgctgcgtc gcgggctttg gagcggcgca  15900
gggcaacgag ccgatcgctg atcgtggaaa cgataggcct atgccatgcg ggtcaaggcg  15960
acttccggca agctatacgc gccctaggag tgcggttgga acgttggccc agccagatac  16020
tcccgatcac gagcaggacg ccgatgattt gaagcgcact cagcgtctga tccaagaaca  16080
accatcctag caacacggcg gtccccgggc tgagaaagcc cagtaaggaa acaactgtag  16140
gttcgagtcg cgagatcccc cggaaccaaa ggaagtaggt taaacccgct ccgatcaggc  16200
cgagccacgc caggccgaga acattggttc ctgtaggcat cgggattggc ggatcaaaca  16260
ctaaagctac tggaacgagc agaagtcctc cggccgccag ttgccaggcg gtaaaggtga  16320
gcagaggcac gggaggttgc cacttgcggg tcagcacggt tccgaacgcc atggaaaccg  16380
cccccgccag gcccgctgcg acgccgacag gatctagcgc tgcgtttggt gtcaacacca  16440
acagcgccac gcccgcagtt ccgcaaatag cccccaggac cgccatcaat cgtatcgggc  16500
tacctagcag agcggcagag atgaacacga ccatcagcgg ctgcacagcg cctaccgtcg  16560
ccgcgacccc gcccggcagg cggtagaccg aaataaacaa caagctccag aatagcgaaa  16620
tattaagtgc gccgaggatg aagatgcgca tccaccagat tcccgttgga atctgtcgga  16680
cgatcatcac gagcaataaa cccgccggca acgcccgcag cagcataccg gcgacccctc  16740
ggcctcgctg ttcgggctcc acgaaaacgc cggacagatg cgccttgtga gcgtccttgg  16800
ggccgtcctc ctgtttgaag accgacagcc caatgatctc gccgtcgatg taggcgccga  16860
atgccacggc atctcgcaac cgttcagcga acgcctccat gggctttttc tcctcgtgct  16920
cgtaaacgga cccgaacatc tctggagctt tcttcagggc cgacaatcgg atctcgcgga  16980
aatcctgcac gtcggccgct ccaagccgtc gaatctgagc cttaatcaca attgtcaatt  17040
ttaatcctct gtttatcggc agttcgtaga gcgcgccgtg cgtcccgagc gatactgagc  17100
```

```
gaagcaagtg cgtcgagcag tgcccgcttg ttcctgaaat gccagtaaag cgctggctgc  17160
tgaaccccca gccggaactg accccacaag gccctagcgt ttgcaatgca ccaggtcatc  17220
attgacccag gcgtgttcca ccaggccgct gcctcgcaac tcttcgcagg cttcgccgac  17280
ctgctcgcgc cacttcttca cgcgggtgga atccgatccg cacatgaggc ggaaggtttc  17340
cagcttgagc gggtacggct cccggtgcga gctgaaatag tcgaacatcc gtcgggccgt  17400
cggcgacagc ttgcggtact tctcccatat gaatttcgtg tagtggtcgc cagcaaacag  17460
cacgacgatt tcctcgtcga tcaggacctg gcaacgggac gttttcttgc cacggtccag  17520
gacgcggaag cggtgcagca gcgacaccga ttccaggtgc ccaacgcggt cggacgtgaa  17580
gcccatcgcc gtcgcctgta ggcgcgacag gcattcctcg gccttcgtgt aataccggcc  17640
attgatcgac cagcccaggt cctggcaaag ctcgtagaac gtgaaggtga tcggctcgcc  17700
gataggggtg cgcttcgcgt actccaacac ctgctgccac accagttcgt catcgtcggc  17760
ccgcagctcg acgccggtgt aggtgatctt cacgtccttg ttgacgtgga aaatgacctt  17820
gttttgcagc gcctcgcgcg ggattttctt gttgcgcgtg gtgaacaggg cagagcgggc  17880
cgtgtcgttt ggcatcgctc gcatcgtgtc cggccacggc gcaatatcga acaaggaaag  17940
ctgcatttcc ttgatctgct gcttcgtgtg tttcagcaac gcggcctgct tggcctcgct  18000
gacctgtttt gccaggtcct cgccggcggt ttttcgcttc ttggtcgtca tagttcctcg  18060
cgtgtcgatg gtcatcgact tcgccaaacc tgccgcctcc tgttcgagac gacgcgaacg  18120
ctccacggcg gccgatggcg cgggcagggc agggggagcc agttgcacgc tgtcgcgctc  18180
gatcttggcc gtagcttgct ggaccatcga gccgacggac tggaaggttt cgcggggcgc  18240
acgcatgacg gtgcggcttg cgatggtttc ggcatcctcg gcggaaaacc ccgcgtcgat  18300
cagttcttgc ctgtatgcct tccggtcaaa cgtccgattc attcaccctc cttgcgggat  18360
tgccccgact cacgccgggg caatgtgccc ttattcctga tttgacccgc ctggtgcctt  18420
ggtgtccaga taatccacct tatcggcaat gaagtcggtc ccgtagaccg tctggccgtc  18480
cttctcgtac ttggtattcc gaatcttgcc ctgcacgaat accagcgacc ccttgcccaa  18540
atacttgccg tgggcctcgg cctgagagcc aaaacacttg atgcggaaga agtcggtgcg  18600
ctcctgcttg tcgccggcat cgttgcgcca ctcttcatta accgctatat cgaaaattgc  18660
ttgcggcttg ttagaattgc catgacgtac ctcggtgtca cgggtaagat taccgataaa  18720
ctggaactga ttatggctca tatcgaaagt ctccttgaga aaggagactc tagtttagct  18780
aaacattggt tccgctgtca agaactttag cggctaaaat tttgcgggcc gcgaccaaag  18840
gtgcgagggg cggcttccgc tgtgtacaac cagatatttt tcaccaacat ccttcgtctg  18900
ctcgatgagc ggggcatgac gaaacatgag ctgtcggaga gggcaggggt ttcaatttcg  18960
tttttatcag acttaaccaa cggtaaggcc aacccctcgt tgaaggtgat ggaggccatt  19020
gccgacgccc tggaaactcc cctacctctt ctcctggagt ccaccgacct tgaccgcgag  19080
gcactcgcgg agattgcggg tcatcctttc aagagcagcg tgccgcccgg atacgaacgc  19140
atcagtgtgg ttttgccgtc acataaggcg tttatcgtaa agaaatgggg cgacgacacc  19200
cgaaaaaagc tgcgtggaag gctctgacgc caagggttag ggcttgcact tccttcttta  19260
gccgctaaaa cggccccttc tctgcgggcc gtcggctcgc gcatcatatc gacatcctca  19320
acggaagccg tgccgcgaat ggcatcgggc gggtgcgctt tgacagttgt tttctatcag  19380
aacccctacg tcgtgcggtt cgattagctg tttgtcttgc aggctaaaca ctttcggtat  19440
atcgtttgcc tgtgcgataa tgttgctaat gatttgttgc gtaggggtta ctgaaaagtg  19500
```

```
agcgggaaag aagagtttca gaccatcaag gagcgggcca agcgcaagct ggaacgcgac  19560
atgggtgcgg acctgttggc cgcgctcaac gacccgaaaa ccgttgaagt catgctcaac  19620
gcggacggca aggtgtggca cgaacgcctt ggcgagccga tgcggtacat ctgcgacatg  19680
cggcccagcc agtcgcaggc gattatagaa acggtggccg gattccacgg caaagaggtc  19740
acgcggcatt cgcccatcct ggaaggcgag ttccccttgg atggcagccg ctttgccggc  19800
caattgccgc cggtcgtggc cgcgccaacc tttgcgatcc gcaagcgcgc ggtcgccatc  19860
ttcacgctgg aacagtacgt cgaggcgggc atcatgaccc gcgagcaata cgaggtcatt  19920
aaaagcgccg tcgcggcgca tcgaaacatc ctcgtcattg gcggtactgg ctcgggcaag  19980
accacgctcg tcaacgcgat catcaatgaa atggtcgcct tcaacccgtc tgagcgcgtc  20040
gtcatcatcg aggacaccgg cgaaatccag tgcgccgcag agaacgccgt ccaataccac  20100
accagcatcg acgtctcgat gacgctgctg ctcaagacaa cgctgcgtat gcgccccgac  20160
cgcatcctgg tcggtgaggt acgtggcccc gaagcccttg atctgttgat ggcctggaac  20220
accgggcatg aaggaggtgc cgccaccctg cacgcaaaca accccaaagc gggcctgagc  20280
cggctcgcca tgcttatcag catgcacccg gattcaccga aacccattga gccgctgatt  20340
ggcgaggcgg ttcatgtggt cgtccatatc gccaggaccc ctagcggccg tcgagtgcaa  20400
gaaattctcg aagttcttgg ttacgagaac ggccagtaca tcaccaaaac cctgtaagga  20460
gtatttccaa tgacaacggc tgttccgttc cgtctgacca tgaatcgcgg cattttgttc  20520
taccttgccg tgttcttcgt tctcgctctc gcgttatccg cgcatccggc gatggcctcg  20580
gaaggcaccg gcggcagctt gccatatgag agctggctga cgaacctgcg caactccgta  20640
accggcccgg tggccttcgc gctgtccatc atcggcatcg tcgtcgccgg cggcgtgctg  20700
atcttcggcg gcgaactcaa cgccttcttc cgaaccctga tcttcctggt tctggtgatg  20760
gcgctgctgg tcggcgcgca gaacgtgatg agcaccttct tcggtcgtgg tgccgaaatc  20820
gcggccctcg gcaacggggc gctgcaccag gtgcaagtcg cggcggcgga tgccgtgcgt  20880
gcggtagcgg ctggacggct cgcctaatca tggctctgcg cacgatcccc atccgtcgcg  20940
caggcaaccg agaaaacctg ttcatgggtg gtgatcgtga actggtgatg ttctcgggcc  21000
tgatggcgtt tgcgctgatt ttcagcgccc aagagctgcg ggccaccgtg gtcggtctga  21060
tcctgtggtt cggggcgctc tatgcgttcc gaatcatggc gaaggccgat ccgaagatgc  21120
ggttcgtgta cctgcgtcac cgccggtaca agccgtatta cccggcccgc tcgacccccgt  21180
tccgcgagaa caccaatagc caagggaagc aataccgatg atccaagcaa ttgcgattgc  21240
aatcgcgggc ctcggcgcgc ttctgttgtt catcctcttt gcccgcatcc gcgcggtcga  21300
tgccgaactg aaactgaaaa agcatcgttc caaggacgcc ggcctggccg atctgctcaa  21360
ctacgccgct gtcgtcgatg acggcgtaat cgtgggcaag aacggcagct ttatggctgc  21420
ctggctgtac aagggcgatg acaacgcaag cagcaccgac cagcagcgcg aagtagtgtc  21480
cgcccgcatc aaccaggccc tcgcgggcct gggaagtggg tggatgatcc atgtggacgc  21540
cgtgcggcgt cctgctccga actacgcgga gcggggcctg tcggcgttcc ctgaccgtct  21600
gacggcagcg attgaagaag agcgctcggt cttgccttgc tcgtcggtga tgtacttcac  21660
cagctccgcg aagtcgctct tcttgatgga gcgcatgggg acgtgcttgg caatcacgcg  21720
cacccccggg ccgttttagc ggctaaaaaa gtcatggctc tgccctcggg cggaccacgc  21780
ccatcatgac cttgccaagc tcgtcctgct tctcttcgat cttcgccagc agggcgagga  21840
tcgtggcatc accgaaccgc gccgtgcgcg ggtcgtcggt gagccagagt ttcagcaggc  21900
```

```
cgcccaggcg gcccaggtcg ccattgatgc gggccagctc gcggacgtgc tcatagtcca  21960
cgacgcccgt gattttgtag ccctggccga cggccagcag gtaggccgac aggctcatgc  22020
cggccgccgc cgcctttcc tcaatcgctc ttcgttcgtc tggaaggcag tacaccttga  22080
taggtgggct gcccttcctg gttggcttgg tttcatcagc catccgcttg ccctcatctg  22140
ttacgccggc ggtagccggc cagcctcgca gagcaggatt cccgttgagc accgccaggt  22200
gcgaataagg gacagtgaag aaggaacacc cgctcgcggg tgggcctact tcacctatcc  22260
tgcccggctg acgccgttgg atacaccaag gaaagtctac acgaaccctt tggcaaaatc  22320
ctgtatatcg tgcgaaaaag gatggatata ccgaaaaaat cgctataatg accccgaagc  22380
agggttatgc agcggaaaag cgctgcttcc ctgctgtttt gtggaatatc taccgactgg  22440
aaacaggcaa atgcaggaaa ttactgaact gaggggacag gcgagagacg atgccaaaga  22500
gctacaccga cgagctggcc gagtgggttg aatcccgcgc ggccaagaag cgccggcgtg  22560
atgaggctgc ggttgcgttc ctggcggtga gggcggatgt cgaggcggcg ttagcgtccg  22620
gctatgcgct cgtcaccatt tgggagcaca tgcgggaaac ggggaaggtc aagttctcct  22680
acgagacgtt ccgctcgcac gccaggcggc acatcaaggc caagcccgcc gatgtgcccg  22740
caccgcaggc caaggctgcg gaacccgcgc cggcacccaa gacgccggag ccacggcggc  22800
cgaagcaggg gggcaaggct gaaaagccgg cccccgctgc ggccccgacc ggcttcacct  22860
tcaacccaac accggacaaa aaggatctac tgtaatggcg aaaattcaca tggttttgca  22920
gggcaagggc ggggtcggca agtcggccat cgccgcgatc attgcgcagt acaagatgga  22980
caaggggcag acacccttgt gcatcgacac cgacccggtg aacgcgacgt tcgagggcta  23040
caaggccctg aacgtccgcc ggctgaacat catggccggc gacgaaatta actcgcgcaa  23100
cttcgacacc ctggtcgagc tgattgcgcc gaccaaggat gacgtggtga tcgacaacgg  23160
tgccagctcg ttcgtgcctc tgtcgcatta cctcatcagc aaccaggtgc cggctctgct  23220
gcaagaaatg gggcatgagc tggtcatcca taccgtcgtc accggcggcc aggctctcct  23280
ggacacggtg agcggcttcg cccagctcgc cagccagttc ccggccgaag cgcttttcgt  23340
ggtctggctg aacccgtatt gggggcctat cgagcatgag ggcaagagct ttgagcagat  23400
gaaggcgtac acggccaaca aggcccgcgt gtcgtccatc atccagattc cggccctcaa  23460
ggaagaaacc tacggccgcg atttcagcga catgctgcaa gagcggctga cgttcgacca  23520
ggcgctggcc gatgaatcgc tcacgatcat gacgcggcaa cgcctcaaga tcgtgcggcg  23580
cggcctgttt gaacagctcg acgcggcggc cgtgctatga gcgaccagat tgaagagctg  23640
atccgggaga ttgcggccaa gcacggcatc gccgtcggcc gcgacgaccc ggtgctgatc  23700
ctgcatacca tcaacgcccg gctcatggcc gacagtgcgg ccaagcaaga ggaaatcctt  23760
gccgcgttca aggaagagct ggaagggatc gcccatcgtt ggggcgagga cgccaaggcc  23820
aaagcggagc ggatgctgaa cgcggccctg gcggccagca aggacgcaat ggcgaaggta  23880
atgaaggaca gcgccgcgca ggcggccgaa gcgatccgca gggaaatcga cgacggcctt  23940
ggccgccagc tcgcggccaa ggtcgcggac gcgcggcgcg tggcgatgat gaacatgatc  24000
gccggcggca tggtgttgtt cgcggccgcc ctggtggtgt gggcctcgtt atgaatcgca  24060
gaggcgcaga tgaaaaagcc cggcgttgcc gggctttgtt tttgcgttag ctgggcttgt  24120
ttgacaggcc caagctctga ctgcgcccgc gctcgcgctc ctgggcctgt ttcttctcct  24180
gctcctgctt gcgcatcagg gcctggtgcc gtcgggctgc ttcacgcatc gaatcccagt  24240
cgccggccag ctcgggatgc tccgcgcgca tcttgcgcgt cgccagttcc tcgatcttgg  24300
```

-continued

```
gcgcgtgaat gcccatgcct tccttgattt cgcgcaccat gtccagccgc gtgtgcaggg  24360
tctgcaagcg ggcttgctgt tgggcctgct gctgctgcca ggcggccttt gtacgcggca  24420
gggacagcaa gccgggggca ttggactgta gctgctgcaa acgcgcctgc tgacggtcta  24480
cgagctgttc taggcggtcc tcgatgcgct ccacctggtc atgctttgcc tgcacgtaga  24540
gcgcaagggt ctgctggtag gtctgctcga tgggcgcgga ttctaagagg gcctgctgtt  24600
ccgtctcggc ctcctgggcc gcctgtagca aatcctcgcc gctgttgccg ctggactgct  24660
ttactgccgg ggactgctgt tgccctgctc gcgccgtcgt cgcagttcgg cttgcccccca  24720
ctcgattgac tgcttcattt cgagccgcag cgatgcgatc tcggattgcg tcaacggacg  24780
gggcagcgcg gaggtgtccg gcttctcctt gggtgagtcg gtcgatgcca tagccaaagg  24840
tttccttcca aaatgcgtcc attgctggac cgtgtttctc attgatgccc gcaagcatct  24900
tcggcttgac cgccaggtca agcgcgcctt catgggcggt catgacggac gccgccatga  24960
ccttgccgcc gttgttctcg atgtagccgc gtaatgaggc aatggtgccg cccatcgtca  25020
gcgtgtcatc gacaacgatg tacttctggc cggggatcac ctccccctcg aaagtcgggt  25080
tgaacgccag gcgatgatct gaaccggctc cggttcgggc gaccttctcc cgctgcacaa  25140
tgtccgtttc gacctcaagg ccaaggcggt cggccagaac gaccgccatc atggccggaa  25200
tcttgttgtt ccccgccgcc tcgacggcga ggactggaac gatgcggggc ttgtcgtcgc  25260
cgatcagcgt cttgagctgg gcaacagtgt cgtccgaaat caggcgctcg accaaattaa  25320
gcgccgcttc cgcgtcgccc tgcttcgcag cctggtattc aggctcgttg gtcaaagaac  25380
caaggtcgcc gttgcgaacc accttcggga agtctcccca cggtgcgcgc tcggctctgc  25440
tgtagctgct caagacgcct cccttttag ccgctaaaac tctaacgagt gcgcccgcga  25500
ctcaacttga cgctttcggc acttacctgt gccttgccac ttgcgtcata ggtgatgctt  25560
ttcgcactcc cgatttcagg tactttatcg aaatctgacc gggcgtgcat tacaaagttc  25620
ttccccacct gttggtaaat gctgccgcta tctgcgtgga cgatgctgcc gtcgtggcgc  25680
tgcgacttat cggccttttg ggccatatag atgttgtaaa tgccaggttt cagggccccg  25740
gctttatcta ccttctggtt cgtccatgcg ccttggttct cggtctggac aattctttgc  25800
ccattcatga ccaggaggcg gtgtttcatt gggtgactcc tgacggttgc ctctggtgtt  25860
aaacgtgtcc tggtcgcttg ccggctaaaa aaaagccgac ctcggcagtt cgaggccggc  25920
tttccctaga gccgggcgcg tcaaggttgt tccatctatt ttagtgaact gcgttcgatt  25980
tatcagttac tttcctcccg ctttgtgttt cctcccactc gtttccgcgt ctagccgacc  26040
cctcaacata gcggcctctt cttgggctgc ctttgcctct tgccgcgctt cgtcacgctc  26100
ggcttgcacc gtcgtaaagc gctcggcctg cctggccgcc tcttgcgccg ccaacttcct  26160
ttgctcctgg tgggcctcgg cgtcggcctg cgccttcgct ttcaccgctg ccaactccgt  26220
gcgcaaactc tccgcttcgc gcctggtggc gtcgcgctcg ccgcgaagcg cctgcatttc  26280
ctggttggcc gcgtccaggg tcttgcggct ctcttctttg aatgcgcggg cgtcctggtg  26340
agcgtagtcc agctcggcgc gcagctcctg cgctcgacgc tccacctcgt cggcccgctg  26400
cgtcgccagc gcggcccgct gctcggctcc tgccagggcg gtgcgtgctt cggccagggc  26460
ttgccgctgg cgtgcggcca gctcggccgc ctcggcggcc tgctgctcta gcaatgtaac  26520
gcgcgcctgg gcttcttcca gctcgcgggc ctgcgcctcg aaggcgtcgg ccagctcccc  26580
gcgcacggct tccaactcgt tgcgctcacg atcccagccg gcttgcgctg cctgcaacga  26640
ttcattggca agggcctggg cggcttgcca gagggcggcc acggcctggt tgccggcctg  26700
```

```
ctgcaccgcg tccggcacct ggactgccag cggggcggcc tgcgccgtgc gctggcgtcg  26760
ccattcgcgc atgccggcgc tggcgtcgtt catgttgacg cgggcggcct tacgcactgc  26820
atccacggtc gggaagttct cccggtcgcc ttgctcgaac agctcgtccg cagccgcaaa  26880
aatgcggtcg cgcgtctctt tgttcagttc catgttggct ccggtaattg gtaagaataa  26940
taatactctt acctacctta tcagcgcaag agtttagctg aacagttctc gacttaacgg  27000
caggtttttt agcggctgaa gggcaggcaa aaaaagcccc gcacggtcgg cgggggcaaa  27060
gggtcagcgg gaaggggatt agcgggcgtc gggcttcttc atgcgtcggg gccgcgcttc  27120
ttgggatgga gcacgacgaa gcgcgcacgc gcatcgtcct cggccctatc ggcccgcgtc  27180
gcggtcagga acttgtcgcg cgctaggtcc tccctggtgg gcaccagggg catgaactcg  27240
gcctgctcga tgtaggtcca ctccatgacc gcatcgcagt cgaggccgcg ttccttcacc  27300
gtctcttgca ggtcgcggta cgcccgctcg ttgagcggct ggtaacgggc caattggtcg  27360
taaatggctg tcggccatga gcggcctttc ctgttgagcc agcagccgac gacgaagccg  27420
gcaatgcagg cccctggcac aaccaggccg acgccggggg caggggatgg cagcagctcg  27480
ccaaccagga accccgccgc gatgatgccg atgccggtca accagccctt gaaactatcc  27540
ggccccgaaa cacccctgcg cattgcctgg atgctgcgcc ggatagcttg caacatcagg  27600
agccgtttct tttgttcgtc agtcatggtc cgccctcacc agttgttcgt atcggtgtcg  27660
gacgaactga aatcgcaaga gctgccggta tcggtccagc cgctgtccgt gtcgctgctg  27720
ccgaagcacg gcgaggggtc cgcgaacgcc gcagacggcg tatccggccg cagcgcatcg  27780
cccagcatgg ccccggtcag cgagccgccg gccaggtagc ccagcatggt gctgttggtc  27840
gccccggcca ccagggccga cgtgacgaaa tcgccgtcat tccctctgga ttgttcgctg  27900
ctcggcgggg cagtgcgccg cgccggcggc gtcgtggatg gctcgggttg gctggcctgc  27960
gacggccggc gaaaggtgcg cagcagctcg ttatcgaccg gctgcggcgt cggggccgcc  28020
gccttgcgct gcggtcggtg ttccttcttc ggctcgcgca gcttgaacag catgatcgcg  28080
gaaaccagca gcaacgccgc gcctacgcct cccgcgatgt agaacagcat cggattcatt  28140
cttcggtcct ccttgtagcg gaaccgttgt ctgtgcggcg cgggtggccc gcgccgctgt  28200
ctttggggat cagccctcga tgagcgcgac cagtttcacg tcggcaaggt tcgcctcgaa  28260
ctcctggccg tcgtcctcgt acttcaacca ggcatagcct tccgccggcg gccgacggtt  28320
gaggataagg cgggcagggc gctcgtcgtg ctcgacctgg acgatggcct ttttcagctt  28380
gtccgggtcc ggctccttcg cgcccttttc cttggcgtcc ttaccgtcct ggtcgccgtc  28440
ctcgccgtcc tggccgtcgc cggcctccgc gtcacgctcg gcatcagtct ggccgttgaa  28500
ggcatcgacg gtgttgggat cgcggccctt ctcgtccagg aactcgcgca gcagcttgac  28560
cgtgccgcgc gtgatttcct gggtgtcgtc gtcaagccac gcctcgactt cctccgggcg  28620
cttcttgaag gccgtcacca gctcgttcac cacggtcacg tcgcgcacgc ggccggtgtt  28680
gaacgcatcg gcgatcttct ccggcaggtc cagcagcgtg acgtgctggg tgatgaacgc  28740
cggcgacttg ccgatttcct tggcgatatc gcctttcttc ttgcccttcg ccagctcgcg  28800
gccaatgaag tcggcaattt cgcgcggggt cagctcgttg cgttgcaggt tctcgataac  28860
ctggtcggct tcgttgtagt cgttgtcgat gaacgccggg atggacttct tgccggccca  28920
cttcgagcca cggtagcggc gggcgccgtg attgatgata tagcggcccg gctgctcctg  28980
gttctcgcgc accgaaatgg gtgacttcac cccgcgctct ttgatcgtgg caccgatttc  29040
cgcgatgctc tccggggaaa agccggggtt gtcggccgtc cgcggctgat gcggatcttc  29100
```

```
gtcgatcagg tccaggtcca gctcgatagg gccggaaccg ccctgagacg ccgcaggagc  29160
gtccaggagg ctcgacaggt cgccgatgct atccaacccc aggccggacg gctgcgccgc  29220
gcctgcggct tcctgagcgg ccgcagcggt gtttttcttg gtggtcttgg cttgagccgc  29280
agtcattggg aaatctccat cttcgtgaac acgtaatcag ccagggcgcg aacctctttc  29340
gatgccttgc gcgcggccgt tttcttgatc ttccagaccg gcacaccgga tgcgagggca  29400
tcggcgatgc tgctgcgcag gccaacggtg gccggaatca tcatcttggg gtacgcggcc  29460
agcagctcgg cttggtggcg cgcgtggcgc ggattccgcg catcgacctt gctgggcacc  29520
atgccaagga attgcagctt ggcgttcttc tggcgcacgt tcgcaatggt cgtgaccatc  29580
ttcttgatgc cctggatgct gtacgcctca agctcgatgg gggacagcac atagtcggcc  29640
gcgaagaggg cggccgccag gccgacgcca agggtcgggg ccgtgtcgat caggcacacg  29700
tcgaagcctt ggttcgccag ggccttgatg ttcgccccga acagctcgcg ggcgtcgtcc  29760
agcgacagcc gttcggcgtt cgccagtacc gggttggact cgatgagggc gaggcgcgcg  29820
gcctggccgt cgccggctgc gggtgcggtt tcggtccagc cgccggcagg gacagcgccg  29880
aacagcttgc ttgcatgcag gccggtagca aagtccttga gcgtgtagga cgcattgccc  29940
tgggggtcca ggtcgatcac ggcaacccgc aagccgcgct cgaaaaagtc gaaggcaaga  30000
tgcacaaggg tcgaagtctt gccgacgccg cctttctggt tggccgtgac caaagttttc  30060
atcgtttggt ttcctgtttt ttcttggcgt ccgcttccca cttccggacg atgtacgcct  30120
gatgttccgg cagaaccgcc gttacccgcg cgtacccctc gggcaagttc ttgtcctcga  30180
acgcggccca cacgcgatgc accgcttgcg acactgcgcc cctggtcagt cccagcgacg  30240
ttgcgaacgt cgcctgtggc ttcccatcga ctaagacgcc ccgcgctatc tcgatggtct  30300
gctgccccac ttccagcccc tggatcgcct cctggaactg gctttcggta agccgtttct  30360
tcatggataa cacccataat ttgctccgcg ccttggttga acatagcggt gacagccgcc  30420
agcacatgag agaagtttag ctaaacattt ctcgcacgtc aacaccttta gccgctaaaa  30480
ctcgtccttg gcgtaacaaa acaaaagccc ggaaaccggg ctttcgtctc ttgccgctta  30540
tggctctgca cccggctcca tcaccaacag gtcgcgcacg cgcttcactc ggttgcggat  30600
cgacactgcc agcccaacaa agccggttgc cgccgccgcc aggatcgcgc cgatgatgcc  30660
ggccacaccg gccatcgccc accaggtcgc cgccttccgg ttccattcct gctggtactg  30720
cttcgcaatg ctggacctcg gctcaccata ggctgaccgc tcgatggcgt atgccgcttc  30780
tccccttggc gtaaaaccca gcgccgcagg cggcattgcc atgctgcccg ccgctttccc  30840
gaccacgacg cgcgcaccag gcttgcggtc cagaccttcg gccacggcga gctgcgcaag  30900
gacataatca gccgccgact tggctccacg cgcctcgatc agctcttgca ctcgcgcgaa  30960
atccttggcc tccacggccg ccatgaatcg cgcacgcggc gaaggctccg cagggccggc  31020
gtcgtgatcg ccgccgagaa tgcccttcac caagttcgac gacacgaaaa tcatgctgac  31080
ggctatcacc atcatgcaga cggatcgcac gaacccgctg aattgaacac gagcacggca  31140
cccgcgacca ctatgccaag aatgcccaag gtaaaaattg ccggccccgc catgaagtcc  31200
gtgaatgccc cgacggccga agtgaagggc aggccgccac ccaggccgcc gccctcactg  31260
cccggcacct ggtcgctgaa tgtcgatgcc agcacctgcg gcacgtcaat gcttccgggc  31320
gtcgcgctcg ggctgatcgc ccatcccgtt actgccccga tcccggcaat ggcaaggact  31380
gccagcgctg ccatttttgg ggtgaggccg ttcgcggccg aggggcgcag cccctggggg  31440
gatgggaggc ccgcgttagc gggccgggag ggttcgagaa ggggggcac cccccttcgg  31500
```

```
cgtgcgcggt cacgcgcaca gggcgcagcc ctggttaaaa acaaggttta taaatattgg  31560
tttaaaagca ggttaaaaga caggttagcg gtggccgaaa aacgggcgga aacccttgca  31620
aatgctggat tttctgcctg tggacagccc ctcaaatgtc aataggtgcg cccctcatct  31680
gtcagcactc tgcccctcaa gtgtcaagga tcgcgcccct catctgtcag tagtcgcgcc  31740
cctcaagtgt caataccgca gggcacttat ccccaggctt gtccacatca tctgtgggaa  31800
actcgcgtaa aatcaggcgt tttcgccgat ttgcgaggct ggccagctcc acgtcgccgg  31860
ccgaaatcga gcctgcccct catctgtcaa cgccgcgccg ggtgagtcgg cccctcaagt  31920
gtcaacgtcc gcccctcatc tgtcagtgag ggccaagttt tccgcgaggt atccacaacg  31980
ccggcggccg cggtgtctcg cacacggctt cgacggcgtt tctggcgcgt ttgcagggcc  32040
atagacggcc gccagcccag cggcgagggc aaccagcccg gtgagcgtcg gaaaggcgct  32100
ggaagccccg tagcgacgcg gagaggggcg agacaagcca agggcgcagg ctcgatgcgc  32160
agcacgacat agccggttct cgcaaggacg agaatttccc tgcggtgccc ctcaagtgtc  32220
aatgaaagtt tccaacgcga gccattcgcg agagccttga gtccacgcta gatgagagct  32280
ttgttgtagg tggaccagtt ggtgattttg aacttttgct ttgccacgga acggtctgcg  32340
ttgtcgggaa gatgcgtgat ctgatccttc aactcagcaa aagttcgatt tattcaacaa  32400
agccacgttg tgtctcaaaa tctctgatgt tacattgcac aagataaaaa tatatcatca  32460
tgaacaataa aactgtctgc ttacataaac agtaatacaa ggggtgttat gagccatatt  32520
caacgggaaa cgtcttgctc gactctagag ctcgttcctc gaggcctcga ggcctcgagg  32580
aacggtacct gcggggaagc ttacaataat gtgtgttgtt aagtcttgtt gcctgtcatc  32640
gtctgactga ctttcgtcat aaatcccggc ctccgtaacc cagctttggg caagctcacg  32700
gatttgatcc ggcggaacgg gaatatcgag atgccgggct gaacgctgca gttccagctt  32760
tccctttcgg gacaggtact ccagctgatt gattatctgc tgaagggtct tggttccacc  32820
tcctggcaca atgcgaatga ttacttgagc gcgatcgggc atccaatttt ctcccgtcag  32880
gtgcgtggtc aagtgctaca aggcaccttt cagtaacgag cgaccgtcga tccgtcgccg  32940
ggatacggac aaaatggagc gcagtagtcc atcgagggcg gcgaaagcct cgccaaaagc  33000
aatacgttca tctcgcacag cctccagatc cgatcgaggg tcttcggcgt aggcagatag  33060
aagcatggat acattgcttg agagtattcc gatggactga agtatggctt ccatcttttc  33120
tcgtgtgtct gcatctattt cgagaaagcc cccgatgcgg cgcaccgcaa cgcgaattgc  33180
catactatcc gaaagtccca gcaggcgcgc ttgataggaa aaggtttcat actcggccga  33240
tcgcagacgg gcactcacga ccttgaaccc ttcaactttc agggatcgat gctggttgat  33300
ggtagtctca ctcgacgtgg ctctggtgtg ttttgacata gcttcctcca aagaaagcgg  33360
aaggtctgga tactccagca cgaaatgtgc ccgggtagac ggatggaagt ctagccctgc  33420
tcaatatgaa atcaacagta catttacagt caatactgaa tatacttgct acatttgcaa  33480
ttgtcttata acgaatgtga aataaaaata gtgtaacaac gcttttactc atcgataatc  33540
acaaaaacat ttatacgaac aaaaatacaa atgcactccg gtttcacagg ataggcggga  33600
tcagaatatg caacttttga cgttttgttc tttcaaaggg ggtgctggca aaaccaccgc  33660
actcatgggc ctttgcgctg ctttggcaaa tgacggtaaa cgagtggccc tctttgatgc  33720
cgacgaaaac cggcctctga cgcgatggag agaaaacgcc ttacaaagca gtactgggat  33780
cctcgctgtg aagtctattc cgccgacgaa atgccccttc ttgaagcagc ctatgaaaat  33840
gccgagctcg aaggatttga ttatgcgttg gccgatacgc gtggcggctc gagcgagctc  33900
```

```
aacaacacaa tcatcgctag ctcaaacctg cttctgatcc ccaccatgct aacgccgctc  33960
gacatcgatg aggcactatc tacctaccgc tacgtcatcg agctgctgtt gagtgaaaat  34020
ttggcaattc ctacagctgt tttgcgccaa cgcgtcccgg tcggccgatt gacaacatcg  34080
caacgcagga tgtcagagac gctagagagc cttccagttg taccgtctcc catgcatgaa  34140
agagatgcat ttgccgcgat gaaagaacgc ggcatgttgc atcttacatt actaaacacg  34200
ggaactgatc cgacgatgcg cctcatagag aggaatcttc ggattgcgat ggaggaagtc  34260
gtggtcattt cgaaactgat cagcaaaatc ttggaggctt gaagatggca attcgcaagc  34320
ccgcattgtc ggtcggcgaa gcacggcggc ttgctggtgc tcgacccgag atccaccatc  34380
ccaacccgac acttgttccc cagaagctgg acctccagca cttgcctgaa aaagccgacg  34440
agaaagacca gcaacgtgag cctctcgtcg ccgatcacat ttacagtccc gatcgacaac  34500
ttaagctaac tgtggatgcc cttagtccac ctccgtcccc gaaaaagctc caggtttttc  34560
tttcagcgcg accgcccgcg cctcaagtgt cgaaaacata tgacaacctc gttcggcaat  34620
acagtccctc gaagtcgcta caaatgattt taaggcgcgc gttggacgat ttcgaaagca  34680
tgctggcaga tggatcattt cgcgtggccc cgaaaagtta tccgatccct tcaactacag  34740
aaaaatccgt tctcgttcag acctcacgca tgttcccggt tgcgttgctc gaggtcgctc  34800
gaagtcattt tgatccgttg ggttggaga ccgctcgagc tttcggccac aagctggcta  34860
ccgccgcgct cgcgtcattc tttgctggag agaagccatc gagcaattgg tgaagaggga  34920
cctatcggaa cccctcacca aatattgagt gtaggtttga ggccgctggc cgcgtcctca  34980
gtcacctttt gagccagata attaagagcc aaatgcaatt ggctcaggct gccatcgtcc  35040
ccccgtgcga aacctgcacg tccgcgtcaa agaaataacc ggcacctctt gctgttttta  35100
tcagttgagg gcttgacgga tccgcctcaa gtttgcggcg cagccgcaaa atgagaacat  35160
ctatactcct gtcgtaaacc tcctcgtcgc gtactcgact ggcaatgaga agttgctcgc  35220
gcgatagaac gtcgcggggt ttctctaaaa acgcgaggag aagattgaac tcacctgccg  35280
taagtttcac ctcaccgcca gcttcggaca tcaagcgacg ttgcctgaga ttaagtgtcc  35340
agtcagtaaa acaaaaagac cgtcggtctt tggagcggac aacgttgggg cgcacgcgca  35400
aggcaacccg aatgcgtgca agaaactctc tcgtactaaa cggcttagcg ataaaatcac  35460
ttgctcctag ctcgagtgca acaactttat ccgtctcctc aaggcggtcg ccactgataa  35520
ttatgattgg aatatcagac tttgccgcca gatttcgaac gatctcaagc ccatcttcac  35580
gacctaaatt tagatcaaca accacgacat cgaccgtcgc ggaagagagt actctagtga  35640
actgggtgct gtcggctacc gcggtcactt tgaaggcgtg gatcgtaagg tattcgataa  35700
taagatgccg catagcgaca tcgtcatcga taagaagaac gtgtttcaac ggctcacctt  35760
tcaatctaaa atctgaaccc ttgttcacag cgcttgagaa attttcacgt gaaggatgta  35820
caatcatctc cagctaaatg ggcagttcgt cagaattgcg gctgaccgcg gatgacgaaa  35880
atgcgaacca agtatttcaa ttttatgaca aaagttctca atcgttgtta caagtgaaac  35940
gcttcgaggt tacagctact attgattaag gagatcgcct atggtctcgc cccggcgtcg  36000
tgcgtccgcc gcgagccaga tctcgcctac ttcataaacg tcctcatagg cacggaatgg  36060
aatgatgaca tcgatcgccg tagagagcat gtcaatcagt gtgcgatctt ccaagctagc  36120
accttgggcg ctacttttga caagggaaaa cagtttcttg aatccttgga ttggattcgc  36180
gccgtgtatt gttgaaatcg atcccggatg tcccgagacg acttcactca gataagccca  36240
tgctgcatcg tcgcgcatct cgccaagcaa tatccggtcc ggccgcatac gcagacttgc  36300
```

-continued

```
ttggagcaag tgctcggcgc tcacagcacc cagcccagca ccgttcttgg agtagagtag  36360
tctaacatga ttatcgtgtg gaatgacgag ttcgagcgta tcttctatgg tgattagcct  36420
ttcctggggg gggatggcgc tgatcaaggt cttgctcatt gttgtcttgc cgcttccggt  36480
agggccacat agcaacatcg tcagtcggct gacgacgcat gcgtgcagaa acgcttccaa  36540
atccccgttg tcaaaatgct gaaggatagc ttcatcatcc tgattttggc gtttccttcg  36600
tgtctgccac tggttccacc tcgaagcatc ataacgggag gagacttctt taagaccaga  36660
aacacgcgag cttggccgtc gaatggtcaa gctgacggtg cccgagggaa cggtcggcgg  36720
cagacagatt tgtagtcgtt caccaccagg aagttcagtg gcgcagaggg ggttacgtgg  36780
tccgacatcc tgctttctca gcgcgcccgc taaaatagcg atatcttcaa gatcatcata  36840
agagacgggc aaaggcatct tggtaaaaat gccggcttgg cgcacaaatg cctctccagg  36900
tcgattgatc gcaatttctt cagtcttcgg gtcatcgagc cattccaaaa tcggcttcag  36960
aagaaagcgt agttgcggat ccacttccat ttacaatgta tcctatctct aagcggaaat  37020
ttgaattcat taagagcggc ggttcctccc ccgcgtggcg ccgccagtca ggcggagctg  37080
gtaaacacca aagaaatcga ggtcccgtgc tacgaaaatg gaaacggtgt caccctgatt  37140
cttcttcagg gttggcggta tgttgatggt tgccttaagg gctgtctcag ttgtctgctc  37200
accgttattt tgaaagctgt tgaagctcat cccgccaccc gagctgccgg cgtaggtgct  37260
agctgcctgg aaggcgcctt gaacaacact caagagcata gctccgctaa aacgctgcca  37320
gaagtggctg tcgaccgagc ccggcaatcc tgagcgaccg agttcgtccg cgcttggcga  37380
tgttaacgag atcatcgcat ggtcaggtgt ctcggcgcga tcccacaaca caaaaacgcg  37440
cccatctccc tgttgcaagc cacgctgtat ttcgccaaca acggtggtgc cacgatcaag  37500
aagcacgata ttgttcgttg ttccacgaat atcctgaggc aagacacact ttacatagcc  37560
tgccaaattt gtgtcgattg cggtttgcaa gatgcacgga attattgtcc cttgcgttac  37620
cataaaatcg gggtgcggca agagcgtggc gctgctgggc tgcagctcgg tgggtttcat  37680
acgtatcgac aaatcgttct cgccggacac ttcgccattc ggcaaggagt tgtcgtcacg  37740
cttgccttct tgtcttcggc ccgtgtcgcc ctgaatggcg cgtttgctga ccccttgatc  37800
gccgctgcta tatgcaaaaa tcggtgtttc ttccggccgt ggctcatgcc gctccggttc  37860
gcccctcggc ggtagaggag cagcaggctg aacagcctct tgaaccgctg gaggatccgg  37920
cggcacctca atcggagctg gatgaaatgg cttggtgttt gttgcgatca aagttgacgg  37980
cgatgcgttc tcattcacct tcttttggcg cccacctagc caaatgaggc ttaatgataa  38040
cgcgagaacg acacctccga cgatcaattt ctgagacccc gaaagacgcc ggcgatgttt  38100
gtcggagacc agggatccag atgcatcaac ctcatgtgcc gcttgctgac tatcgttatt  38160
catcccttcg ccccttcag gacgcgtttc acatcgggcc tcaccgtgcc cgtttgcggc  38220
ctttggccaa cgggatcgta agcggtgttc cagatacata gtactgtgtg gccatccctc  38280
agacgccaac ctcgggaaac cgaagaaatc tcgacatcgc tccctttaac tgaatagttg  38340
gcaacagctt ccttgccatc aggattgatg gtgtagatgg agggtatgcg tacattgccc  38400
ggaaagtgga ataccgtcgt aaatccattg tcgaagactt cgagtggcaa cagcgaacga  38460
tcgccttggg cgacgtagtg ccaattactg tccgccgcac caagggctgt gacaggctga  38520
tccaataaat tctcagcttt ccgttgatat tgtgcttccg cgtgtagtct gtccacaaca  38580
gccttctgtt gtgcctccct tcgccgagcc gccgcatcgt cggcggggta ggcgaattgg  38640
acgctgtaat agagatcggg ctgctcttta tcgaggtggg acagagtctt ggaacttata  38700
```

```
ctgaaaacat aacggcgcat cccggagtcg cttgcggtta gcacgattac tggctgaggc  38760
gtgaggacct ggcttgcctt gaaaaataga taatttcccc gcggtagggc tgctagatct  38820
ttgctatttg aaacggcaac cgctgtcacc gtttcgttcg tggcgaatgt tacgaccaaa  38880
gtagctccaa ccgccgtcga gaggcgcacc acttgatcgg gattgtaagc caaataacgc  38940
atgcgcggat ctagcttgcc cgccattgga gtgtcttcag cctccgcacc agtcgcagcg  39000
gcaaataaac atgctaaaat gaaaagtgct tttctgatca tggttcgctg tggcctacgt  39060
ttgaaacggt atcttccgat gtctgatagg aggtgacaac cagacctgcc gggttggtta  39120
gtctcaatct gccgggcaag ctggtcacct tttcgtagcg aactgtcgcg gtccacgtac  39180
tcaccacagg cattttgccg tcaacgacga gggtcctttt atagcgaatt tgctgcgtgc  39240
ttggagttac atcatttgaa gcgatgtgct cgacctccac cctgccgcgt ttgccaagaa  39300
tgacttgagg cgaactggga ttgggatagt tgaagaattg ctggtaatcc tggcgcactg  39360
ttggggcact gaagttcgat accaggtcgt aggcgtactg agcggtgtcg gcatcataac  39420
tctcgcgcag gcgaacgtac tcccacaatg aggcgttaac gacggcctcc tcttgagttg  39480
caggcaatcg cgagacagac acctcgctgt caacggtgcc gtccggccgt atccatagat  39540
atacgggcac aagcctgctc aacggcacca ttgtggctat agcgaacgct tgagcaacat  39600
ttcccaaaat cgcgatagct gcgacagctg caatgagttt ggagagacgt cgcgccgatt  39660
tcgctcgcgc ggtttgaaag gcttctactt ccttatagtg ctcggcaagg ctttcgcgcg  39720
ccactagcat ggcatattca ggccccgtca tagcgtccac ccgaattgcc gagctgaaga  39780
tctgacggag taggctgcca tcgccccaca ttcagcggga agatcgggcc tttgcagctc  39840
gctaatgtgt cgtttgtctg gcagccgctc aaagcgacaa ctaggcacag caggcaatac  39900
ttcatagaat tctccattga ggcgaatttt tgcgcgacct agcctcgctc aacctgagcg  39960
aagcgacggt acaagctgct ggcagattgg gttgcgccgc tccagtaact gcctccaatg  40020
ttgccggcga tcgccggcaa agcgacaatg agcgcatccc ctgtcagaaa aaacatatcg  40080
agttcgtaaa gaccaatgat cttggccgcg gtcgtaccgg cgaaggtgat tacaccaagc  40140
ataagggtga gcgcagtcgc ttcggttagg atgacgatcg ttgccacgag gtttaagagg  40200
agaagcaaga gaccgtaggt gataagttgc ccgatccact tagctgcgat gtcccgcgtg  40260
cgatcaaaaa tatatccgac gaggatcaga ggcccgatcg cgagaagcac tttcgtgaga  40320
attccaacgg cgtcgtaaac tccgaaggca gaccagagcg tgccgtaaag gacccactgt  40380
gccccttgga aagcaaggat gtcctggtcg ttcatcggac cgatttcgga tgcgattttc  40440
tgaaaaacgg cctgggtcac ggcgaacatt gtatccaact gtgccggaac agtctgcaga  40500
ggcaagccgg ttacactaaa ctgctgaaca aagtttggga ccgtcttttc gaagatggaa  40560
accacatagt cttggtagtt agcctgccca acaattagag caacaacgat ggtgaccgtg  40620
atcacccgag tgataccgct acgggtatcg acttcgccgc gtatgactaa aataccctga  40680
acaataatcc aaagagtgac acaggcgatc aatggcgcac tcaccgcctc ctggatagtc  40740
tcaagcatcg agtccaagcc tgtcgtgaag gctacatcga agatcgtatg aatggccgta  40800
aacggcgccg gaatcgtgaa attcatcgat tggacctgaa cttgactggt ttgtcgcata  40860
atgttggata aaatgagctc gcattcggcg aggatgcggg cggatgaaca aatcgcccag  40920
ccttagggga gggcaccaaa gatgacagcg gtcttttgat gctccttgcg ttgagcggcc  40980
gcctcttccg cctcgtgaag gccggcctgc gcggtagtca tcgttaatag gcttgtcgcc  41040
tgtacatttt gaatcattgc gtcatggatc tgcttgagaa gcaaaccatt ggtcacggtt  41100
```

```
gcctgcatga tattgcgaga tcgggaaagc tgagcagacg tatcagcatt cgccgtcaag  41160
cgtttgtcca tcgtttccag attgtcagcc gcaatgccag cgctgtttgc ggaaccggtg  41220
atctgcgatc gcaacaggtc cgcttcagca tcactaccca cgactgcacg atctgtatcg  41280
ctggtgatcg cacgtgccgt ggtcgacatt ggcattcgcg gcgaaaacat ttcattgtct  41340
aggtccttcg tcgaaggata ctgatttttc tggttgagcg aagtcagtag tccagtaacg  41400
ccgtaggccg acgtcaacat cgtaaccatc gctatagtct gagtgagatt ctccgcagtc  41460
gcgagcgcag tcgcgagcgt ctcagcctcc gttgccgggt cgctaacaac aaactgcgcc  41520
cgcgcgggct gaatatatag aaagctgcag gtcaaaactg ttgcaataag ttgcgtcgtc  41580
ttcatcgttt cctaccttat caatcttctg cctcgtggtg acgggccatg aattcgctga  41640
gccagccaga tgagttgcct tcttgtgcct cgcgtagtcg agttgcaaag cgcaccgtgt  41700
tggcacgccc cgaaagcacg gcgacatatt cacgcatatc ccgcagatca aattcgcaga  41760
tgacgcttcc actttctcgt ttaagaagaa acttacggct gccgaccgtc atgtcttcac  41820
ggatcgcctg aaattccttt tcggtacatt tcagtccatc gacataagcc gatcgatctg  41880
cggttggtga tggatagaaa atcttcgtca tacattgcgc aaccaagctg gctcctagcg  41940
gcgattccag aacatgctct ggttgctgcg ttgccagtat tagcatcccg ttgttttttc  42000
gaacggtcag gaggaatttg tcgacgacag tcgaaaattt agggtttaac aaataggcgc  42060
gaaactcatc gcagctcatc acaaaaacggc ggccgtcgat catggctcca atccgatgca  42120
ggagatatgc tgcagcggga gcgcatactt cctcgtattc gagaagatgc gtcatgtcga  42180
agccggtaat cgacggatct aactttactt cgtcaacttc gccgtcaaat gcccagccaa  42240
gcgcatggcc ccggcaccag cgttggagcc gcgctcctgc gccttcggcg ggcccatgca  42300
acaaaaattc acgtaacccc gcgattgaac gcatttgtgg atcaaacgag agctgacgat  42360
ggataccacg gaccagacgg cggttctctt ccggagaaat cccaccccga ccatcactct  42420
cgatgagagc cacgatccat tcgcgcagaa aatcgtgtga ggctgctgtg ttttctaggc  42480
cacgcaacgg cgccaacccg ctgggtgtgc ctctgtgaag tgccaaatat gttcctcctg  42540
tggcgcgaac cagcaattcg ccaccccggt ccttgtcaaa gaacacgacc gtacctgcac  42600
ggtcgaccat gctctgttcg agcatggcta gaacaaacat catgagcgtc gtcttacccc  42660
tcccgatagg cccgaatatt gccgtcatgc caacatcgtg ctcatgcggg atatagtcga  42720
aaggcgttcc gccattggta cgaaatcggg caatcgcgtt gccccagtgg cctgagctgg  42780
cgccctctgg aaagttttcg aaagagacaa accctgcgaa attgcgtgaa gtgattgcgc  42840
cagggcgtgt gcgccactta aaattccccg gcaattggga ccaataggcc gcttccatac  42900
caataccttc ttggacaacc acggcacctg catccgccat tcgtgtccga gcccgcgcgc  42960
ccctgtcccc aagactattg agatcgtctg catagacgca aaggctcaaa tgatgtgagc  43020
ccataacgaa ttcgttgctc gcaagtgcgt cctcagcctc ggataatttg ccgatttgag  43080
tcacggcttt atcgccggaa ctcagcatct ggctcgattt gaggctaagt ttcgcgtgcg  43140
cttgcgggcg agtcaggaac gaaaaactct gcgtgagaac aagtggaaaa tcgagggata  43200
gcagcgcgtt gagcatgccc ggccgtgttt ttgcagggta ttcgcgaaac gaatagatgg  43260
atccaacgta actgtctttt ggcgttctga tctcgagtcc tcgcttgccg caaatgactc  43320
tgtcggtata aatcgaagcg ccgagtgagc cgctgacgac cggaaccggt gtgaaccgac  43380
cagtcatgat caaccgtagc gcttcgccaa tttcggtgaa gagcacaccc tgcttctcgc  43440
ggatgccaag acgatgcagg ccatacgctt taagagagcc agcgacaaca tgccaaagat  43500
```

cttccatgtt cctgatctgg cccgtgagat cgttttccct ttttccgctt agcttggtga 43560
acctcctctt taccttccct aaagccgcct gtgggtagac aatcaacgta aggaagtgtt 43620
cattgcggag gagttggccg gagagcacgc gctgttcaaa agcttcgttc aggctagcgg 43680
cgaaaacact acggaagtgt cgcggcgccg atgatggcac gtcggcatga cgtacgaggt 43740
gagcatatat tgacacatga tcatcagcga tattgcgcaa cagcgtgttg aacgcacgac 43800
aacgcgcatt gcgcatttca gtttcctcaa gctcgaatgc aacgccatca attctcgcaa 43860
tggtcatgat cgatccgtct tcaagaagga cgatatggtc gctgaggtgg ccaatataag 43920
ggagatagat ctcaccggat ctttcggtcg ttccactcgc gccgagcatc acaccattcc 43980
tctccctcgt gggggaaccc taattggatt tgggctaaca gtagcgcccc cccaaactgc 44040
actatcaatg cttcttcccg cggtccgcaa aaatagcagg acgacgctcg ccgcattgta 44100
gtctcgctcc acgatgagcc gggctgcaaa ccataacggc acgagaacga cttcgtagag 44160
cgggttctga acgataacga tgacaaagcc ggcgaacatc atgaataacc ctgccaatgt 44220
cagtggcacc ccaagaaaca atgcgggccg tgtggctgcg aggtaaaggg tcgattcttc 44280
caaacgatca gccatcaact accgccagtg agcgtttggc cgaggaagct cgccccaaac 44340
atgataacaa tgccgccgac gacgccggca accagcccaa gcgaagcccg cccgaacatc 44400
caggagatcc cgatagcgac aatgccgaga acagcgagtg actggccgaa cggaccaagg 44460
ataaacgtgc atatattgtt aaccattgtg gcggggtcag tgccgccacc cgcagattgc 44520
gctgcggcgg gtccggatga ggaaatgctc catgcaattg caccgcacaa gcttggggcg 44580
cagctcgata tcacgcgcat catcgcattc gagagcgaga ggcgatttag atgtaaacgg 44640
tatctctcaa agcatcgcat caatgcgcac ctccttagta taagtcgaat aagacttgat 44700
tgtcgtctgc ggatttgccg ttgtcctggt gtggcggtgg cggagcgatt aaaccgccag 44760
cgccatcctc ctgcgagcgg cgctgatatg acccccaaac atcccacgtc tcttcggatt 44820
ttagcgcctc gtgatcgtct tttggaggct cgattaacgc gggcaccagc gattgagcag 44880
ctgtttcaac ttttcgcacg tagccgtttg caaaaccgcc gatgaaatta ccggtgttgt 44940
aagcggagat cgcccgacga agcgcaaatt gcttctcgtc aatcgtttcg ccgcctgcat 45000
aacgactttt cagcatgttt gcagcggcag ataatgatgt gcacgcctgg agcgcaccgt 45060
caggtgtcag accgagcata gaaaaatttc gagagtttat ttgcatgagg ccaacatcca 45120
gcgaatgccg tgcatcgaga cggtgcctga cgacttgggt tgcttggctg tgatcttgcc 45180
agtgaagcgt ttcgccggtc gtgttgtcat gaatcgctaa aggatcaaag cgactctcca 45240
ccttagctat cgccgcaagc gtagatgtcg caactgatgg ggcacacttg cgagcaacat 45300
ggtcaaactc agcagatgag agtggcgtgg caaggctcga cgaacagaag gagaccatca 45360
aggcaagaga aagcgacccc gatctcttaa gcatacctta tctccttagc tcgcaactaa 45420
caccgcctct cccgttggaa gaagtgcgtt gttttatgtt gaagattatc gggagggtcg 45480
gttactcgaa aattttcaat tgcttcttta tgatttcaat tgaagcgaga aacctcgccc 45540
ggcgtcttgg aacgcaacat ggaccgagaa ccgcgcatcc atgactaagc aaccggatcg 45600
acctattcag gccgcagttg gtcaggtcag gctcagaacg aaaatgctcg gcgaggttac 45660
gctgtctgta aacccattcg atgaacggga agcttccttc cgattgctct tggcaggaat 45720
attggcccat gcctgcttgc gctttgcaaa tgctcttatc gcgttggtat catatgcctt 45780
gtccgccagc agaaacgcac tctaagcgat tatttgtaaa aatgtttcgg tcatgcggcg 45840
gtcatgggct tgacccgctg tcagcgcaag acggatcggt caaccgtcgg catcgacaac 45900

-continued

```
agcgtgaatc ttggtggtca aaccgccacg ggaacgtccc atacagccat cgtcttgatc  45960
ccgctgtttc ccgtcgccgc atgttggtgg acgcggacac aggaactgtc aatcatgacg  46020
acattctatc gaaagccttg gaaatcacac tcagaatatg atcccagacg tctgcctcac  46080
gccatcgtac aaagcgattg tagcaggttg tacaggaacc gtatcgatca ggaacgtctg  46140
cccagggcgg gcccgtccgg aagcgccaca agatgacatt gatcacccgc gtcaacgcgc  46200
ggcacgcgac gcggcttatt tgggaacaaa ggactgaaca acagtccatt cgaaatcggt  46260
gacatcaaag cggggacggg ttatcagtgg cctccaagtc aagcctcaat gaatcaaaat  46320
cagaccgatt tgcaaacctg atttatgagt gtgcggccta aatgatgaaa tcgtccttct  46380
agatcgcctc cgtggtgtag caacacctcg cagtatcgcc gtgctgacct tggccaggga  46440
attgactggc aagggtgctt tcacatgacc gctcttttgg ccgcgataga tgatttcgtt  46500
gctgctttgg gcacgtagaa ggagagaagt catatcggag aaattcctcc tggcgcgaga  46560
gcctgctcta tcgcgacggc atcccactgt cgggaacaga ccggatcatt cacgaggcga  46620
aagtcgtcaa cacatgcgtt ataggcatct tcccttgaag gatgatcttg ttgctgccaa  46680
tctggaggtg cggcagccgc aggcagatgc gatctcagcg caacttgcgg caaaacatct  46740
cactcacctg aaaaccacta gcgagtctcg cgatcagacg aaggcctttt acttaacgac  46800
acaatatccg atgtctgcat cacaggcgtc gctatcccag tcaatactaa agcggtgcag  46860
gaactaaaga ttactgatga cttaggcgtg ccacgaggcc tgagacgacg cgcgtagaca  46920
gtttttttgaa atcattatca aagtgatggc ctccgctgaa gcctatcacc tctgcgccgg  46980
tctgtcggag agatgggcaa gcattattac ggtcttcgcg cccgtacatg cattggacga  47040
ttgcagggtc aatggatctg agatcatcca gaggattgcc gcccttacct tccgtttcga  47100
gttggagcca gcccctaaat gagacgacat agtcgacttg atgtgacaat gccaagagag  47160
agatttgctt aacccgattt ttttgctcaa gcgtaagcct attgaagctt gccggcatga  47220
cgtccgcgcc gaaagaatat cctacaagta aaacattctg cacaccgaaa tgcttggtgt  47280
agacatcgat tatgtgacca agatccttag cagtttcgct tggggaccgc tccgaccaga  47340
aataccgaag tgaactgacg ccaatgacag gaatcccttc cgtctgcaga taggtaccat  47400
cgatagatct gctgcctcgc gcgtttcggt gatgacggtg aaaacctctg acacatgcag  47460
ctcccggaga cggtcacagc ttgtctgtaa gcggatgccg ggagcagaca agcccgtcag  47520
ggcgcgtcag cgggtgttgg cgggtgtcgg ggcgcagcca tgacccagtc acgtagcgat  47580
agcggagtgt atactggctt aactatgcgg catcagagca gattgtactg agagtgcacc  47640
atatgcggtg tgaaataccg cacagatgcg taaggagaaa ataccgcatc aggcgctctt  47700
ccgcttcctc gctcactgac tcgctgcgct cggtcgttcg gctgcggcga gcggtatcag  47760
ctcactcaaa ggcggtaata cggttatcca cagaatcagg ggataacgca ggaaagaaca  47820
tgtgagcaaa aggccagcaa aaggccagga accgtaaaaa ggccgcgttg ctggcgtttt  47880
tccataggct ccgcccccct gacgagcatc acaaaaatcg acgctcaagt cagaggtggc  47940
gaaacccgac aggactataa agataccagg cgtttccccc tggaagctcc ctcgtgcgct  48000
ctcctgttcc gaccctgccg cttaccggat acctgtccgc ctttctccct tcgggaagcg  48060
tggcgctttc tcatagctca cgctgtaggt atctcagttc ggtgtaggtc gttcgctcca  48120
agctgggctg tgtgcacgaa ccccccgttc agcccgaccg ctgcgcctta tccggtaact  48180
atcgtcttga gtccaacccg gtaagacacg acttatcgcc actggcagca gccactggta  48240
acaggattag cagagcgagg tatgtaggcg gtgctacaga gttcttgaag tggtggccta  48300
```

```
actacggcta cactagaagg acagtatttg gtatctgcgc tctgctgaag ccagttacct  48360
tcggaaaaag agttggtagc tcttgatccg gcaaacaaac caccgctggt agcggtggtt  48420
tttttgtttg caagcagcag attacgcgca gaaaaaaagg atctcaagaa gatcctttga  48480
tcttttctac ggggtctgac gctcagtgga acgaaaactc acgttaaggg attttggtca  48540
tgagattatc aaaaaggatc ttcacctaga tccttttaaa ttaaaaatga agttttaaat  48600
caatctaaag tatatatgag taaacttggt ctgacagtta ccaatgctta atcagtgagg  48660
cacctatctc agcgatctgt ctatttcgtt catccatagt tgcctgactc cccgtcgtgt  48720
agataactac gatacgggag ggcttaccat ctggccccag tgctgcaatg ataccgcgag  48780
acccacgctc accggctcca gatttatcag caataaacca gccagccgga agggccgagc  48840
gcagaagtgg tcctgcaact ttatccgcct ccatccagtc tattaattgt tgccgggaag  48900
ctagagtaag tagttcgcca gttaatagtt tgcgcaacgt tgttgccatt gctgcagggg  48960
gggggggggg gggggacttc cattgttcat tccacggaca aaaacagaga aaggaaacga  49020
cagaggccaa aaagcctcgc tttcagcacc tgtcgtttcc tttcttttca gagggtattt  49080
taaataaaaa cattaagtta tgacgaagaa gaacggaaac gccttaaacc ggaaaatttt  49140
cataaatagc gaaaacccgc gaggtcgccg ccccgtaacc tgtcggatca ccggaaagga  49200
cccgtaaagt gataatgatt atcatctaca tatcacaacg tgcgtggagg ccatcaaacc  49260
acgtcaaata atcaattatg acgcaggtat cgtattaatt gatctgcatc aacttaacgt  49320
aaaaacaact tcagacaata caaatcagcg acactgaata cggggcaacc tcatgtcccc  49380
cccccccccc cccctgcagg catcgtggtg tcacgctcgt cgtttggtat ggcttcattc  49440
agctccggtt cccaacgatc aaggcgagtt acatgatccc ccatgttgtg caaaaaagcg  49500
gttagctcct tcggtcctcc gatcgttgtc agaagtaagt tggccgcagt gttatcactc  49560
atggttatgg cagcactgca taattctctt actgtcatgc catccgtaag atgcttttct  49620
gtgactggtg agtactcaac caagtcattc tgagaatagt gtatgcggcg accgagttgc  49680
tcttgcccgg cgtcaacacg ggataatacc gcgccacata gcagaacttt aaaagtgctc  49740
atcattggaa aacgttcttc ggggcgaaaa ctctcaagga tcttaccgct gttgagatcc  49800
agttcgatgt aacccactcg tgcacccaac tgatcttcag catcttttac tttcaccagc  49860
gtttctgggt gagcaaaaac aggaaggcaa aatgccgcaa aaaagggaat aagggcgaca  49920
cggaaatgtt gaatactcat actcttcctt tttcaatatt attgaagcat ttatcagggt  49980
tattgtctca tgagcggata catatttgaa tgtatttaga aaaataaaca aataggggtt  50040
ccgcgcacat ttccccgaaa agtgccacct gacgtctaag aaaccattat tatcatgaca  50100
ttaacctata aaaataggcg tatcacgagg ccctttcgtc ttcaagaatt ggtcgacgat  50160
cttgctgcgt tcggatattt tcgtggagtt cccgccacag acccggattg aaggcgagat  50220
ccagcaactc gcgccagatc atcctgtgac ggaactttgg cgcgtgatga ctggccagga  50280
cgtcggccga aagagcgaca agcagatcac gcttttcgac agcgtcggat ttgcgatcga  50340
ggatttttcg gcgctgcgct acgtccgcga ccgcgttgag ggatcaagcc acagcagccc  50400
actcgacctt ctagccgacc cagacgagcc aagggatctt tttggaatgc tgctccgtcg  50460
tcaggctttc cgacgtttgg gtggttgaac agaagtcatt atcgtacgga atgccaagca  50520
ctcccgaggg gaaccctgtg gttggcatgc acatacaaat ggacgaacgg ataaaccttt  50580
tcacgccctt ttaaatatcc gttattctaa taaacgctct tttctcttag gtttacccgc  50640
caatatatcc tgtcaaacac tgatagttta aactgaaggc gggaaacgac aatctgatca  50700
```

```
tgagcggaga attaagggag tcacgttatg acccccgccg atgacgcggg acaagccgtt  50760

ttacgtttgg aactgacaga accgcaacgt tgaaggagcc actcagcaag ctggtacgat  50820

tgtaatacga ctcactatag ggcgaattga gcgctgttta aacgctcttc aactggaaga  50880

gcggttacta ccggttaagt gactagggtc                                   50910
```

<210> SEQ ID NO 6
<211> LENGTH: 50751
<212> TYPE: DNA
<213> ORGANISM: Artificial Sequence
<220> FEATURE:
<223> OTHER INFORMATION: PINII terminator control vector

<400> SEQUENCE: 6

```
acgtgaccct agtcacttag gttaccagag ctggtcacct ttgtccacca agatggaact     60

gcggccgctc attaattaag tcaggcgcgc ctctagttga agacacgttc atgtcttcat    120

cgtaagaaga cactcagtag tcttcggcca gaatggccat ctggattcag caggcctaga    180

aggccattta aatcctgagg atctggtctt cctaaggacc cgggatatcg ctatcaactt    240

tgtatagaaa agttgggccg aattcgagct cggtacggcc agaatggccc ggaccgggtt    300

accgaattcg agctcggtac cactagtaag cttgccgcaa ttcgcaaaac acacctagac    360

tagatttgtt ttgctaaccc aattgatatt aattatatat gattaatatt tatatgtata    420

tggatttggt taatgaaatg catctggttc atcaaagaat tataaagaca cgtgacattc    480

atttaggata agaaatatgg atgatctctt tctcttttat tcagataact agtaattaca    540

cataacacac aactttgatg cccacattat agtgattagc atgtcactat gtgtgcatcc    600

ttttatttca tacattaatt aagttggcca atccagaaga tggacaagtc tggatcttca    660

ttgtttgcct ccctgctgcg gtttttcacc gaagttcatg ccagtccagc gtttttgcag    720

cagaaaagcc gccgacttcg gtttgcggtc gcgagtgaag atccctttct tgttaccgcc    780

aacgcgcaat atgccttgcg aggtcgcaaa atcggcgaaa ttccatacct gttcaccgac    840

gacggcgctg acgcgatcaa agacgcggtg atacatatcc agccatgcac actgatactc    900

ttcactccac atgtcggtgt acattgagtg cagcccggct aacgtatcca cgccgtattc    960

ggtgatgata atcggctgat gcagtttctc ctgccaggcc agaagttctt tttccagtac   1020

cttctctgcc gtttccaaat cgccgctttg gacataccat ccgtaataac ggttcaggca   1080

cagcacatca aagagatcgc taatggtatc ggtgtgagcg tcgcagaaca ttacattgac   1140

gcaggtgatc ggacgcgtcg ggtcgagttt acgcgttgct tccgccagtg gcgcgaaata   1200

ttcccgtgca ccttgcggac gggtatccgg ttcgttggca atactccaca tcaccacgct   1260

tgggtggttt ttgtcacgcg ctatcagctc tttaatcgcc tgtaagtgcg cttgctgagt   1320

ttccccgttg actgcctctt cgctgtacag ttctttcggc ttgttgcccg cttcgaaacc   1380

aatcctaaa gagaggttaa agccgacagc agcagtttca tcaatcacca cgatgccatg    1440

ttcatctgcc cagtcgagca tctcttcagc gtaagggtaa tgcgaggtac ggtaggagtt   1500

ggccccaatc cagtccatta atgcgtggtc gtgcaccatc agcacgttat cgaatccttt   1560

gccacgcaag tccgcatctt catgacgacc aaagccagta aagtagaacg gtttgtggtt   1620

aatcaggaac tgttggccct tcactgccac tgaccggatg ccgacgcgaa gcgggtagat   1680

atcacactct gtctggcttt tggctgtgac gcacagttca tagagataac cttcacccgg   1740

ttgccagagg tgcggattca ccacttgcaa agtcccgcta gtgccttgtc cagttgcaac   1800

cacctgttga tccgcatcac gcagttcaac gctgacatca ccattggcca ccacctgcca   1860
```

```
gtcaacagac gcgtggttac agtcttgcgc gacatgcgtc accacggtga tatcgtccac   1920
ccaggtgttc ggcgtggtgt agagcattac gctgcgatgg attccggcat agttaaagaa   1980
atcatggaag taagactgct ttttcttgcc gttttcgtcg gtaatcacca ttcccggcgg   2040
gatagtctgc cagttcagtt cgttgttcac acaaacggtg atacctgcac atcaacaaat   2100
tttggtcata tattagaaaa gttataaatt aaaatataca cacttataaa ctacagaaaa   2160
gcaattgcta tatactacat tcttttattt tgaaaaaaat atttgaaata ttatattact   2220
actaattaat gataattatt atatatatat caaaggtaga agcagaaact tacgtacact   2280
tttcccggca ataacatacg gcgtgacatc ggcttcaaat ggcgtatagc cgccctgatg   2340
ctccatcact tcctgattat tgacccacac tttgccgtaa tgagtgaccg catcgaaacg   2400
cagcacgata cgctggcctg cccaaccttt cggtataaag acttcgcgct gataccagac   2460
gttgcccgca taattacgaa tatctgcatc ggcgaactga tcgttaaaac tgcctggcac   2520
agcaattgcc cggctttctt gtaacgcgct ttcccaccaa cgctgatcaa ttccacagtt   2580
ttcgcgatcc agactgaatg cccacaggcc gtcgagtttt ttgatttcac gggttggggt   2640
ttctacagga cggaccatgg tgtcgtgtgg atccaaattg tatgcaaggt gaatgacttt   2700
cttttcgtaa actagatagg agtactcctc caggatgctt aacccgtatt gacgtacaga   2760
ggtctatgat ccttttgttt ataaaggagc ttgtagttca gtcagtctta tacttcacga   2820
tgcccatgtt tctatatagg atattatctt ggctttgtaa gtacttcacg caggttatgt   2880
tctgtttcta ggatattatc ctcatacatg cgaagaacca atttttcccc cattctcttc   2940
gggtactttt tcttgggtag gcatgctctc ttggaccaac tagcataaaa cataatcatt   3000
tttccctaca gccttgacca gctataatcg aaatcatgct catttttcta agaaagactg   3060
aatacagctc caatttaaac aatttaaatc ataaacttgt aactcaatta gagaaaagca   3120
gagcccttcg gctcctatct aaaggaatta ccccatgaaa gccataaaaa cgaaccttgc   3180
tctgatacca gacgggtcta cgctcgcgga actaggatct tgcgctctac tcgcacaaag   3240
tgaactcgca caaagtgtgt ttcaagcaca gaagttttta tttctcaaat caggagtaaa   3300
ctcgcgttgt ggtgcgtgtt tgcaacctga atacaaggct ccttatatag agagttgtgg   3360
agctttctgg catcgttagg tggcatccac caataatgca gataagcatc atcacatgtc   3420
tctggcctaa caactttgcg taagaatcct gcaaagttac taaaggtcat cgtgcgtgac   3480
tagacaacgc acaccgacaa acttaaaata aagagacatt atactttgtc tcctctttac   3540
ataaagtgag tggtatccag ctcactccgc atcttatcag tcttcacacc ggttggtatc   3600
aacacgtggt aggggtccgc cacttccgct tcagtcatca ttactgatat ccagcagatc   3660
tagagcatct tcaataagat attcttgttc tgcacgcaga ttttcttgct ccctcagtaa   3720
ttcctcccac agtgagtctt ctgatatttc ttcaagtttc ttctcccatc tgatcttttc   3780
ctgcacaaac gagtcaattt ggtctttcca gacccaagta aaacaagtgt tagtttcaca   3840
ggagtaaaac tccctgtcag gatttctgga tgttctggag atcttcagtt ttgctggttt   3900
attgcatcca catttgaaaa ccggctcttc acttagtgtt agcacattga tttgatgcaa   3960
cctgtagcct ttgctcaacc agtcttcata tctttttaca acatcattaa ctctctgttt   4020
tgcatcggtg tttcccttgt gaaatacctc ctccactgca ttgatcaaca caccttcaga   4080
ttgatgcttt tccggatgga gaataatctt taccagtctt gacagagtgt ctgctaaaac   4140
gttgtccttt ccgtcaatgt gttcaaactt aatctcaaga cctgtcccgg taatgtaatc   4200
tgtgaaggca agccatctga ctcttgatgg tttatgatca ctgcttttct tgtaaaagct   4260
```

-continued

```
cactattgct tgactgtcag ttctgattat gagctctttg taagcttggt cacccggtcc   4320
gggcctagaa ggccagcttc ggccgccccg ggcaacttta ttatacaaag ttgatagata   4380
tcggaccgat taaactttaa ttcggtccga agcttgcatg cctgcagtgc agcgtgaccc   4440
ggtcgtgccc ctctctagag ataatgagca ttgcatgtct aagttataaa aaattaccac   4500
atattttttt tgtcacactt gtttgaagtg cagtttatct atctttatac atatatttaa   4560
actttactct acgaataata taatctatag tactacaata atatcagtgt tttagagaat   4620
catataaatg aacagttaga catggtctaa aggacaattg agtattttga caacaggact   4680
ctacagtttt atcttttttag tgtgcatgtg ttctcctttt tttttgcaaa tagcttcacc   4740
tatataatac ttcatccatt ttattagtac atccatttag ggtttagggt taatggtttt   4800
tatagactaa ttttttttagt acatctattt tattctattt tagcctctaa attaagaaaa   4860
ctaaaactct attttagttt ttttatttaa taatttagat ataaaataga ataaaataaa   4920
gtgactaaaa attaaacaaa taccctttaa gaaattaaaa aaactaagga aacatttttc   4980
ttgtttcgag tagataatgc cagcctgtta aacgccgtcg acgagtctaa cggacaccaa   5040
ccagcgaacc agcagcgtcg cgtcgggcca agcgaagcag acggcacggc atctctgtcg   5100
ctgcctctgg acccctctcg agagttccgc tccaccgttg gacttgctcc gctgtcggca   5160
tccagaaatt gcgtggcgga gcggcagacg tgagccggca cggcaggcgg cctcctcctc   5220
ctctcacggc accggcagct acgggggatt cctttcccac cgctccttcg ctttcccttc   5280
ctcgcccgcc gtaataaata gacacccccct ccacaccctc tttccccaac ctcgtgttgt   5340
tcggagcgca cacacacaca accagatctc ccccaaatcc acccgtcggc acctccgctt   5400
caaggtacgc cgctcgtcct cccccccccc cctctctacc ttctctagat cggcgttccg   5460
gtccatgcat ggttagggcc cggtagttct acttctgttc atgtttgtgt tagatccgtg   5520
tttgtgttag atccgtgctg ctagcgttcg tacacggatg cgacctgtac gtcagacacg   5580
ttctgattgc taacttgcca gtgtttctct ttggggaatc ctgggatggc tctagccgtt   5640
ccgcagacgg gatcgatttc atgatttttt ttgtttcgtt gcatagggtt tggtttgccc   5700
ttttccttta tttcaatata tgccgtgcac ttgtttgtcg ggtcatcttt tcatgctttt   5760
ttttgtcttg gttgtgatga tgtggtctgg ttgggcggtc gttctagatc ggagtagaat   5820
tctgtttcaa actacctggt ggatttatta attttggatc tgtatgtgtg tgccatacat   5880
attcatagtt acgaattgaa gatgatggat ggaaatatcg atctaggata ggtatacatg   5940
ttgatgcggg ttttactgat gcatatacag agatgctttt tgttcgcttg gttgtgatga   6000
tgtggtgtgg ttgggcggtc gttcattcgt tctagatcgg agtagaatac tgtttcaaac   6060
tacctggtgt atttattaat tttggaactg tatgtgtgtg tcatacatct tcatagttac   6120
gagtttaaga tggatggaaa tatcgatcta ggataggtat acatgttgat gtgggtttta   6180
ctgatgcata tacatgatgg catatgcagc atctattcat atgctctaac cttgagtacc   6240
tatctattat aataaacaag tatgttttat aattattttg atcttgatat acttggatga   6300
tggcatatgc agcagctata tgtggatttt tttagccctg ccttcatacg ctatttattt   6360
gcttggtact gtttcttttg tcgatgctca ccctgttgtt tggtgttact tctgcaggtc   6420
gactttaact tagcctagga tccacacgac accatgtccc ccgagcgccg ccccgtcgag   6480
atccgcccgg ccaccgccgc cgacatggcc gccgtgtgcg acatcgtgaa ccactacatc   6540
gagacctcca ccgtgaactt ccgcaccgag ccgcagaccc cgcaggagtg gatcgacgac   6600
ctggagcgcc tccaggaccg ctacccgtgg ctcgtggccg aggtggaggg cgtggtggcc   6660
```

```
ggcatcgcct acgccggccc gtggaaggcc cgcaacgcct acgactggac cgtggagtcc   6720
accgtgtacg tgtcccaccg ccaccagcgc ctcggcctcg gctccaccct ctacacccac   6780
ctcctcaaga gcatggaggc ccagggcttc aagtccgtgg tggccgtgat cggcctcccg   6840
aacgacccgt ccgtgcgcct ccacgaggcc ctcggctaca ccgcccgcgg caccctccgc   6900
gccgccggct acaagcacgg cggctggcac gacgtcggct tctggcagcg cgacttcgag   6960
ctgccggccc cgccgcgccc ggtgcgcccg gtgacgcaga tctgagtcga aacctagact   7020
tgtccatctt ctggattggc caacttaatt aatgtatgaa ataaaaggat gcacacatag   7080
tgacatgcta atcactataa tgtgggcatc aaagttgtgt gttatgtgta attactagtt   7140
atctgaataa aagagaaaga gatcatccat atttcttatc ctaaatgaat gtcacgtgtc   7200
tttataattc tttgatgaac cagatgcatt tcattaacca aatccatata catataaata   7260
ttaatcatat ataattaata tcaattgggt tagcaaaaca aatctagtct aggtgtgttt   7320
tgcgaatgcg gccgataagt gactagggtc acgtgaccct agtcacttag gtaccgagct   7380
cgaattcatt ccgattaatc gtggcctctt gctcttcagg atgaagagct atgtttaaac   7440
gtgcaagcgc tactagacaa ttcagtacat taaaaacgtc cgcaatgtgt tattaagttg   7500
tctaagcgtc aatttgttta caccacaata tatcctgcca ccagccagcc aacagctccc   7560
cgaccggcag ctcggcacaa aatcaccact cgatacaggc agcccatcag tccgggacgg   7620
cgtcagcggg agagccgttg taaggcggca gactttgctc atgttaccga tgctattcgg   7680
aagaacggca actaagctgc cgggtttgaa acacggatga tctcgcggag ggtagcatgt   7740
tgattgtaac gatgacagag cgttgctgcc tgtgatcaaa tatcatctcc ctcgcagaga   7800
tccgaattat cagccttctt attcatttct cgcttaaccg tgacaggctg tcgatcttga   7860
gaactatgcc gacataatag gaaatcgctg gataaagccg ctgaggaagc tgagtggcgc   7920
tatttcttta gaagtgaacg ttgacgatcg tcgaccgtac cccgatgaat taattcggac   7980
gtacgttctg aacacagctg gatacttact tgggcgattg tcatacatga catcaacaat   8040
gtacccgttt gtgtaaccgt ctcttggagg ttcgtatgac actagtggtt cccctcagct   8100
tgcgactaga tgttgaggcc taacatttta ttagagagca ggctagttgc ttagatacat   8160
gatcttcagg ccgttatctg tcagggcaag cgaaaattgg ccatttatga cgaccaatgc   8220
cccgcagaag ctcccatctt tgccgccata gacgccgcgc ccccttttg gggtgtagaa   8280
catccttttg ccagatgtgg aaaagaagtt cgttgtccca ttgttggcaa tgacgtagta   8340
gccggcgaaa gtgcgagacc catttgcgct atatataagc ctacgatttc cgttgcgact   8400
attgtcgtaa ttggatgaac tattatcgta gttgctctca gagttgtcgt aatttgatgg   8460
actattgtcg taattgctta tggagttgtc gtagttgctt ggagaaatgt cgtagttgga   8520
tggggagtag tcatagggaa gacgagcttc atccactaaa acaattggca ggtcagcaag   8580
tgcctgcccc gatgccatcg caagtacgag gcttagaacc accttcaaca gatcgcgcat   8640
agtcttcccc agctctctaa cgcttgagtt aagccgcgcc gcgaagcggc gtcggcttga   8700
acgaattgtt agacattatt tgccgactac cttggtgatc tcgcctttca cgtagtgaac   8760
aaattcttcc aactgatctg cgcgcgaggc caagcgatct tcttgtccaa gataagcctg   8820
cctagcttca agtatgacgg gctgatactg ggccggcagg cgctccattg cccagtcggc   8880
agcgacatcc ttcggcgcga ttttgccggt tactgcgctg taccaaatgc gggacaacgt   8940
aagcactaca tttcgctcat cgccagccca gtcgggcggc gagttccata gcgttaaggt   9000
ttcatttagc gcctcaaata gatcctgttc aggaaccgga tcaaagagtt cctccgccgc   9060
```

-continued

```
tggacctacc aaggcaacgc tatgttctct tgcttttgtc agcaagatag ccagatcaat   9120
gtcgatcgtg gctggctcga agatacctgc aagaatgtca ttgcgctgcc attctccaaa   9180
ttgcagttcg cgcttagctg gataacgcca cggaatgatg tcgtcgtgca caacaatggt   9240
gacttctaca gcgcggagaa tctcgctctc tccaggggaa gccgaagttt ccaaaaggtc   9300
gttgatcaaa gctcgccgcg ttgtttcatc aagccttaca gtcaccgtaa ccagcaaatc   9360
aatatcactg tgtggcttca ggccgccatc cactgcggag ccgtacaaat gtacggccag   9420
caacgtcggt tcgagatggc gctcgatgac gccaactacc tctgatagtt gagtcgatac   9480
ttcggcgatc accgcttccc tcatgatgtt taactcctga attaagccgc gccgcgaagc   9540
ggtgtcggct tgaatgaatt gttaggcgtc atcctgtgct cccgagaacc agtaccagta   9600
catcgctgtt tcgttcgaga cttgaggtct agttttatac gtgaacaggt caatgccgcc   9660
gagagtaaag ccacattttg cgtacaaatt gcaggcaggt acattgttcg tttgtgtctc   9720
taatcgtatg ccaaggagct gtctgcttag tgcccacttt ttcgcaaatt cgatgagact   9780
gtgcgcgact cctttgcctc ggtgcgtgtg cgacacaaca atgtgttcga tagaggctag   9840
atcgttccat gttgagttga gttcaatctt cccgacaagc tcttggtcga tgaatgcgcc   9900
atagcaagca gagtcttcat cagagtcatc atccgagatg taatccttcc ggtaggggct   9960
cacacttctg gtagatagtt caaagccttg gtcggatagg tgcacatcga acacttcacg  10020
aacaatgaaa tggttctcag catccaatgt ttccgccacc tgctcaggga tcaccgaaat  10080
cttcatatga cgcctaacgc ctggcacagc ggatcgcaaa cctggcgcgg cttttggcac  10140
aaaaggcgtg acaggtttgc gaatccgttg ctgccacttg ttaacccttt tgccagattt  10200
ggtaactata atttatgtta gaggcgaagt cttgggtaaa aactggccta aaattgctgg  10260
ggatttcagg aaagtaaaca tcaccttccg gctcgatgtc tattgtagat atatgtagtg  10320
tatctacttg atcgggggat ctgctgcctc gcgcgtttcg gtgatgacgg tgaaaacctc  10380
tgacacatgc agctcccgga gacggtcaca gcttgtctgt aagcggatgc cgggagcaga  10440
caagcccgtc agggcgcgtc agcgggtgtt ggcgggtgtc ggggcgcagc catgacccag  10500
tcacgtagcg atagcggagt gtatactggc ttaactatgc ggcatcagag cagattgtac  10560
tgagagtgca ccatatgcgg tgtgaaatac cgcacagatg cgtaaggaga aaataccgca  10620
tcaggcgctc ttccgcttcc tcgctcactg actcgctgcg ctcggtcgtt cggctgcggc  10680
gagcggtatc agctcactca aaggcggtaa tacggttatc cacagaatca ggggataacg  10740
caggaaagaa catgtgagca aaaggccagc aaaaggccag gaaccgtaaa aaggccgcgt  10800
tgctggcgtt tttccatagg ctccgccccc ctgacgagca tcacaaaaat cgacgctcaa  10860
gtcagaggtg gcgaaacccg acaggactat aaagatacca ggcgtttccc cctggaagct  10920
ccctcgtgcg ctctcctgtt ccgaccctgc cgcttaccgg atacctgtcc gcctttctcc  10980
cttcgggaag cgtggcgctt tctcatagct cacgctgtag gtatctcagt tcggtgtagg  11040
tcgttcgctc caagctgggc tgtgtgcacg aaccccccgt tcagcccgac cgctgcgcct  11100
tatccggtaa ctatcgtctt gagtccaacc cggtaagaca cgacttatcg ccactggcag  11160
cagccactgg taacaggatt agcagagcga ggtatgtagg cggtgctaca gagttcttga  11220
agtggtggcc taactacggc tacactagaa ggacagtatt tggtatctgc gctctgctga  11280
agccagttac cttcggaaaa agagttggta gctcttgatc cggcaaacaa accaccgctg  11340
gtagcggtgg tttttttgtt tgcaagcagc agattacgcg cagaaaaaaa ggatctcaag  11400
aagatccttt gatcttttct acggggtctg acgctcagtg gaacgaaaac tcacgttaag  11460
```

```
ggattttggt catgagatta tcaaaaagga tcttcaccta gatcctttta aattaaaaat  11520
gaagttttaa atcaatctaa agtatatatg agtaaacttg gtctgacagt taccaatgct  11580
taatcagtga ggcacctatc tcagcgatct gtctatttcg ttcatccata gttgcctgac  11640
tccccgtcgt gtagataact acgatacggg agggcttacc atctggcccc agtgctgcaa  11700
tgataccgcg agacccacgc tcaccggctc cagatttatc agcaataaac cagccagccg  11760
gaagggccga gcgcagaagt ggtcctgcaa ctttatccgc ctccatccag tctattaatt  11820
gttgccggga agctagagta agtagttcgc cagttaatag tttgcgcaac gttgttgcca  11880
ttgctgcagg gggggggggg ggggggttcc attgttcatt ccacggacaa aaacagagaa  11940
aggaaacgac agaggccaaa aagctcgctt tcagcacctg tcgtttcctt tcttttcaga  12000
gggtatttta aataaaaaca ttaagttatg acgaagaaga acggaaacgc cttaaaccgg  12060
aaaatttca taaatagcga aaacccgcga ggtcgccgcc ccgtaacctg tcggatcacc  12120
ggaaaggacc cgtaaagtga taatgattat catctacata tcacaacgtg cgtggaggcc  12180
atcaaaccac gtcaaataat caattatgac gcaggtatcg tattaattga tctgcatcaa  12240
cttaacgtaa aaacaacttc agacaataca aatcagcgac actgaatacg gggcaacctc  12300
atgtcccccc cccccccccc cctgcaggca tcgtggtgtc acgctcgtcg tttggtatgg  12360
cttcattcag ctccggttcc caacgatcaa ggcgagttac atgatccccc atgttgtgca  12420
aaaaagcggt tagctccttc ggtcctccga tcgttgtcag aagtaagttg gccgcagtgt  12480
tatcactcat ggttatggca gcactgcata attctcttac tgtcatgcca tccgtaagat  12540
gcttttctgt gactggtgag tactcaacca agtcattctg agaatagtgt atgcggcgac  12600
cgagttgctc ttgcccggcg tcaacacggg ataataccgc gccacatagc agaactttaa  12660
aagtgctcat cattggaaaa cgttcttcgg ggcgaaaact ctcaaggatc ttaccgctgt  12720
tgagatccag ttcgatgtaa cccactcgtg cacccaactg atcttcagca tcttttactt  12780
tcaccagcgt ttctgggtga gcaaaaacag gaaggcaaaa tgccgcaaaa aagggaataa  12840
gggcgacacg gaaatgttga atactcatac tcttcctttt tcaatattat tgaagcattt  12900
atcagggtta ttgtctcatg agcggataca tatttgaatg tatttagaaa aataaacaaa  12960
taggggttcc gcgcacattt ccccgaaaag tgccacctga cgtctaagaa accattatta  13020
tcatgacatt aacctataaa aataggcgta tcacgaggcc ctttcgtctt caagaattcg  13080
gagcttttgc cattctcacc ggattcagtc gtcactcatg gtgatttctc acttgataac  13140
cttatttttg acgaggggaa attaataggt tgtattgatg ttggacgagt cggaatcgca  13200
gaccgatacc aggatcttgc catcctatgg aactgcctcg gtgagttttc tccttcatta  13260
cagaaacggc tttttcaaaa atatggtatt gataatcctg atatgaataa attgcagttt  13320
catttgatgc tcgatgagtt tttctaatca gaattggtta attggttgta acactggcag  13380
agcattacgc tgacttgacg ggacggcggc tttgttgaat aaatcgaact tttgctgagt  13440
tgaaggatca gatcacgcat cttcccgaca acgcagaccg ttccgtggca aagcaaaagt  13500
tcaaaatcac caactggtcc acctacaaca aagctctcat caaccgtggc tccctcactt  13560
tctggctgga tgatggggcg attcaggcct ggtatgagtc agcaacacct tcttcacgag  13620
gcagacctca gcgccagaag gccgccagag aggccgagcg cggccgtgag gcttggacgc  13680
tagggcaggg catgaaaaag cccgtagcgg gctgctacgg gcgtctgacg cggtggaaag  13740
ggggagggga tgttgtctac atggctctgc tgtagtgagt gggttgcgct ccggcagcgg  13800
tcctgatcaa tcgtcaccct ttctcggtcc ttcaacgttc ctgacaacga gcctcctttt  13860
```

```
cgccaatcca tcgacaatca ccgcgagtcc ctgctcgaac gctgcgtccg gaccggcttc  13920
gtcgaaggcg tctatcgcgg cccgcaacag cggcgagagc ggagcctgtt caacggtgcc  13980
gccgcgctcg ccggcatcgc tgtcgccggc ctgctcctca agcacggccc caacagtgaa  14040
gtagctgatt gtcatcagcg cattgacggc gtccccggcc gaaaaacccg cctcgcagag  14100
gaagcgaagc tgcgcgtcgg ccgtttccat ctgcggtgcg cccggtcgcg tgccggcatg  14160
gatgcgcgcg ccatcgcggt aggcgagcag cgcctgcctg aagctgcggg cattcccgat  14220
cagaaatgag cgccagtcgt cgtcggctct cggcaccgaa tgcgtatgat tctccgccag  14280
catggcttcg gccagtgcgt cgagcagcgc ccgcttgttc ctgaagtgcc agtaaagcgc  14340
cggctgctga acccccaacc gttccgccag tttgcgtgtc gtcagaccgt ctacgccgac  14400
ctcgttcaac aggtccaggg cggcacggat cactgtattc ggctgcaact ttgtcatgct  14460
tgacacttta tcactgataa acataatatg tccaccaact tatcagtgat aaagaatccg  14520
cgcgttcaat cggaccagcg gaggctggtc cggaggccag acgtgaaacc caacataccc  14580
ctgatcgtaa ttctgagcac tgtcgcgctc gacgctgtcg gcatcggcct gattatgccg  14640
gtgctgccgg gcctcctgcg cgatctggtt cactcgaacg acgtcaccgc ccactatggc  14700
attctgctgg cgctgtatgc gttggtgcaa tttgcctgcg cacctgtgct gggcgcgctg  14760
tcggatcgtt tcgggcggcg gccaatcttg ctcgtctcgc tggccggcgc cactgtcgac  14820
tacgccatca tggcgacagc gcctttcctt tgggttctct atatcgggcg gatcgtggcc  14880
ggcatcaccg gggcgactgg ggcggtagcc ggcgcttata ttgccgatat cactgatggc  14940
gatgagcgcg cgcggcactt cggcttcatg agcgcctgtt tcgggttcgg gatggtcgcg  15000
ggacctgtgc tcggtgggct gatgggcggt ttctcccccc acgctccgtt cttcgccgcg  15060
gcagccttga acggcctcaa tttcctgacg ggctgtttcc ttttgccgga gtcgcacaaa  15120
ggcgaacgcc ggccgttacg ccgggaggct ctcaacccgc tcgcttcgtt ccggtgggcc  15180
cggggcatga ccgtcgtcgc cgccctgatg gcggtcttct tcatcatgca acttgtcgga  15240
caggtgccgg ccgcgctttg ggtcattttc ggcgaggatc gctttcactg ggacgcgacc  15300
acgatcggca tttcgcttgc cgcatttggc attctgcatt cactcgccca ggcaatgatc  15360
accggccctg tagccgcccg gctcggcgaa aggcgggcac tcatgctcgg aatgattgcc  15420
gacggcacag gctacatcct gcttgccttc gcgacacggg gatggatggc gttcccgatc  15480
atggtcctgc ttgcttcggg tggcatcgga atgccggcgc tgcaagcaat gttgtccagg  15540
caggtggatg aggaacgtca ggggcagctg caaggctcac tggcggcgct caccagcctg  15600
acctcgatcg tcggacccct cctcttcacg gcgatctatg cggcttctat aacaacgtgg  15660
aacgggtggg catggattgc aggcgctgcc ctctacttgc tctgcctgcc ggcgctgcgt  15720
cgcgggcttt ggagcggcgc agggcaacga gccgatcgct gatcgtggaa acgataggcc  15780
tatgccatgc gggtcaaggc gacttccggc aagctatacg cgccctagga gtgcggttgg  15840
aacgttggcc cagccagata ctcccgatca cgagcaggac gccgatgatt tgaagcgcac  15900
tcagcgtctg atccaagaac aaccatccta gcaacacggc ggtccccggg ctgagaaagc  15960
ccagtaagga aacaactgta ggttcgagtc gcgagatccc ccggaaccaa aggaagtagg  16020
ttaaacccgc tccgatcagg ccgagccacg ccaggccgag aacattggtt cctgtaggca  16080
tcgggattgg cggatcaaac actaaagcta ctggaacgag cagaagtcct ccggccgcca  16140
gttgccaggc ggtaaaggtg agcagaggca cgggaggttg ccacttgcgg gtcagcacgg  16200
ttccgaacgc catggaaacc gcccccgcca ggcccgctgc gacgccgaca ggatctagcg  16260
```

```
ctgcgtttgg tgtcaacacc aacagcgcca cgcccgcagt tccgcaaata gcccccagga  16320
ccgccatcaa tcgtatcggg ctacctagca gagcggcaga gatgaacacg accatcagcg  16380
gctgcacagc gcctaccgtc gccgcgaccc cgcccggcag gcggtagacc gaaataaaca  16440
acaagctcca gaatagcgaa atattaagtg cgccgaggat gaagatgcgc atccaccaga  16500
ttcccgttgg aatctgtcgg acgatcatca cgagcaataa acccgccggc aacgcccgca  16560
gcagcatacc ggcgacccct cggcctcgct gttcgggctc cacgaaaacg ccggacagat  16620
gcgccttgtg agcgtccttg ggccgtcct cctgtttgaa gaccgacagc ccaatgatct  16680
cgccgtcgat gtaggcgccg aatgccacgg catctcgcaa ccgttcagcg aacgcctcca  16740
tgggcttttt ctcctcgtgc tcgtaaacgg acccgaacat ctctggagct ttcttcaggg  16800
ccgacaatcg gatctcgcgg aaatcctgca cgtcggccgc tccaagccgt cgaatctgag  16860
ccttaatcac aattgtcaat tttaatcctc tgtttatcgg cagttcgtag agcgcgccgt  16920
gcgtcccgag cgatactgag cgaagcaagt gcgtcgagca gtgcccgctt gttcctgaaa  16980
tgccagtaaa gcgctggctg ctgaaccccc agccggaact gaccccacaa ggccctagcg  17040
tttgcaatgc accaggtcat cattgaccca ggcgtgttcc accaggccgc tgcctcgcaa  17100
ctcttcgcag gcttcgccga cctgctcgcg ccacttcttc acgcgggtgg aatccgatcc  17160
gcacatgagg cggaaggttt ccagcttgag cgggtacggc tcccggtgcg agctgaaata  17220
gtcgaacatc cgtcgggccg tcggcgacag cttgcggtac ttctcccata tgaatttcgt  17280
gtagtggtcg ccagcaaaca gcacgacgat ttcctcgtcg atcaggacct ggcaacggga  17340
cgttttcttg ccacggtcca ggacgcggaa gcggtgcagc agcgacaccg attccaggtg  17400
cccaacgcgg tcggacgtga agcccatcgc cgtcgcctgt aggcgcgaca ggcattcctc  17460
ggccttcgtg taataccggc cattgatcga ccagcccagg tcctggcaaa gctcgtagaa  17520
cgtgaaggtg atcggctcgc cgataggggt gcgcttcgcg tactccaaca cctgctgcca  17580
caccagttcg tcatcgtcgg cccgcagctc gacgccggtg taggtgatct tcacgtcctt  17640
gttgacgtgg aaaatgacct tgttttgcag cgcctcgcgc gggattttct tgttgcgcgt  17700
ggtgaacagg gcagagcggg ccgtgtcgtt tggcatcgct cgcatcgtgt ccggccacgg  17760
cgcaatatcg aacaaggaaa gctgcatttc cttgatctgc tgcttcgtgt gtttcagcaa  17820
cgcggcctgc ttggcctcgc tgacctgttt tgccaggtcc tcgccggcgg tttttcgctt  17880
cttggtcgtc atagttcctc gcgtgtcgat ggtcatcgac ttcgccaaac ctgccgcctc  17940
ctgttcgaga cgacgcgaac gctccacggc ggccgatggc gcgggcaggg caggggggagc  18000
cagttgcacg ctgtcgcgct cgatcttggc cgtagcttgc tggaccatcg agccgacgga  18060
ctggaaggtt tcgcggggcg cacgcatgac ggtgcggctt gcgatggttt cggcatcctc  18120
ggcggaaaac cccgcgtcga tcagttcttg cctgtatgcc ttccggtcaa acgtccgatt  18180
cattcaccct ccttgcggga ttgccccgac tcacgccggg gcaatgtgcc cttattcctg  18240
atttgacccg cctggtgcct tggtgtccag ataatccacc ttatcggcaa tgaagtcggt  18300
cccgtagacc gtctggccgt ccttctcgta cttggtattc cgaatcttgc cctgcacgaa  18360
taccagcgac cccttgccca aatacttgcc gtgggcctcg gcctgagagc caaaacactt  18420
gatgcggaag aagtcggtgc gctcctgctt gtcgccggca tcgttgcgcc actcttcatt  18480
aaccgctata tcgaaaattg cttgcggctt gttagaattg ccatgacgta cctcggtgtc  18540
acgggtaaga ttaccgataa actggaactg attatggctc atatcgaaag tctccttgag  18600
aaaggagact ctagtttagc taaacattgg ttccgctgtc aagaacttta gcggctaaaa  18660
```

```
ttttgcgggc cgcgaccaaa ggtgcgaggg gcggcttccg ctgtgtacaa ccagatattt  18720

ttcaccaaca tccttcgtct gctcgatgag cggggcatga cgaaacatga gctgtcggag  18780

agggcagggg tttcaatttc gtttttatca gacttaacca acggtaaggc caacccctcg  18840

ttgaaggtga tggaggccat tgccgacgcc ctggaaactc ccctacctct tctcctggag  18900

tccaccgacc ttgaccgcga ggcactcgcg gagattgcgg gtcatccttt caagagcagc  18960

gtgccgcccg gatacgaacg catcagtgtg gttttgccgt cacataaggc gtttatcgta  19020

aagaaatggg gcgacgacac ccgaaaaaag ctgcgtggaa ggctctgacg ccaagggtta  19080

gggcttgcac ttccttcttt agccgctaaa acggcccctt ctctgcgggc cgtcggctcg  19140

cgcatcatat cgacatcctc aacggaagcc gtgccgcgaa tggcatcggg cgggtgcgct  19200

ttgacagttg ttttctatca gaacccctac gtcgtgcggt tcgattagct gtttgtcttg  19260

caggctaaac actttcggta tatcgtttgc ctgtgcgata atgttgctaa tgatttgttg  19320

cgtaggggtt actgaaaagt gagcgggaaa gaagagtttc agaccatcaa ggagcgggcc  19380

aagcgcaagc tggaacgcga catgggtgcg gacctgttgg ccgcgctcaa cgacccgaaa  19440

accgttgaag tcatgctcaa cgcggacggc aaggtgtggc acgaacgcct tggcgagccg  19500

atgcggtaca tctgcgacat gcggcccagc cagtcgcagg cgattataga aacggtggcc  19560

ggattccacg gcaaagaggt cacgcggcat tcgcccatcc tggaaggcga gttccccttg  19620

gatggcagcc gctttgccgg ccaattgccg ccggtcgtgg ccgcgccaac ctttgcgatc  19680

cgcaagcgcg cggtcgccat cttcacgctg gaacagtacg tcgaggcggg catcatgacc  19740

cgcgagcaat acgaggtcat taaaagcgcc gtcgcggcgc atcgaaacat cctcgtcatt  19800

ggcggtactg gctcgggcaa gaccacgctc gtcaacgcga tcatcaatga aatggtcgcc  19860

ttcaacccgt ctgagcgcgt cgtcatcatc gaggacaccg gcgaaatcca gtgcgccgca  19920

gagaacgccg tccaatacca caccagcatc gacgtctcga tgacgctgct gctcaagaca  19980

acgctgcgta tgcgccccga ccgcatcctg gtcggtgagg tacgtggccc cgaagccctt  20040

gatctgttga tggcctggaa caccgggcat gaaggaggtg ccgccaccct gcacgcaaac  20100

aaccccaaag cgggcctgag ccggctcgcc atgcttatca gcatgcaccc ggattcaccg  20160

aaacccattg agccgctgat tggcgaggcg gttcatgtgg tcgtccatat cgccaggacc  20220

cctagcggcc gtcgagtgca agaaattctc gaagttcttg gttacgagaa cggccagtac  20280

atcaccaaaa ccctgtaagg agtatttcca atgacaacgg ctgttccgtt ccgtctgacc  20340

atgaatcgcg gcattttgtt ctaccttgcc gtgttcttcg ttctcgctct cgcgttatcc  20400

gcgcatccgg cgatggcctc ggaaggcacc ggcggcagct tgccatatga gagctggctg  20460

acgaacctgc gcaactccgt aaccggcccg gtggccttcg cgctgtccat catcggcatc  20520

gtcgtcgccg gcggcgtgct gatcttcggc ggcgaactca acgccttctt ccgaaccctg  20580

atcttcctgg ttctggtgat ggcgctgctg gtcggcgcgc agaacgtgat gagcaccttc  20640

ttcggtcgtg gtgccgaaat cgcggccctc ggcaacgggg cgctgcacca ggtgcaagtc  20700

gcggcggcgg atgccgtgcg tgcggtagcg gctggacggc tcgcctaatc atggctctgc  20760

gcacgatccc catccgtcgc gcaggcaacc gagaaaacct gttcatgggt ggtgatcgtg  20820

aactggtgat gttctcgggc ctgatggcgt ttgcgctgat tttcagcgcc caagagctgc  20880

gggccaccgt ggtcggtctg atcctgtggt tcggggcgct ctatgcgttc cgaatcatgg  20940

cgaaggccga tccgaagatg cggttcgtgt acctgcgtca ccgccggtac aagccgtatt  21000

acccggcccg ctcgaccccg ttccgcgaga acaccaatag ccaagggaag caataccgat  21060
```

```
gatccaagca attgcgattg caatcgcggg cctcggcgcg cttctgttgt tcatcctctt  21120
tgcccgcatc cgcgcggtcg atgccgaact gaaactgaaa aagcatcgtt ccaaggacgc  21180
cggcctggcc gatctgctca actacgccgc tgtcgtcgat gacggcgtaa tcgtgggcaa  21240
gaacggcagc tttatggctg cctggctgta caagggcgat gacaacgcaa gcagcaccga  21300
ccagcagcgc gaagtagtgt ccgcccgcat caaccaggcc ctcgcgggcc tgggaagtgg  21360
gtggatgatc catgtggacg ccgtgcggcg tcctgctccg aactacgcgg agcggggcct  21420
gtcggcgttc cctgaccgtc tgacggcagc gattgaagaa gagcgctcgg tcttgccttg  21480
ctcgtcggtg atgtacttca ccagctccgc gaagtcgctc ttcttgatgg agcgcatggg  21540
gacgtgcttg gcaatcacgc gcacccccg gccgttttag cggctaaaaa agtcatggct  21600
ctgccctcgg gcggaccacg cccatcatga ccttgccaag ctcgtcctgc ttctcttcga  21660
tcttcgccag cagggcgagg atcgtggcat caccgaaccg cgccgtgcgc gggtcgtcgg  21720
tgagccagag tttcagcagg ccgcccaggc ggcccaggtc gccattgatg cgggccagct  21780
cgcggacgtg ctcatagtcc acgacgcccg tgattttgta gccctggccg acggccagca  21840
ggtaggccga caggctcatg ccggccgccg ccgccttttc ctcaatcgct cttcgttcgt  21900
ctggaaggca gtacaccttg ataggtgggc tgcccttcct ggttggcttg gtttcatcag  21960
ccatccgctt gccctcatct gttacgccgg cggtagccgg ccagcctcgc agagcaggat  22020
tcccgttgag caccgccagg tgcgaataag ggacagtgaa gaaggaacac ccgctcgcgg  22080
gtgggcctac ttcacctatc ctgcccggct gacgccgttg gatacaccaa ggaaagtcta  22140
cacgaaccct ttggcaaaat cctgtatatc gtgcgaaaaa ggatggatat accgaaaaaa  22200
tcgctataat gaccccgaag cagggttatg cagcggaaaa gcgctgcttc cctgctgttt  22260
tgtggaatat ctaccgactg gaaacaggca aatgcaggaa attactgaac tgaggggaca  22320
ggcgagagac gatgccaaag agctacaccg acgagctggc cgagtgggtt gaatcccgcg  22380
cggccaagaa gcgccggcgt gatgaggctg cggttgcgtt cctggcggtg agggcggatg  22440
tcgaggcggc gttagcgtcc ggctatgcgc tcgtcaccat ttgggagcac atgcgggaaa  22500
cggggaaggt caagttctcc tacgagacgt tccgctcgca cgccaggcgg cacatcaagg  22560
ccaagcccgc cgatgtgccc gcaccgcagg ccaaggctgc ggaacccgcg ccggcaccca  22620
agacgccgga gccacggcgg ccgaagcagg ggggcaaggc tgaaaagccg gcccccgctg  22680
cggccccgac cggcttcacc ttcaacccaa caccggacaa aaaggatcta ctgtaatggc  22740
gaaaattcac atggttttgc agggcaaggg cggggtcggc aagtcggcca tcgccgcgat  22800
cattgcgcag tacaagatgg acaaggggca gacacccttg tgcatcgaca ccgacccggt  22860
gaacgcgacg ttcgagggct acaaggccct gaacgtccgc cggctgaaca tcatggccgg  22920
cgacgaaatt aactcgcgca acttcgacac cctggtcgag ctgattgcgc cgaccaagga  22980
tgacgtggtg atcgacaacg gtgccagctc gttcgtgcct ctgtcgcatt acctcatcag  23040
caaccaggtg ccggctctgc tgcaagaaat ggggcatgag ctggtcatcc ataccgtcgt  23100
caccggcggc caggctctcc tggacacggt gagcggcttc gcccagctcg ccagccagtt  23160
cccggccgaa gcgcttttcg tggtctggct gaacccgtat tgggggccta tcgagcatga  23220
gggcaagagc tttgagcaga tgaaggcgta cacggccaac aaggcccgcg tgtcgtccat  23280
catccagatt ccggccctca aggaagaaac ctacggccgc gatttcagcg acatgctgca  23340
agagcggctg acgttcgacc aggcgctggc cgatgaatcg ctcacgatca tgacgcggca  23400
acgcctcaag atcgtgcggc gcggcctgtt tgaacagctc gacgcggcgg ccgtgctatg  23460
```

agcgaccaga ttgaagagct gatccgggag attgcggcca agcacggcat cgccgtcggc 23520
cgcgacgacc cggtgctgat cctgcatacc atcaacgccc ggctcatggc cgacagtgcg 23580
gccaagcaag aggaaatcct tgccgcgttc aaggaagagc tggaagggat cgcccatcgt 23640
tggggcgagg acgccaaggc caaagcggag cggatgctga acgcggccct ggcggccagc 23700
aaggacgcaa tggcgaaggt aatgaaggac agcgccgcgc aggcggccga agcgatccgc 23760
agggaaatcg acgacggcct tggccgccag ctcgcggcca aggtcgcgga cgcgcggcgc 23820
gtggcgatga tgaacatgat cgccggcggc atggtgttgt tcgcggccgc cctggtggtg 23880
tgggcctcgt tatgaatcgc agaggcgcag atgaaaaagc ccggcgttgc cgggctttgt 23940
ttttgcgtta gctgggcttg tttgacaggc ccaagctctg actgcgcccg cgctcgcgct 24000
cctgggcctg tttcttctcc tgctcctgct tgcgcatcag ggcctggtgc cgtcgggctg 24060
cttcacgcat cgaatcccag tcgccggcca gctcgggatg ctccgcgcgc atcttgcgcg 24120
tcgccagttc ctcgatcttg ggcgcgtgaa tgcccatgcc ttccttgatt tcgcgcacca 24180
tgtccagccg cgtgtgcagg gtctgcaagc gggcttgctg ttgggcctgc tgctgctgcc 24240
aggcggcctt tgtacgcggc agggacagca agccgggggc attggactgt agctgctgca 24300
aacgcgcctg ctgacggtct acgagctgtt ctaggcggtc ctcgatgcgc tccacctggt 24360
catgctttgc ctgcacgtag agcgcaaggg tctgctggta ggtctgctcg atgggcgcgg 24420
attctaagag ggcctgctgt tccgtctcgg cctcctgggc cgcctgtagc aaatcctcgc 24480
cgctgttgcc gctggactgc tttactgccg gggactgctg ttgccctgct cgcgccgtcg 24540
tcgcagttcg gcttgccccc actcgattga ctgcttcatt tcgagccgca gcgatgcgat 24600
ctcggattgc gtcaacggac ggggcagcgc ggaggtgtcc ggcttctcct tgggtgagtc 24660
ggtcgatgcc atagccaaag gtttccttcc aaaatgcgtc cattgctgga ccgtgtttct 24720
cattgatgcc cgcaagcatc ttcggcttga ccgccaggtc aagcgcgcct tcatgggcgg 24780
tcatgacgga cgccgccatg accttgccgc cgttgttctc gatgtagccg cgtaatgagg 24840
caatggtgcc gcccatcgtc agcgtgtcat cgacaacgat gtacttctgg ccggggatca 24900
cctccccctc gaaagtcggg ttgaacgcca ggcgatgatc tgaaccggct ccggttcggg 24960
cgaccttctc ccgctgcaca atgtccgttt cgacctcaag gccaaggcgg tcggccagaa 25020
cgaccgccat catggccgga atcttgttgt tccccgccgc ctcgacggcg aggactggaa 25080
cgatgcgggg cttgtcgtcg ccgatcagcg tcttgagctg ggcaacagtg tcgtccgaaa 25140
tcaggcgctc gaccaaatta agcgccgctt ccgcgtcgcc ctgcttcgca gcctggtatt 25200
caggctcgtt ggtcaaagaa ccaaggtcgc cgttgcgaac caccttcggg aagtctcccc 25260
acggtgcgcg ctcggctctg ctgtagctgc tcaagacgcc tccctttta gccgctaaaa 25320
ctctaacgag tgcgcccgcg actcaacttg acgctttcgg cacttacctg tgccttgcca 25380
cttgcgtcat aggtgatgct tttcgcactc ccgatttcag gtactttatc gaaatctgac 25440
cgggcgtgca ttacaaagtt cttccccacc tgttggtaaa tgctgccgct atctgcgtgg 25500
acgatgctgc cgtcgtggcg ctgcgactta tcggcctttt gggccatata gatgttgtaa 25560
atgccaggtt tcagggcccc ggctttatct accttctggt tcgtccatgc gccttggttc 25620
tcggtctgga caattctttg cccattcatg accaggaggc ggtgtttcat tgggtgactc 25680
ctgacggttg cctctggtgt taaacgtgtc ctggtcgctt gccggctaaa aaaaagccga 25740
cctcggcagt tcgaggccgg ctttccctag agccgggcgc gtcaaggttg ttccatctat 25800
tttagtgaac tgcgttcgat ttatcagtta ctttcctccc gctttgtgtt tcctcccact 25860

```
cgtttccgcg tctagccgac ccctcaacat agcggcctct tcttgggctg cctttgcctc  25920
ttgccgcgct tcgtcacgct cggcttgcac cgtcgtaaag cgctcggcct gcctggccgc  25980
ctcttgcgcc gccaacttcc tttgctcctg gtgggcctcg gcgtcggcct gcgccttcgc  26040
tttcaccgct gccaactccg tgcgcaaact ctccgcttcg cgcctggtgg cgtcgcgctc  26100
gccgcgaagc gcctgcattt cctggttggc cgcgtccagg gtcttgcggc tctcttcttt  26160
gaatgcgcgg gcgtcctggt gagcgtagtc cagctcggcg cgcagctcct gcgctcgacg  26220
ctccacctcg tcggcccgct gcgtcgccag cgcggcccgc tgctcggctc ctgccagggc  26280
ggtgcgtgct tcggccaggg cttgccgctg gcgtgcggcc agctcggccg cctcggcggc  26340
ctgctgctct agcaatgtaa cgcgcgcctg ggcttcttcc agctcgcggg cctgcgcctc  26400
gaaggcgtcg gccagctccc cgcgcacggc ttccaactcg ttgcgctcac gatcccagcc  26460
ggcttgcgct gcctgcaacg attcattggc aagggcctgg gcggcttgcc agagggcggc  26520
cacggcctgg ttgccggcct gctgcaccgc gtccggcacc tggactgcca gcggggcggc  26580
ctgcgccgtg cgctggcgtc gccattcgcg catgccggcg ctggcgtcgt tcatgttgac  26640
gcgggcggcc ttacgcactg catccacggt cgggaagttc tcccggtcgc cttgctcgaa  26700
cagctcgtcc gcagccgcaa aaatgcggtc gcgcgtctct ttgttcagtt ccatgttggc  26760
tccggtaatt ggtaagaata ataatactct tacctacctt atcagcgcaa gagtttagct  26820
gaacagttct cgacttaacg gcaggttttt tagcggctga agggcaggca aaaaaagccc  26880
cgcacggtcg gcgggggcaa agggtcagcg ggaaggggat tagcgggcgt cgggcttctt  26940
catgcgtcgg ggccgcgctt cttgggatgg agcacgacga agcgcgcacg cgcatcgtcc  27000
tcggccctat cggcccgcgt cgcggtcagg aacttgtcgc gcgctaggtc ctccctggtg  27060
ggcaccaggg gcatgaactc ggcctgctcg atgtaggtcc actccatgac cgcatcgcag  27120
tcgaggccgc gttccttcac cgtctcttgc aggtcgcggt acgcccgctc gttgagcggc  27180
tggtaacggg ccaattggtc gtaaatggct gtcggccatg agcggccttt cctgttgagc  27240
cagcagccga cgacgaagcc ggcaatgcag gcccctggca caaccaggcc gacgccgggg  27300
gcaggggatg gcagcagctc gccaaccagg aaccccgccg cgatgatgcc gatgccggtc  27360
aaccagccct tgaaactatc cggccccgaa acacccctgc gcattgcctg gatgctgcgc  27420
cggatagctt gcaacatcag gagccgtttc ttttgttcgt cagtcatggt ccgccctcac  27480
cagttgttcg tatcggtgtc ggacgaactg aaatcgcaag agctgccggt atcggtccag  27540
ccgctgtccg tgtcgctgct gccgaagcac ggcgaggggt ccgcgaacgc cgcagacggc  27600
gtatccggcc gcagcgcatc gcccagcatg gccccggtca gcgagccgcc ggccaggtag  27660
cccagcatgg tgctgttggt cgccccggcc accagggccg acgtgacgaa atcgccgtca  27720
ttccctctgg attgttcgct gctcggcggg gcagtgcgcc gcgccggcgg cgtcgtggat  27780
ggctcgggtt ggctggcctg cgacggccgg cgaaaggtgc gcagcagctc gttatcgacc  27840
ggctgcggcg tcggggccgc cgccttgcgc tgcggtcggt gttccttctt cggctcgcgc  27900
agcttgaaca gcatgatcgc ggaaaccagc agcaacgccg cgcctacgcc tcccgcgatg  27960
tagaacagca tcggattcat tcttcggtcc tccttgtagc ggaaccgttg tctgtgcggc  28020
gcgggtggcc cgcgccgctg tctttgggga tcagccctcg atgagcgcga ccagtttcac  28080
gtcggcaagg ttcgcctcga actcctggcc gtcgtcctcg tacttcaacc aggcatagcc  28140
ttccgccggc ggccgacggt tgaggataag gcgggcaggg cgctcgtcgt gctcgacctg  28200
gacgatggcc tttttcagct tgtccgggtc cggctccttc gcgccctttt ccttggcgtc  28260
```

```
cttaccgtcc tggtcgccgt cctcgccgtc ctggccgtcg ccggcctccg cgtcacgctc  28320
ggcatcagtc tggccgttga aggcatcgac ggtgttggga tcgcggccct tctcgtccag  28380
gaactcgcgc agcagcttga ccgtgccgcg cgtgatttcc tgggtgtcgt cgtcaagcca  28440
cgcctcgact tcctccgggc gcttcttgaa ggccgtcacc agctcgttca ccacggtcac  28500
gtcgcgcacg cggccggtgt tgaacgcatc ggcgatcttc tccggcaggt ccagcagcgt  28560
gacgtgctgg gtgatgaacg ccggcgactt gccgatttcc ttggcgatat cgcctttctt  28620
cttgcccttc gccagctcgc ggccaatgaa gtcggcaatt tcgcgcgggg tcagctcgtt  28680
gcgttgcagg ttctcgataa cctggtcggc ttcgttgtag tcgttgtcga tgaacgccgg  28740
gatggacttc ttgccggccc acttcgagcc acggtagcgg cgggcgccgt gattgatgat  28800
atagcggccc ggctgctcct ggttctcgcg caccgaaatg ggtgacttca ccccgcgctc  28860
tttgatcgtg gcaccgattt ccgcgatgct ctccggggaa aagccggggt tgtcggccgt  28920
ccgcggctga tgcggatctt cgtcgatcag gtccaggtcc agctcgatag ggccggaacc  28980
gccctgagac gccgcaggag cgtccaggag gctcgacagg tcgccgatgc tatccaaccc  29040
caggccggac ggctgcgccg cgcctgcggc ttcctgagcg gccgcagcgg tgtttttctt  29100
ggtggtcttg gcttgagccg cagtcattgg gaaatctcca tcttcgtgaa cacgtaatca  29160
gccagggcgc gaacctcttt cgatgccttg cgcgcggccg ttttcttgat cttccagacc  29220
ggcacaccgg atgcgagggc atcggcgatg ctgctgcgca ggccaacggt ggccggaatc  29280
atcatcttgg ggtacgcggc cagcagctcg gcttggtggc gcgcgtggcg cggattccgc  29340
gcatcgacct tgctgggcac catgccaagg aattgcagct tggcgttctt ctggcgcacg  29400
ttcgcaatgg tcgtgaccat cttcttgatg ccctggatgc tgtacgcctc aagctcgatg  29460
ggggacagca catagtcggc cgcgaagagg gcggccgcca ggccgacgcc aagggtcggg  29520
gccgtgtcga tcaggcacac gtcgaagcct tggttcgcca gggccttgat gttcgccccg  29580
aacagctcgc gggcgtcgtc cagcgacagc cgttcggcgt tcgccagtac cgggttggac  29640
tcgatgaggg cgaggcgcgc ggcctggccg tcgccggctg cgggtgcggt ttcggtccag  29700
ccgccggcag ggacagcgcc gaacagcttg cttgcatgca ggccggtagc aaagtccttg  29760
agcgtgtagg acgcattgcc ctgggggtcc aggtcgatca cggcaacccg caagccgcgc  29820
tcgaaaaagt cgaaggcaag atgcacaagg gtcgaagtct tgccgacgcc gcctttctgg  29880
ttggccgtga ccaaagtttt catcgtttgg tttcctgttt tttcttggcg tccgcttccc  29940
acttccggac gatgtacgcc tgatgttccg gcagaaccgc cgttacccgc gcgtacccct  30000
cgggcaagtt cttgtcctcg aacgcggccc acacgcgatg caccgcttgc gacactgcgc  30060
ccctggtcag tcccagcgac gttgcgaacg tcgcctgtgg cttcccatcg actaagacgc  30120
cccgcgctat ctcgatggtc tgctgcccca cttccagccc ctggatcgcc tcctggaact  30180
ggctttcggt aagccgtttc ttcatggata acacccataa tttgctccgc gccttggttg  30240
aacatagcgg tgacagccgc cagcacatga gagaagttta gctaaacatt tctcgcacgt  30300
caacaccttt agccgctaaa actcgtcctt ggcgtaacaa aacaaaagcc cggaaaccgg  30360
gctttcgtct cttgccgctt atggctctgc acccggctcc atcaccaaca ggtcgcgcac  30420
gcgcttcact cggttgcgga tcgacactgc cagcccaaca aagccggttg ccgccgccgc  30480
caggatcgcg ccgatgatgc cggccacacc ggccatcgcc caccaggtcg ccgccttccg  30540
gttccattcc tgctggtact gcttcgcaat gctggacctc ggctcaccat aggctgaccg  30600
ctcgatggcg tatgccgctt ctccccttgg cgtaaaaccc agcgccgcag gcggcattgc  30660
```

```
catgctgccc gccgctttcc cgaccacgac gcgcgcacca ggcttgcggt ccagaccttc  30720
ggccacggcg agctgcgcaa ggacataatc agccgccgac ttggctccac gcgcctcgat  30780
cagctcttgc actcgcgcga aatccttggc ctccacggcc gccatgaatc gcgcacgcgg  30840
cgaaggctcc gcagggccgg cgtcgtgatc gccgccgaga atgcccttca ccaagttcga  30900
cgacacgaaa atcatgctga cggctatcac catcatgcag acggatcgca cgaacccgct  30960
gaattgaaca cgagcacggc acccgcgacc actatgccaa gaatgcccaa ggtaaaaatt  31020
gccggccccg ccatgaagtc cgtgaatgcc ccgacggccg aagtgaaggg caggccgcca  31080
cccaggccgc cgccctcact gcccggcacc tggtcgctga atgtcgatgc cagcacctgc  31140
ggcacgtcaa tgcttccggg cgtcgcgctc gggctgatcg cccatcccgt tactgccccg  31200
atcccggcaa tggcaaggac tgccagcgct gccatttttg gggtgaggcc gttcgcggcc  31260
gaggggcgca gcccctgggg ggatgggagg cccgcgttag cgggccggga gggttcgaga  31320
agggggggca ccccccttcg gcgtgcgcgg tcacgcgcac agggcgcagc cctggttaaa  31380
aacaaggttt ataaatattg gtttaaaagc aggttaaaag acaggttagc ggtggccgaa  31440
aaacgggcgg aaacccttgc aaatgctgga ttttctgcct gtggacagcc cctcaaatgt  31500
caataggtgc gcccctcatc tgtcagcact ctgcccctca agtgtcaagg atcgcgcccc  31560
tcatctgtca gtagtcgcgc ccctcaagtg tcaataccgc agggcactta tccccaggct  31620
tgtccacatc atctgtggga aactcgcgta aaatcaggcg ttttcgccga tttgcgaggc  31680
tggccagctc cacgtcgccg gccgaaatcg agcctgcccc tcatctgtca acgccgcgcc  31740
gggtgagtcg gcccctcaag tgtcaacgtc cgcccctcat ctgtcagtga gggccaagtt  31800
ttccgcgagg tatccacaac gccggcggcc gcggtgtctc gcacacggct tcgacggcgt  31860
ttctggcgcg tttgcagggc catagacggc cgccagccca gcggcgaggg caaccagccc  31920
ggtgagcgtc ggaaaggcgc tggaagcccc gtagcgacgc ggagaggggc gagacaagcc  31980
aagggcgcag gctcgatgcg cagcacgaca tagccggttc tcgcaaggac gagaatttcc  32040
ctgcggtgcc cctcaagtgt caatgaaagt ttccaacgcg agccattcgc gagagccttg  32100
agtccacgct agatgagagc tttgttgtag gtggaccagt tggtgatttt gaacttttgc  32160
tttgccacgg aacggtctgc gttgtcggga agatgcgtga tctgatcctt caactcagca  32220
aaagttcgat ttattcaaca aagccacgtt gtgtctcaaa atctctgatg ttacattgca  32280
caagataaaa atatatcatc atgaacaata aaactgtctg cttacataaa cagtaataca  32340
aggggtgtta tgagccatat tcaacgggaa acgtcttgct cgactctaga gctcgttcct  32400
cgaggcctcg aggcctcgag gaacggtacc tgcggggaag cttacaataa tgtgtgttgt  32460
taagtcttgt tgcctgtcat cgtctgactg actttcgtca taaatcccgg cctccgtaac  32520
ccagctttgg gcaagctcac ggatttgatc cggcggaacg ggaatatcga gatgccgggc  32580
tgaacgctgc agttccagct ttccctttcg ggacaggtac tccagctgat tgattatctg  32640
ctgaagggtc ttggttccac ctcctggcac aatgcgaatg attacttgag cgcgatcggg  32700
catccaattt tctcccgtca ggtgcgtggt caagtgctac aaggcacctt tcagtaacga  32760
gcgaccgtcg atccgtcgcc gggatacgga caaaatggag cgcagtagtc catcgagggc  32820
ggcgaaagcc tcgccaaaag caatacgttc atctcgcaca gcctccagat ccgatcgagg  32880
gtcttcggcg taggcagata gaagcatgga tacattgctt gagagtattc cgatggactg  32940
aagtatggct tccatctttt ctcgtgtgtc tgcatctatt tcgagaaagc ccccgatgcg  33000
gcgcaccgca acgcgaattg ccatactatc cgaaagtccc agcaggcgcg cttgatagga  33060
```

```
aaaggtttca tactcggccg atcgcagacg ggcactcacg accttgaacc cttcaacttt  33120
cagggatcga tgctggttga tggtagtctc actcgacgtg gctctggtgt gttttgacat  33180
agcttcctcc aaagaaagcg gaaggtctgg atactccagc acgaaatgtg cccgggtaga  33240
cggatggaag tctagccctg ctcaatatga aatcaacagt acatttacag tcaatactga  33300
atatacttgc tacatttgca attgtcttat aacgaatgtg aaataaaaat agtgtaacaa  33360
cgcttttact catcgataat cacaaaaaca tttatacgaa caaaaataca aatgcactcc  33420
ggtttcacag gataggcggg atcagaatat gcaacttttg acgttttgtt ctttcaaagg  33480
gggtgctggc aaaaccaccg cactcatggg cctttgcgct gctttggcaa atgacggtaa  33540
acgagtggcc ctctttgatg ccgacgaaaa ccggcctctg acgcgatgga gagaaaacgc  33600
cttacaaagc agtactggga tcctcgctgt gaagtctatt ccgccgacga aatgcccctt  33660
cttgaagcag cctatgaaaa tgccgagctc gaaggatttg attatgcgtt ggccgatacg  33720
cgtggcggct cgagcgagct caacaacaca atcatcgcta gctcaaacct gcttctgatc  33780
cccaccatgc taacgccgct cgacatcgat gaggcactat ctacctaccg ctacgtcatc  33840
gagctgctgt tgagtgaaaa tttggcaatt cctacagctg ttttgcgcca acgcgtcccg  33900
gtcggccgat tgacaacatc gcaacgcagg atgtcagaga cgctagagag ccttccagtt  33960
gtaccgtctc ccatgcatga aagagatgca tttgccgcga tgaaagaacg cggcatgttg  34020
catcttacat tactaaacac gggaactgat ccgacgatgc gcctcataga gaggaatctt  34080
cggattgcga tggaggaagt cgtggtcatt tcgaaactga tcagcaaaat cttggaggct  34140
tgaagatggc aattcgcaag cccgcattgt cggtcggcga agcacggcgg cttgctggtg  34200
ctcgacccga gatccaccat cccaacccga cacttgttcc ccagaagctg gacctccagc  34260
acttgcctga aaaagccgac gagaaagacc agcaacgtga gcctctcgtc gccgatcaca  34320
tttacagtcc cgatcgacaa cttaagctaa ctgtggatgc ccttagtcca cctccgtccc  34380
cgaaaaagct ccaggttttt ctttcagcgc gaccgcccgc gcctcaagtg tcgaaaacat  34440
atgacaacct cgttcggcaa tacagtccct cgaagtcgct acaaatgatt ttaaggcgcg  34500
cgttggacga tttcgaaagc atgctggcag atggatcatt tcgcgtggcc ccgaaaagtt  34560
atccgatccc ttcaactaca gaaaaatccg ttctcgttca gacctcacgc atgttcccgg  34620
ttgcgttgct cgaggtcgct cgaagtcatt ttgatccgtt ggggttggag accgctcgag  34680
ctttcggcca caagctggct accgccgcgc tcgcgtcatt ctttgctgga gagaagccat  34740
cgagcaattg gtgaagaggg acctatcgga acccctcacc aaatattgag tgtaggtttg  34800
aggccgctgg ccgcgtcctc agtcaccttt tgagccagat aattaagagc caaatgcaat  34860
tggctcaggc tgccatcgtc cccccgtgcg aaacctgcac gtccgcgtca aagaaataac  34920
cggcacctct tgctgttttt atcagttgag ggcttgacgg atccgcctca agtttgcggc  34980
gcagccgcaa aatgagaaca tctatactcc tgtcgtaaac ctcctcgtcg cgtactcgac  35040
tggcaatgag aagttgctcg cgcgatagaa cgtcgcgggg tttctctaaa aacgcgagga  35100
gaagattgaa ctcacctgcc gtaagtttca cctcaccgcc agcttcggac atcaagcgac  35160
gttgcctgag attaagtgtc cagtcagtaa aacaaaaaga ccgtcggtct ttggagcgga  35220
caacgttggg gcgcacgcgc aaggcaaccc gaatgcgtgc aagaaactct ctcgtactaa  35280
acggcttagc gataaaatca cttgctccta gctcgagtgc aacaacttta tccgtctcct  35340
caaggcggtc gccactgata attatgattg gaatatcaga ctttgccgcc agatttcgaa  35400
cgatctcaag cccatcttca cgacctaaat ttagatcaac aaccacgaca tcgaccgtcg  35460
```

```
cggaagagag tactctagtg aactgggtgc tgtcggctac cgcggtcact ttgaaggcgt  35520
ggatcgtaag gtattcgata ataagatgcc gcatagcgac atcgtcatcg ataagaagaa  35580
cgtgtttcaa cggctcacct ttcaatctaa aatctgaacc cttgttcaca gcgcttgaga  35640
aattttcacg tgaaggatgt acaatcatct ccagctaaat gggcagttcg tcagaattgc  35700
ggctgaccgc ggatgacgaa aatgcgaacc aagtatttca attttatgac aaaagttctc  35760
aatcgttgtt acaagtgaaa cgcttcgagg ttacagctac tattgattaa ggagatcgcc  35820
tatggtctcg ccccggcgtc gtgcgtccgc cgcgagccag atctcgccta cttcataaac  35880
gtcctcatag gcacggaatg gaatgatgac atcgatcgcc gtagagagca tgtcaatcag  35940
tgtgcgatct tccaagctag caccttgggc gctacttttg acaagggaaa acagtttctt  36000
gaatccttgg attggattcg cgccgtgtat tgttgaaatc gatcccggat gtcccgagac  36060
gacttcactc agataagccc atgctgcatc gtcgcgcatc tcgccaagca atatccggtc  36120
cggccgcata cgcagacttg cttggagcaa gtgctcggcg ctcacagcac ccagcccagc  36180
accgttcttg gagtagagta gtctaacatg attatcgtgt ggaatgacga gttcgagcgt  36240
atcttctatg gtgattagcc tttcctgggg ggggatggcg ctgatcaagg tcttgctcat  36300
tgttgtcttg ccgcttccgg tagggccaca tagcaacatc gtcagtcggc tgacgacgca  36360
tgcgtgcaga aacgcttcca aatccccgtt gtcaaaatgc tgaaggatag cttcatcatc  36420
ctgattttgg cgtttccttc gtgtctgcca ctggttccac ctcgaagcat cataacggga  36480
ggagacttct ttaagaccag aaacacgcga gcttggccgt cgaatggtca agctgacggt  36540
gcccgaggga acggtcggcg gcagacagat ttgtagtcgt tcaccaccag gaagttcagt  36600
ggcgcagagg gggttacgtg gtccgacatc ctgctttctc agcgcgcccg ctaaaatagc  36660
gatatcttca agatcatcat aagagacggg caaaggcatc ttggtaaaaa tgccggcttg  36720
gcgcacaaat gcctctccag gtcgattgat cgcaatttct tcagtcttcg ggtcatcgag  36780
ccattccaaa atcggcttca gaagaaagcg tagttgcgga tccacttcca tttacaatgt  36840
atcctatctc taagcggaaa tttgaattca ttaagagcgg cggttcctcc cccgcgtggc  36900
gccgccagtc aggcggagct ggtaaacacc aaagaaatcg aggtcccgtg ctacgaaaat  36960
ggaaacggtg tcaccctgat tcttcttcag ggttggcggt atgttgatgg ttgccttaag  37020
ggctgtctca gttgtctgct caccgttatt ttgaaagctg ttgaagctca tcccgccacc  37080
cgagctgccg gcgtaggtgc tagctgcctg gaaggcgcct tgaacaacac tcaagagcat  37140
agctccgcta aaacgctgcc agaagtggct gtcgaccgag cccggcaatc ctgagcgacc  37200
gagttcgtcc gcgcttggcg atgttaacga gatcatcgca tggtcaggtg tctcggcgcg  37260
atcccacaac acaaaaacgc gcccatctcc ctgttgcaag ccacgctgta tttcgccaac  37320
aacggtggtg ccacgatcaa gaagcacgat attgttcgtt gttccacgaa tatcctgagg  37380
caagacacac tttacatagc ctgccaaatt tgtgtcgatt gcggtttgca agatgcacgg  37440
aattattgtc ccttgcgtta ccataaaatc ggggtgcggc aagagcgtgg cgctgctggg  37500
ctgcagctcg gtgggtttca tacgtatcga caaatcgttc tcgccggaca cttcgccatt  37560
cggcaaggag ttgtcgtcac gcttgccttc ttgtcttcgg cccgtgtcgc cctgaatggc  37620
gcgtttgctg accccttgat cgccgctgct atatgcaaaa atcggtgttt cttccggccg  37680
tggctcatgc cgctccggtt cgcccctcgg cggtagagga gcagcaggct gaacagcctc  37740
ttgaaccgct ggaggatccg gcggcacctc aatcggagct ggatgaaatg gcttggtgtt  37800
tgttgcgatc aaagttgacg gcgatgcgtt ctcattcacc ttcttttggc gcccacctag  37860
```

```
ccaaatgagg cttaatgata acgcgagaac gacacctccg acgatcaatt tctgagaccc  37920
cgaaagacgc cggcgatgtt tgtcggagac cagggatcca gatgcatcaa cctcatgtgc  37980
cgcttgctga ctatcgttat tcatcccttc gccccccttca ggacgcgttt cacatcgggc  38040
ctcaccgtgc ccgtttgcgg cctttggcca acgggatcgt aagcggtgtt ccagatacat  38100
agtactgtgt ggccatccct cagacgccaa cctcgggaaa ccgaagaaat ctcgacatcg  38160
ctccctttaa ctgaatagtt ggcaacagct tccttgccat caggattgat ggtgtagatg  38220
gagggtatgc gtacattgcc cggaaagtgg aataccgtcg taaatccatt gtcgaagact  38280
tcgagtggca acagcgaacg atcgccttgg gcgacgtagt gccaattact gtccgccgca  38340
ccaagggctg tgacaggctg atccaataaa ttctcagctt tccgttgata ttgtgcttcc  38400
gcgtgtagtc tgtccacaac agccttctgt tgtgcctccc ttcgccgagc cgccgcatcg  38460
tcggcggggt aggcgaattg gacgctgtaa tagagatcgg gctgctcttt atcgaggtgg  38520
gacagagtct tggaacttat actgaaaaca taacggcgca tcccggagtc gcttgcggtt  38580
agcacgatta ctggctgagg cgtgaggacc tggcttgcct tgaaaaatag ataatttccc  38640
cgcggtaggg ctgctagatc tttgctattt gaaacggcaa ccgctgtcac cgtttcgttc  38700
gtggcgaatg ttacgaccaa agtagctcca accgccgtcg agaggcgcac cacttgatcg  38760
ggattgtaag ccaaataacg catgcgcgga tctagcttgc ccgccattgg agtgtcttca  38820
gcctccgcac cagtcgcagc ggcaaataaa catgctaaaa tgaaaagtgc ttttctgatc  38880
atggttcgct gtggcctacg tttgaaacgg tatcttccga tgtctgatag gaggtgacaa  38940
ccagacctgc cgggttggtt agtctcaatc tgccgggcaa gctggtcacc ttttcgtagc  39000
gaactgtcgc ggtccacgta ctcaccacag gcattttgcc gtcaacgacg agggtccttt  39060
tatagcgaat ttgctgcgtg cttggagtta catcatttga agcgatgtgc tcgacctcca  39120
ccctgccgcg tttgccaaga atgacttgag gcgaactggg attgggatag ttgaagaatt  39180
gctggtaatc ctggcgcact gttggggcac tgaagttcga taccaggtcg taggcgtact  39240
gagcggtgtc ggcatcataa ctctcgcgca ggcgaacgta ctcccacaat gaggcgttaa  39300
cgacggcctc ctcttgagtt gcaggcaatc gcgagacaga cacctcgctg tcaacggtgc  39360
cgtccggccg tatccataga tatacgggca caagcctgct caacggcacc attgtggcta  39420
tagcgaacgc ttgagcaaca tttcccaaaa tcgcgatagc tgcgacagct gcaatgagtt  39480
tggagagacg tcgcgccgat ttcgctcgcg cggtttgaaa ggcttctact tccttatagt  39540
gctcggcaag gctttcgcgc gccactagca tggcatattc aggccccgtc atagcgtcca  39600
cccgaattgc cgagctgaag atctgacgga gtaggctgcc atcgccccac attcagcggg  39660
aagatcgggc ctttgcagct cgctaatgtg tcgtttgtct ggcagccgct caaagcgaca  39720
actaggcaca gcaggcaata cttcatagaa ttctccattg aggcgaattt ttgcgcgacc  39780
tagcctcgct caacctgagc gaagcgacgg tacaagctgc tggcagattg ggttgcgccg  39840
ctccagtaac tgcctccaat gttgccggcg atcgccggca aagcgacaat gagcgcatcc  39900
cctgtcagaa aaaacatatc gagttcgtaa agaccaatga tcttggccgc ggtcgtaccg  39960
gcgaaggtga ttacaccaag cataagggtg agcgcagtcg cttcggttag gatgacgatc  40020
gttgccacga ggtttaagag gagaagcaag agaccgtagg tgataagttg cccgatccac  40080
ttagctgcga tgtcccgcgt gcgatcaaaa atatatccga cgaggatcag aggcccgatc  40140
gcgagaagca ctttcgtgag aattccaacg gcgtcgtaaa ctccgaaggc agaccagagc  40200
gtgccgtaaa ggacccactg tgccccttgg aaagcaagga tgtcctggtc gttcatcgga  40260
```

```
ccgatttcgg atgcgatttt ctgaaaaacg gcctgggtca cggcgaacat tgtatccaac  40320
tgtgccggaa cagtctgcag aggcaagccg gttacactaa actgctgaac aaagtttggg  40380
accgtctttt cgaagatgga aaccacatag tcttggtagt tagcctgccc aacaattaga  40440
gcaacaacga tggtgaccgt gatcacccga gtgataccgc tacgggtatc gacttcgccg  40500
cgtatgacta aaataccctg aacaataatc caaagagtga cacaggcgat caatggcgca  40560
ctcaccgcct cctggatagt ctcaagcatc gagtccaagc ctgtcgtgaa ggctacatcg  40620
aagatcgtat gaatggccgt aaacggcgcc ggaatcgtga aattcatcga ttggacctga  40680
acttgactgg tttgtcgcat aatgttggat aaaatgagct cgcattcggc gaggatgcgg  40740
gcggatgaac aaatcgccca gccttagggg agggcaccaa agatgacagc ggtcttttga  40800
tgctccttgc gttgagcggc cgcctcttcc gcctcgtgaa ggccggcctg cgcggtagtc  40860
atcgttaata ggcttgtcgc ctgtacattt tgaatcattg cgtcatggat ctgcttgaga  40920
agcaaaccat tggtcacggt tgcctgcatg atattgcgag atcgggaaag ctgagcagac  40980
gtatcagcat tcgccgtcaa gcgtttgtcc atcgtttcca gattgtcagc cgcaatgcca  41040
gcgctgtttg cggaaccggt gatctgcgat cgcaacaggt ccgcttcagc atcactaccc  41100
acgactgcac gatctgtatc gctggtgatc gcacgtgccg tggtcgacat tggcattcgc  41160
ggcgaaaaca tttcattgtc taggtccttc gtcgaaggat actgattttt ctggttgagc  41220
gaagtcagta gtccagtaac gccgtaggcc gacgtcaaca tcgtaaccat cgctatagtc  41280
tgagtgagat tctccgcagt cgcgagcgca gtcgcgagcg tctcagcctc cgttgccggg  41340
tcgctaacaa caaactgcgc ccgcgcgggc tgaatatata gaaagctgca ggtcaaaact  41400
gttgcaataa gttgcgtcgt cttcatcgtt tcctacctta tcaatcttct gcctcgtggt  41460
gacgggccat gaattcgctg agccagccag atgagttgcc ttcttgtgcc tcgcgtagtc  41520
gagttgcaaa gcgcaccgtg ttggcacgcc ccgaaagcac ggcgacatat tcacgcatat  41580
cccgcagatc aaattcgcag atgacgcttc cactttctcg tttaagaaga aacttacggc  41640
tgccgaccgt catgtcttca cggatcgcct gaaattcctt ttcggtacat ttcagtccat  41700
cgacataagc cgatcgatct gcggttggtg atggatagaa aatcttcgtc atacattgcg  41760
caaccaagct ggctcctagc ggcgattcca gaacatgctc tggttgctgc gttgccagta  41820
ttagcatccc gttgtttttt cgaacggtca ggaggaattt gtcgacgaca gtcgaaaatt  41880
tagggtttaa caaataggcg cgaaactcat cgcagctcat cacaaaacgg cggccgtcga  41940
tcatggctcc aatccgatgc aggagatatg ctgcagcggg agcgcatact tcctcgtatt  42000
cgagaagatg cgtcatgtcg aagccggtaa tcgacggatc taactttact tcgtcaactt  42060
cgccgtcaaa tgcccagcca agcgcatggc cccggcacca gcgttggagc cgcgctcctg  42120
cgccttcggc gggcccatgc aacaaaaatt cacgtaaccc cgcgattgaa cgcatttgtg  42180
gatcaaacga gagctgacga tggataccac ggaccagacg gcggttctct tccggagaaa  42240
tcccaccccg accatcactc tcgatgagag ccacgatcca ttcgcgcaga aaatcgtgtg  42300
aggctgctgt gttttctagg ccacgcaacg gcgccaaccc gctgggtgtg cctctgtgaa  42360
gtgccaaata tgttcctcct gtggcgcgaa ccagcaattc gccaccccgg tccttgtcaa  42420
agaacacgac cgtacctgca cggtcgacca tgctctgttc gagcatggct agaacaaaca  42480
tcatgagcgt cgtcttaccc ctcccgatag gcccgaatat tgccgtcatg ccaacatcgt  42540
gctcatgcgg gatatagtcg aaaggcgttc cgccattggt acgaaatcgg gcaatcgcgt  42600
tgccccagtg gcctgagctg gcgccctctg gaaagttttc gaaagagaca aaccctgcga  42660
```

```
aattgcgtga agtgattgcg ccagggcgtg tgcgccactt aaaattcccc ggcaattggg  42720
accaataggc cgcttccata ccaataccttt cttggacaac cacggcacct gcatccgcca  42780
ttcgtgtccg agcccgcgcg cccctgtccc caagactatt gagatcgtct gcatagacgc  42840
aaaggctcaa atgatgtgag cccataacga attcgttgct cgcaagtgcg tcctcagcct  42900
cggataattt gccgatttga gtcacggctt tatcgccgga actcagcatc tggctcgatt  42960
tgaggctaag tttcgcgtgc gcttgcgggc gagtcaggaa cgaaaaactc tgcgtgagaa  43020
caagtggaaa atcgagggat agcagcgcgt tgagcatgcc cggccgtgtt tttgcagggt  43080
attcgcgaaa cgaatagatg gatccaacgt aactgtcttt tggcgttctg atctcgagtc  43140
ctcgcttgcc gcaaatgact ctgtcggtat aaatcgaagc gccgagtgag ccgctgacga  43200
ccggaaccgg tgtgaaccga ccagtcatga tcaaccgtag cgcttcgcca atttcggtga  43260
agagcacacc ctgcttctcg cggatgccaa gacgatgcag gccatacgct ttaagagagc  43320
cagcgacaac atgccaaaga tcttccatgt tcctgatctg gcccgtgaga tcgttttccc  43380
tttttccgct tagcttggtg aacctcctct ttaccttccc taaagccgcc tgtgggtaga  43440
caatcaacgt aaggaagtgt tcattgcgga ggagttggcc ggagagcacg cgctgttcaa  43500
aagcttcgtt caggctagcg gcgaaaacac tacggaagtg tcgcggcgcc gatgatggca  43560
cgtcggcatg acgtacgagg tgagcatata ttgacacatg atcatcagcg atattgcgca  43620
acagcgtgtt gaacgcacga caacgcgcat tgcgcatttc agtttcctca agctcgaatg  43680
caacgccatc aattctcgca atggtcatga tcgatccgtc ttcaagaagg acgatatggt  43740
cgctgaggtg gccaatataa gggagataga tctcaccgga tctttcggtc gttccactcg  43800
cgccgagcat cacaccattc ctctccctcg tgggggaacc ctaattggat ttgggctaac  43860
agtagcgccc ccccaaactg cactatcaat gcttcttccc gcggtccgca aaaatagcag  43920
gacgacgctc gccgcattgt agtctcgctc cacgatgagc cgggctgcaa accataacgg  43980
cacgagaacg acttcgtaga gcgggttctg aacgataacg atgacaaagc cggcgaacat  44040
catgaataac cctgccaatg tcagtggcac cccaagaaac aatgcgggcc gtgtggctgc  44100
gaggtaaagg gtcgattctt ccaaacgatc agccatcaac taccgccagt gagcgtttgg  44160
ccgaggaagc tcgccccaaa catgataaca atgccgccga cgacgccggc aaccagccca  44220
agcgaagccc gcccgaacat ccaggagatc ccgatagcga caatgccgag aacagcgagt  44280
gactggccga acggaccaag gataaacgtg catatattgt taaccattgt ggcggggtca  44340
gtgccgccac ccgcagattg cgctgcggcg ggtccggatg aggaaatgct ccatgcaatt  44400
gcaccgcaca agcttggggc gcagctcgat atcacgcgca tcatcgcatt cgagagcgag  44460
aggcgattta gatgtaaacg gtatctctca aagcatcgca tcaatgcgca cctccttagt  44520
ataagtcgaa taagacttga ttgtcgtctg cggatttgcc gttgtcctgg tgtggcggtg  44580
gcggagcgat taaaccgcca gcgccatcct cctgcgagcg gcgctgatat gacccccaaa  44640
catcccacgt ctcttcggat tttagcgcct cgtgatcgtc ttttggaggc tcgattaacg  44700
cgggcaccag cgattgagca gctgtttcaa cttttcgcac gtagccgttt gcaaaaccgc  44760
cgatgaaatt accggtgttg taagcggaga tcgcccgacg aagcgcaaat tgcttctcgt  44820
caatcgtttc gccgcctgca taacgacttt tcagcatgtt tgcagcggca gataatgatg  44880
tgcacgcctg gagcgcaccg tcaggtgtca gaccgagcat agaaaaattt cgagagttta  44940
tttgcatgag gccaacatcc agcgaatgcc gtgcatcgag acggtgcctg acgacttggg  45000
ttgcttggct gtgatcttgc cagtgaagcg tttcgccggt cgtgttgtca tgaatcgcta  45060
```

```
aaggatcaaa gcgactctcc accttagcta tcgccgcaag cgtagatgtc gcaactgatg  45120
gggcacactt gcgagcaaca tggtcaaact cagcagatga gagtggcgtg gcaaggctcg  45180
acgaacagaa ggagaccatc aaggcaagag aaagcgaccc cgatctctta agcatacctt  45240
atctccttag ctcgcaacta acaccgcctc tcccgttgga agaagtgcgt tgttttatgt  45300
tgaagattat cgggagggtc ggttactcga aaattttcaa ttgcttcttt atgatttcaa  45360
ttgaagcgag aaacctcgcc cggcgtcttg gaacgcaaca tggaccgaga accgcgcatc  45420
catgactaag caaccggatc gacctattca ggccgcagtt ggtcaggtca ggctcagaac  45480
gaaaatgctc ggcgaggtta cgctgtctgt aaacccattc gatgaacggg aagcttcctt  45540
ccgattgctc ttggcaggaa tattggccca tgcctgcttg cgctttgcaa atgctcttat  45600
cgcgttggta tcatatgcct tgtccgccag cagaaacgca ctctaagcga ttatttgtaa  45660
aaatgtttcg gtcatgcggc ggtcatgggc ttgacccgct gtcagcgcaa gacggatcgg  45720
tcaaccgtcg gcatcgacaa cagcgtgaat cttggtggtc aaaccgccac gggaacgtcc  45780
catacagcca tcgtcttgat cccgctgttt cccgtcgccg catgttggtg gacgcggaca  45840
caggaactgt caatcatgac gacattctat cgaaagcctt ggaaatcaca ctcagaatat  45900
gatcccagac gtctgcctca cgccatcgta caaagcgatt gtagcaggtt gtacaggaac  45960
cgtatcgatc aggaacgtct gcccagggcg ggcccgtccg gaagcgccac aagatgacat  46020
tgatcacccg cgtcaacgcg cggcacgcga cgcggcttat ttgggaacaa aggactgaac  46080
aacagtccat tcgaaatcgg tgacatcaaa gcggggacgg gttatcagtg gcctccaagt  46140
caagcctcaa tgaatcaaaa tcagaccgat ttgcaaacct gatttatgag tgtgcggcct  46200
aaatgatgaa atcgtccttc tagatcgcct ccgtggtgta gcaacacctc gcagtatcgc  46260
cgtgctgacc ttggccaggg aattgactgg caagggtgct ttcacatgac cgctcttttg  46320
gccgcgatag atgatttcgt tgctgctttg ggcacgtaga aggagagaag tcatatcgga  46380
gaaattcctc ctggcgcgag agcctgctct atcgcgacgg catcccactg tcgggaacag  46440
accggatcat tcacgaggcg aaagtcgtca acacatgcgt tataggcatc ttcccttgaa  46500
ggatgatctt gttgctgcca atctggaggt gcggcagccg caggcagatg cgatctcagc  46560
gcaacttgcg gcaaaacatc tcactcacct gaaaaccact agcgagtctc gcgatcagac  46620
gaaggccttt tacttaacga cacaatatcc gatgtctgca tcacaggcgt cgctatccca  46680
gtcaatacta aagcggtgca ggaactaaag attactgatg acttaggcgt gccacgaggc  46740
ctgagacgac gcgcgtagac agtttttga aatcattatc aaagtgatgg cctccgctga  46800
agcctatcac ctctgcgccg gtctgtcgga gagatgggca agcattatta cggtcttcgc  46860
gcccgtacat gcattggacg attgcagggt caatggatct gagatcatcc agaggattgc  46920
cgcccttacc ttccgtttcg agttggagcc agcccctaaa tgagacgaca tagtcgactt  46980
gatgtgacaa tgccaagaga gagatttgct taacccgatt tttttgctca agcgtaagcc  47040
tattgaagct tgccggcatg acgtccgcgc cgaaagaata tcctacaagt aaaacattct  47100
gcacaccgaa atgcttggtg tagacatcga ttatgtgacc aagatcctta gcagtttcgc  47160
ttggggaccg ctccgaccag aaataccgaa gtgaactgac gccaatgaca ggaatccctt  47220
ccgtctgcag ataggtacca tcgatagatc tgctgcctcg cgcgtttcgg tgatgacggt  47280
gaaaacctct gacacatgca gctcccggag acggtcacag cttgtctgta agcggatgcc  47340
gggagcagac aagcccgtca gggcgcgtca gcgggtgttg gcgggtgtcg gggcgcagcc  47400
atgacccagt cacgtagcga tagcggagtg tatactggct taactatgcg gcatcagagc  47460
```

```
agattgtact gagagtgcac catatgcggt gtgaaatacc gcacagatgc gtaaggagaa  47520
aataccgcat caggcgctct tccgcttcct cgctcactga ctcgctgcgc tcggtcgttc  47580
ggctgcggcg agcggtatca gctcactcaa aggcggtaat acggttatcc acagaatcag  47640
gggataacgc aggaaagaac atgtgagcaa aaggccagca aaaggccagg aaccgtaaaa  47700
aggccgcgtt gctggcgttt ttccataggc tccgcccccc tgacgagcat cacaaaaatc  47760
gacgctcaag tcagaggtgg cgaaacccga caggactata aagataccag gcgtttcccc  47820
ctggaagctc cctcgtgcgc tctcctgttc cgaccctgcc gcttaccgga tacctgtccg  47880
cctttctccc ttcgggaagc gtggcgcttt ctcatagctc acgctgtagg tatctcagtt  47940
cggtgtaggt cgttcgctcc aagctgggct gtgtgcacga accccccgtt cagcccgacc  48000
gctgcgcctt atccggtaac tatcgtcttg agtccaaccc ggtaagacac gacttatcgc  48060
cactggcagc agccactggt aacaggatta gcagagcgag gtatgtaggc ggtgctacag  48120
agttcttgaa gtggtggcct aactacggct acactagaag gacagtattt ggtatctgcg  48180
ctctgctgaa gccagttacc ttcggaaaaa gagttggtag ctcttgatcc ggcaaacaaa  48240
ccaccgctgg tagcggtggt ttttttgttt gcaagcagca gattacgcgc agaaaaaaag  48300
gatctcaaga agatcctttg atcttttcta cggggtctga cgctcagtgg aacgaaaact  48360
cacgttaagg gattttggtc atgagattat caaaaaggat cttcacctag atccttttaa  48420
attaaaaatg aagttttaaa tcaatctaaa gtatatatga gtaaacttgg tctgacagtt  48480
accaatgctt aatcagtgag gcacctatct cagcgatctg tctatttcgt tcatccatag  48540
ttgcctgact ccccgtcgtg tagataacta cgatacggga gggcttacca tctggcccca  48600
gtgctgcaat gataccgcga gacccacgct caccggctcc agatttatca gcaataaacc  48660
agccagccgg aagggccgag cgcagaagtg gtcctgcaac tttatccgcc tccatccagt  48720
ctattaattg ttgccgggaa gctagagtaa gtagttcgcc agttaatagt ttgcgcaacg  48780
ttgttgccat tgctgcaggg gggggggggg ggggggactt ccattgttca ttccacggac  48840
aaaaacagag aaaggaaacg acagaggcca aaaagcctcg ctttcagcac ctgtcgtttc  48900
ctttcttttc agagggtatt ttaaataaaa acattaagtt atgacgaaga agaacggaaa  48960
cgccttaaac cggaaaattt tcataaatag cgaaaacccg cgaggtcgcc gccccgtaac  49020
ctgtcggatc accggaaagg acccgtaaag tgataatgat tatcatctac atatcacaac  49080
gtgcgtggag gccatcaaac cacgtcaaat aatcaattat gacgcaggta tcgtattaat  49140
tgatctgcat caacttaacg taaaaacaac ttcagacaat acaaatcagc gacactgaat  49200
acggggcaac ctcatgtccc cccccccccc cccccctgcag gcatcgtggt gtcacgctcg  49260
tcgtttggta tggcttcatt cagctccggt tcccaacgat caaggcgagt tacatgatcc  49320
cccatgttgt gcaaaaaagc ggttagctcc ttcggtcctc cgatcgttgt cagaagtaag  49380
ttggccgcag tgttatcact catggttatg gcagcactgc ataattctct tactgtcatg  49440
ccatccgtaa gatgcttttc tgtgactggt gagtactcaa ccaagtcatt ctgagaatag  49500
tgtatgcggc gaccgagttg ctcttgcccg gcgtcaacac gggataatac cgcgccacat  49560
agcagaactt taaaagtgct catcattgga aaacgttctt cggggcgaaa actctcaagg  49620
atcttaccgc tgttgagatc cagttcgatg taacccactc gtgcacccaa ctgatcttca  49680
gcatctttta ctttcaccag cgtttctggg tgagcaaaaa caggaaggca aaatgccgca  49740
aaaaagggaa taagggcgac acggaaatgt tgaatactca tactcttcct ttttcaatat  49800
tattgaagca tttatcaggg ttattgtctc atgagcggat acatatttga atgtatttag  49860
```

```
aaaaataaac aaataggggt tccgcgcaca tttccccgaa aagtgccacc tgacgtctaa  49920

gaaaccatta ttatcatgac attaacctat aaaaataggc gtatcacgag gccctttcgt  49980

cttcaagaat tggtcgacga tcttgctgcg ttcggatatt ttcgtggagt tcccgccaca  50040

gacccggatt gaaggcgaga tccagcaact cgcgccagat catcctgtga cggaactttg  50100

gcgcgtgatg actggccagg acgtcggccg aaagagcgac aagcagatca cgcttttcga  50160

cagcgtcgga tttgcgatcg aggatttttc ggcgctgcgc tacgtccgcg accgcgttga  50220

gggatcaagc cacagcagcc cactcgacct tctagccgac ccagacgagc caagggatct  50280

ttttggaatg ctgctccgtc gtcaggcttt ccgacgtttg ggtggttgaa cagaagtcat  50340

tatcgtacgg aatgccaagc actcccgagg ggaaccctgt ggttggcatg cacatacaaa  50400

tggacgaacg gataaacctt ttcacgccct tttaaatatc cgttattcta ataaacgctc  50460

ttttctctta ggtttacccg ccaatatatc ctgtcaaaca ctgatagttt aaactgaagg  50520

cgggaaacga caatctgatc atgagcggag aattaaggga gtcacgttat gacccccgcc  50580

gatgacgcgg gacaagccgt tttacgtttg gaactgacag aaccgcaacg ttgaaggagc  50640

cactcagcaa gctggtacga ttgtaatacg actcactata gggcgaattg agcgctgttt  50700

aaacgctctt caactggaag agcggttact accggttaag tgactagggt c           50751


<210> SEQ ID NO 7
<211> LENGTH: 20
<212> TYPE: DNA
<213> ORGANISM: Artificial Sequence
<220> FEATURE:
<223> OTHER INFORMATION: Forward primer for GUS expression

<400> SEQUENCE: 7

cggaagcaac gcgtaaactc                                                 20


<210> SEQ ID NO 8
<211> LENGTH: 21
<212> TYPE: DNA
<213> ORGANISM: Artificial Sequence
<220> FEATURE:
<223> OTHER INFORMATION: reverse primer for GUS expression

<400> SEQUENCE: 8

tgtgagcgtc gcagaacatt a                                               21


<210> SEQ ID NO 9
<211> LENGTH: 20
<212> TYPE: DNA
<213> ORGANISM: Artificial Sequence
<220> FEATURE:
<223> OTHER INFORMATION: Probe sequence

<400> SEQUENCE: 9

cgcgtccgat cacctgcgtc                                                 20


<210> SEQ ID NO 10
<211> LENGTH: 23
<212> TYPE: DNA
<213> ORGANISM: Artificial Sequence
<220> FEATURE:
<223> OTHER INFORMATION: TERM 2.1F primer

<400> SEQUENCE: 10

ctgtcagttc caaacgtaaa acg                                             23
```

<210> SEQ ID NO 11
<211> LENGTH: 25
<212> TYPE: DNA
<213> ORGANISM: Artificial Sequence
<220> FEATURE:
<223> OTHER INFORMATION: TERM 2.1R primer

<400> SEQUENCE: 11
aatctgatca tgagcggaga attaa 25

<210> SEQ ID NO 12
<211> LENGTH: 20
<212> TYPE: DNA
<213> ORGANISM: Artificial Sequence
<220> FEATURE:
<223> OTHER INFORMATION: TERM 1F primer

<400> SEQUENCE: 12
tcccgggtcc ttaggaagac 20

<210> SEQ ID NO 13
<211> LENGTH: 21
<212> TYPE: DNA
<213> ORGANISM: Artificial Sequence
<220> FEATURE:
<223> OTHER INFORMATION: TERM 1R primer

<400> SEQUENCE: 13
tggattcagc aggcctagaa g 21

<210> SEQ ID NO 14
<211> LENGTH: 18
<212> TYPE: DNA
<213> ORGANISM: Artificial Sequence
<220> FEATURE:
<223> OTHER INFORMATION: TERM 1P-probe

<400> SEQUENCE: 14
tcctcaggat ttaaatgg 18

<210> SEQ ID NO 15
<211> LENGTH: 20
<212> TYPE: DNA
<213> ORGANISM: Artificial Sequence
<220> FEATURE:
<223> OTHER INFORMATION: Actin_Fwd primer

<400> SEQUENCE: 15
cttcgaatgc ccagcaatgt 20

<210> SEQ ID NO 16
<211> LENGTH: 21
<212> TYPE: DNA
<213> ORGANISM: Artificial Sequence
<220> FEATURE:
<223> OTHER INFORMATION: Actin _rev primer

<400> SEQUENCE: 16
gttcgcccac tagcgtacaa c 21

<210> SEQ ID NO 17
<211> LENGTH: 15
<212> TYPE: DNA
<213> ORGANISM: Artificial Sequence
<220> FEATURE:
<223> OTHER INFORMATION: Actin _probe

```
<400> SEQUENCE: 17
tcgaggctgt tcttt                                                   15

<210> SEQ ID NO 18
<211> LENGTH: 460
<212> TYPE: DNA
<213> ORGANISM: Sorghum bicolor

<400> SEQUENCE: 18
aactatctat actgtaataa tgttgtatag ccgccggata gctagctagt tagtcattca    60
gcggcgatgg gtaataataa agtgtcatcc atccatcacc atgggtggca acgtgagcaa   120
tgacctgatt gaacaaattg aaatgaaaag aagaaatatg ttatatgtca acgagatttc   180
ctcataatgc cactgacaac gtgtgtccaa gaaatgtatc agtgatacgt atattcacaa   240 ttttttatg acttatactc acaatttgtt tttttactac ttatactcga acaatttgtt    300
gtgggtacca taacaatttc gatcgaatat atatcagaaa gttgacgaaa gtaagctcac   360
tcaaaaagtt aaatgggctg cggaagctgc gtcaggccca agttttggct attctatccg   420
gtatccacga ttttgatggc tgagggacat atgttcggct                          460

Figure 6A:
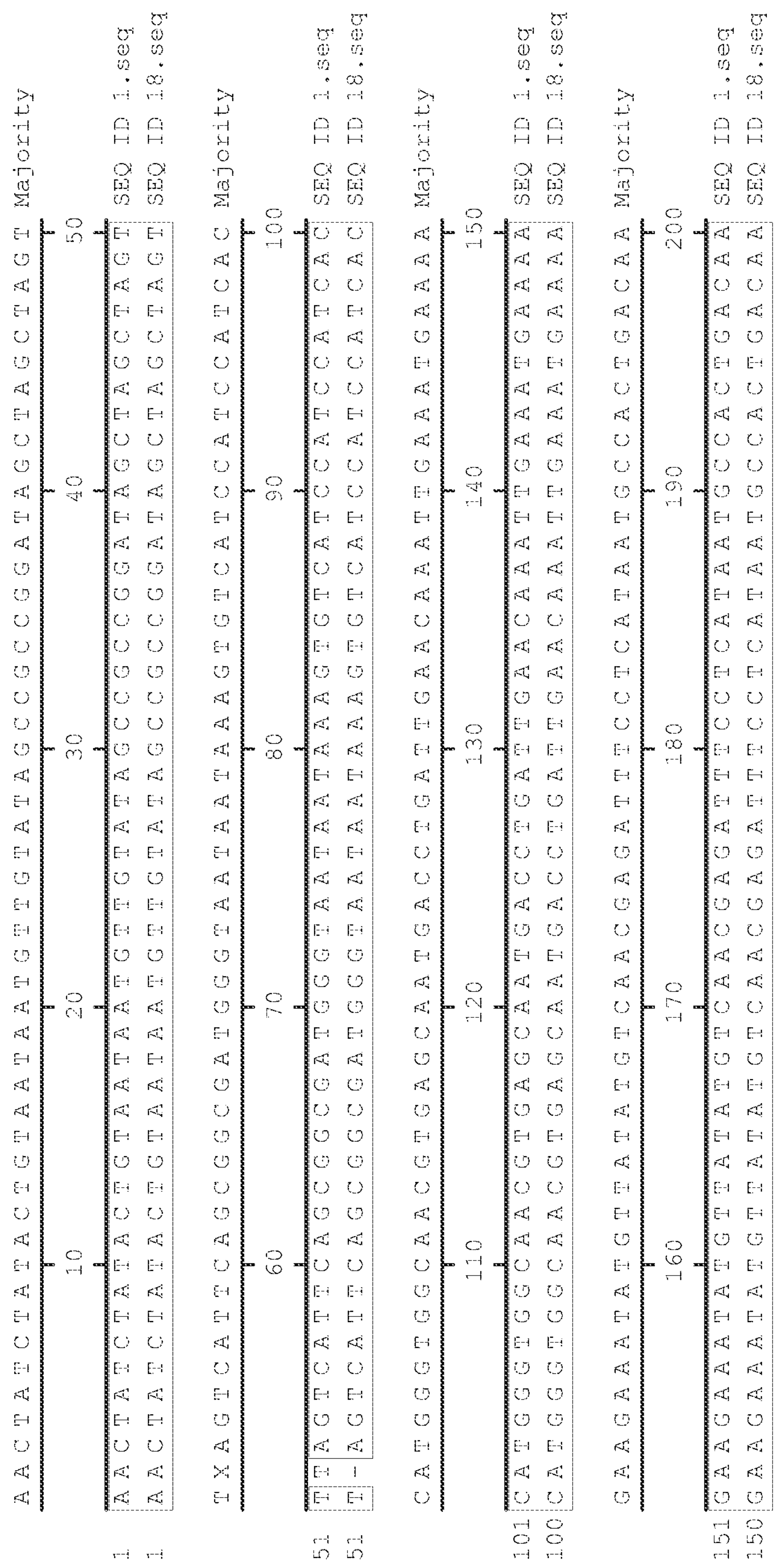

<210> SEQ ID NO 19
<211> LENGTH: 461
<212> TYPE: DNA
<213> ORGANISM: Artificial Sequence
<220> FEATURE:
<223> OTHER INFORMATION: Consensus Sequence for FIG. 6A-6C
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (290)..(291)
<223> OTHER INFORMATION: n is a, c, g, or t
<220> FEATURE:
<221> NAME/KEY: misc_feature
<222> LOCATION: (459)..(460)
<223> OTHER INFORMATION: n is a, c, g, or t

<400> SEQUENCE: 19
aactatctat actgtaataa tgttgtatag ccgccggata gctagctagt tnagtcattc    60
agcggcgatg ggtaataata aagtgtcatc catccatcac catgggtggc aacgtgagca   120
atgacctgat tgaacaaatt gaaatgaaaa gaagaaatat gttatatgtc aacgagattt   180
cctcataatg ccactgacaa cgtgtgtcca agaaatgtat cagtgatacg tatattcaca   240
atttttttat gacttatact cacaatttgt ttttttacta cttatactcn nacaatttgt   300
tgtgggtacc ataacaattt cgatcgaata tatatcagaa agttgacgaa agtaagctca   360
ctcaaaaagt taaatgggct gcggaagctg cgtcaggccc aagttttggc tattctatcc   420
ggtatccacg attttgatgg ctgagggaca tatgttcgnn t                        461
```